United States Patent
Matheny et al.

(10) Patent No.: US 8,696,744 B2
(45) Date of Patent: Apr. 15, 2014

(54) EXTRACELLULAR MATRIX MATERIAL VALVE CONDUIT AND METHODS OF MAKING THEREOF

(75) Inventors: Robert G. Matheny, Norcross, GA (US); Christian L. Gilbert, Cordova, TN (US); William Novick, Memphis, TN (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 0 days.

(21) Appl. No.: 13/480,324

(22) Filed: May 24, 2012

(65) Prior Publication Data

US 2012/0310335 A1 Dec. 6, 2012

Related U.S. Application Data

(60) Provisional application No. 61/490,693, filed on May 27, 2011, provisional application No. 61/490,873, filed on May 27, 2011, provisional application No. 61/491,723, filed on May 31, 2011, provisional application No. 61/650,911, filed on May 23, 2012.

(51) Int. Cl.
*A61F 2/24* (2006.01)

(52) U.S. Cl.
USPC ........................................ 623/2.15

(58) Field of Classification Search
USPC .............. 623/1.24, 1.26, 1.47–1.48, 2.1–2.16
See application file for complete search history.

(56) References Cited

U.S. PATENT DOCUMENTS

| | | | |
|---|---|---|---|
| 2,127,903 | A | 8/1938 | Bowen |
| 2,900,644 | A | 8/1959 | Rosenberg |
| 3,562,820 | A | 2/1971 | Braun |
| 4,098,571 | A | 7/1978 | Miyata |
| 4,466,139 | A | 8/1984 | Ketharanathan |
| 4,535,483 | A | 8/1985 | Klawitter |
| 4,798,611 | A | 1/1989 | Freeman |
| 4,801,299 | A | 1/1989 | Brendel |
| 4,902,508 | A | 2/1990 | Badylak |
| 4,956,178 | A | 9/1990 | Badylak |
| 5,275,826 | A | 1/1994 | Badylak |
| 5,281,422 | A | 1/1994 | Badylak |
| 5,352,463 | A | 10/1994 | Badylak |
| 5,372,821 | A | 12/1994 | Badylak |
| 5,445,833 | A | 8/1995 | Badylak |
| 5,480,424 | A | 1/1996 | Cox |
| 5,509,930 | A * | 4/1996 | Love ............................... 623/2.1 |

(Continued)

FOREIGN PATENT DOCUMENTS

| | | |
|---|---|---|
| EP | 2068766 | 6/2009 |
| EP | 2150283 | 2/2010 |

(Continued)

OTHER PUBLICATIONS

International Search Report and Written Opinion for International Application No. PCT/US2012/039441 (mailed Sep. 21, 2012).

(Continued)

*Primary Examiner* — Andrew Iwamaye
(74) *Attorney, Agent, or Firm* — Francis Law Group

(57) ABSTRACT

Methods for forming extracellular matrix valve conduits are disclosed. Extracellular matrix valve conduits produced using the disclosed methods are also disclosed. Methods of sterilizing and decellularizing extracellular matrix materials are also disclosed.

19 Claims, 36 Drawing Sheets

(56) References Cited

U.S. PATENT DOCUMENTS

| | | |
|---|---|---|
| 5,516,533 A | 5/1996 | Badylak |
| 5,554,389 A | 9/1996 | Badylak |
| 5,573,784 A | 11/1996 | Badylak |
| 5,641,518 A | 6/1997 | Badylak |
| 5,645,860 A | 7/1997 | Knapp, Jr. |
| 5,695,998 A | 12/1997 | Badylak |
| 5,711,969 A | 1/1998 | Patel |
| 5,713,950 A | 2/1998 | Cox |
| 5,753,267 A | 5/1998 | Badylak |
| 5,755,791 A | 5/1998 | Whitson |
| 5,762,966 A | 6/1998 | Knapp, Jr. |
| 5,866,414 A | 2/1999 | Badylak |
| 5,873,904 A | 2/1999 | Ragheb |
| 5,877,005 A | 3/1999 | Castor |
| 5,885,619 A | 3/1999 | Patel |
| 5,900,433 A | 5/1999 | Igo |
| 5,955,110 A | 9/1999 | Patel |
| 5,968,096 A | 10/1999 | Whitson |
| 5,993,844 A | 11/1999 | Abraham |
| 5,997,575 A | 12/1999 | Whitson |
| 6,045,576 A | 4/2000 | Starr |
| 6,087,157 A | 7/2000 | Badylak |
| 6,092,529 A | 7/2000 | Cox |
| 6,096,070 A | 8/2000 | Ragheb |
| 6,099,567 A | 8/2000 | Badylak |
| 6,126,686 A | 10/2000 | Badylak |
| 6,165,983 A | 12/2000 | Klaus |
| 6,187,039 B1 | 2/2001 | Hiles |
| 6,206,931 B1 | 3/2001 | Cook |
| 6,241,981 B1 | 6/2001 | Cobb |
| 6,254,636 B1 | 7/2001 | Peredo |
| 6,264,992 B1 | 7/2001 | Voytik-Harbin |
| 6,270,526 B1 | 8/2001 | Cox |
| 6,299,604 B1 | 10/2001 | Ragheb |
| 6,331,319 B1 | 12/2001 | Badylak |
| 6,358,284 B1 | 3/2002 | Fearnot |
| 6,375,989 B1 | 4/2002 | Badylak |
| 6,379,710 B1 | 4/2002 | Badylak |
| 6,444,229 B2 | 9/2002 | Voytik-Harbin |
| 6,475,232 B1 | 11/2002 | Babbs |
| 6,485,723 B1 | 11/2002 | Badylak |
| 6,579,538 B1 | 6/2003 | Spievack |
| 6,653,291 B1 | 11/2003 | Badylak |
| 6,666,892 B2 | 12/2003 | Hiles |
| 6,673,109 B2 | 1/2004 | Cox |
| 6,696,270 B2 | 2/2004 | Badylak |
| 6,719,788 B2 | 4/2004 | Cox |
| 6,726,715 B2 | 4/2004 | Sutherland |
| 6,730,064 B2 | 5/2004 | Ragheb |
| 6,733,525 B2 | 5/2004 | Yang |
| 6,773,457 B2 | 8/2004 | Ivancev |
| 6,774,278 B1 | 8/2004 | Ragheb |
| 6,793,939 B2 | 9/2004 | Badylak |
| 6,890,351 B2 | 5/2005 | Termin |
| 6,918,396 B1 | 7/2005 | Badylak |
| 6,933,326 B1 | 8/2005 | Griffey |
| 6,991,649 B2 | 1/2006 | Sievers |
| 7,033,611 B2 | 4/2006 | Lyngstadaas |
| 7,041,131 B2 | 5/2006 | Abraham |
| 7,087,034 B2 | 8/2006 | McPherson |
| 7,087,089 B2 | 8/2006 | Patel |
| 7,108,832 B2 | 9/2006 | Christensen |
| 7,121,999 B2 | 10/2006 | Abraham |
| 7,147,871 B2 | 12/2006 | Voytik-Harbin |
| 7,153,324 B2 | 12/2006 | Case |
| 7,175,841 B2 | 2/2007 | Badylak |
| 7,189,259 B2 | 3/2007 | Simionescu |
| 7,214,242 B2 | 5/2007 | Abraham |
| 7,244,444 B2 | 7/2007 | Bates |
| 7,331,993 B2 | 2/2008 | White |
| 7,361,189 B2 | 4/2008 | Case |
| 7,410,665 B2 | 8/2008 | Ragheb |
| 7,445,628 B2 | 11/2008 | Ragheb |
| 7,482,025 B2 | 1/2009 | Badylak |
| 7,485,138 B2 | 2/2009 | Fearnot |
| 7,520,894 B2 | 4/2009 | Pavcnik |
| 7,530,995 B2 | 5/2009 | Quijano |
| 7,544,207 B2 | 6/2009 | Osborne |
| 7,563,276 B2 | 7/2009 | Osborne |
| 7,604,661 B2 | 10/2009 | Pavcnik |
| 7,628,803 B2 | 12/2009 | Pavcnik |
| 7,628,804 B2 | 12/2009 | Flagle |
| 7,652,077 B2 | 1/2010 | Cook |
| 7,699,895 B2 | 4/2010 | Hiles |
| 7,713,552 B2 | 5/2010 | Bleyer |
| 7,736,385 B2 | 6/2010 | Agnew |
| 7,745,217 B2 | 6/2010 | Patel |
| 7,771,652 B2 | 8/2010 | Christopher |
| 7,771,717 B2 | 8/2010 | Badylak |
| 7,776,596 B2 | 8/2010 | Badylak |
| 7,795,022 B2 | 9/2010 | Badylak |
| 7,795,027 B2 | 9/2010 | Hiles |
| 7,815,686 B2 | 10/2010 | Badylak |
| 7,815,923 B2 | 10/2010 | Johnson |
| 7,820,634 B2 | 10/2010 | Badylak |
| 7,854,759 B2 | 12/2010 | Shirley |
| 7,857,825 B2 | 12/2010 | Moran |
| 7,871,430 B2 | 1/2011 | Pavcnik |
| 7,887,576 B2 | 2/2011 | Bahler |
| 7,909,866 B2 | 3/2011 | Stobie |
| 7,909,886 B2 | 3/2011 | Carr |
| 7,959,554 B2 | 6/2011 | McAlexander |
| 7,998,196 B2 | 8/2011 | Mathison |
| 8,003,131 B2 | 8/2011 | Badylak |
| 8,021,417 B2 | 9/2011 | Osborne |
| 8,038,710 B2 | 10/2011 | Fearnot |
| 8,049,059 B2 | 11/2011 | Bleyer |
| 8,092,522 B2 | 1/2012 | Paul |
| 8,092,529 B2 | 1/2012 | Malaviya |
| 8,128,708 B2 | 3/2012 | Hiles |
| 8,163,001 B2 | 4/2012 | Valaie |
| 8,187,619 B2 | 5/2012 | Johnson |
| 8,197,534 B2 | 6/2012 | Osborne |
| 8,257,434 B2 | 9/2012 | Matheny |
| 8,313,526 B2 | 11/2012 | Hoffman |
| 8,323,337 B2 | 12/2012 | Gurskis |
| 2002/0147497 A1 | 10/2002 | Belef |
| 2004/0043006 A1 | 3/2004 | Badylak |
| 2004/0049202 A1 | 3/2004 | Berger |
| 2004/0049262 A1 | 3/2004 | Obermiller |
| 2004/0187877 A1 | 9/2004 | Badylak |
| 2004/0191226 A1 | 9/2004 | Badylak |
| 2004/0234507 A1 | 11/2004 | Stone |
| 2005/0043216 A1 | 2/2005 | Hammarstrom |
| 2005/0096736 A1 | 5/2005 | Osse |
| 2005/0181016 A1 | 8/2005 | Freyman |
| 2005/0202058 A1 | 9/2005 | Hiles |
| 2005/0222674 A1 | 10/2005 | Paine |
| 2006/0136047 A1 | 6/2006 | Obermiller |
| 2006/0201996 A1 | 9/2006 | Hodde |
| 2006/0251702 A1 | 11/2006 | Janis |
| 2006/0259128 A1 | 11/2006 | Pavcnik |
| 2007/0014773 A1 | 1/2007 | Matheny |
| 2007/0014868 A1 | 1/2007 | Matheny |
| 2007/0014869 A1 | 1/2007 | Matheny |
| 2007/0014870 A1 | 1/2007 | Matheny |
| 2007/0014871 A1 | 1/2007 | Matheny |
| 2007/0014872 A1 | 1/2007 | Matheny |
| 2007/0014873 A1 | 1/2007 | Matheny |
| 2007/0014874 A1 | 1/2007 | Matheny |
| 2007/0112411 A1 | 5/2007 | Obermiller |
| 2007/0122390 A1 | 5/2007 | Hodde |
| 2007/0135906 A1 | 6/2007 | Badylak |
| 2007/0219487 A1 | 9/2007 | Mazgalev |
| 2007/0265699 A1* | 11/2007 | Grewe et al. ............ 623/1.24 |
| 2007/0269476 A1 | 11/2007 | Voytik-Harbin |
| 2008/0046070 A1 | 2/2008 | Obermiller |
| 2008/0063680 A1 | 3/2008 | Hiles |
| 2008/0107750 A1 | 5/2008 | Hodde |
| 2008/0145397 A1 | 6/2008 | Hiles |
| 2008/0154356 A1 | 6/2008 | Obermiller |
| 2008/0167727 A1 | 7/2008 | Cook |
| 2008/0167728 A1 | 7/2008 | Cook |
| 2008/0171092 A1 | 7/2008 | Cook |

(56) References Cited

U.S. PATENT DOCUMENTS

| | | |
|---|---|---|
| 2008/0213335 A1 | 9/2008 | Cook |
| 2008/0274184 A1 | 11/2008 | Hunt |
| 2008/0279824 A1 | 11/2008 | Matheny |
| 2008/0279833 A1 | 11/2008 | Matheny |
| 2008/0279939 A1 | 11/2008 | Firestone |
| 2008/0281419 A1 | 11/2008 | Matheny |
| 2008/0288055 A1 | 11/2008 | Paul |
| 2009/0011021 A1 | 1/2009 | Voytik-Harbin |
| 2009/0087471 A1* | 4/2009 | Shimp et al. .................. 424/423 |
| 2009/0125098 A1 | 5/2009 | Chuter |
| 2009/0142400 A1 | 6/2009 | Hiles |
| 2009/0142409 A1 | 6/2009 | Firestone |
| 2009/0157170 A1 | 6/2009 | Matheny |
| 2009/0157177 A1 | 6/2009 | Matheny |
| 2009/0204228 A1 | 8/2009 | Hiles |
| 2009/0238855 A1 | 9/2009 | Matheny |
| 2010/0010627 A1 | 1/2010 | Matheny |
| 2010/0023114 A1 | 1/2010 | Chambers |
| 2010/0028396 A1 | 2/2010 | Ward |
| 2010/0041135 A1 | 2/2010 | Badylak |
| 2010/0057201 A1 | 3/2010 | Flagle |
| 2010/0063577 A1 | 3/2010 | Case |
| 2010/0080790 A1 | 4/2010 | Matthews |
| 2010/0125327 A1 | 5/2010 | Agnew |
| 2010/0131055 A1 | 5/2010 | Case |
| 2010/0174351 A1 | 7/2010 | Ng |
| 2010/0204782 A1 | 8/2010 | Bleyer |
| 2010/0221310 A1 | 9/2010 | Virkler |
| 2010/0233235 A1 | 9/2010 | Matheny |
| 2010/0239632 A1 | 9/2010 | Walsh |
| 2010/0303886 A1 | 12/2010 | Janis |
| 2011/0081323 A1 | 4/2011 | Kleinsek |
| 2011/0165126 A1 | 7/2011 | Badylak |
| 2011/0288654 A1 | 11/2011 | Badylak |
| 2012/0016491 A1 | 1/2012 | Matheny |
| 2012/0034191 A1 | 2/2012 | Matheny |
| 2012/0156255 A1 | 6/2012 | Singh |
| 2012/0290080 A1 | 11/2012 | Matheny |
| 2012/0290081 A1 | 11/2012 | Matheny |
| 2012/0302499 A1 | 11/2012 | Matheny |
| 2012/0303117 A1 | 11/2012 | Matheny |
| 2012/0310335 A1 | 12/2012 | Matheny |

FOREIGN PATENT DOCUMENTS

| | | |
|---|---|---|
| WO | WO/98/22158 | 5/1998 |
| WO | WO/02/089711 | 11/2002 |
| WO | WO/2004/093689 | 11/2004 |
| WO | WO/2005/097219 | 3/2005 |
| WO | WO/2006/034568 | 4/2006 |
| WO | WO/2007/011644 | 1/2007 |
| WO | WO/2008/016919 | 2/2008 |
| WO | WO/2008/134610 | 11/2008 |
| WO | WO/2008/151040 | 12/2008 |
| WO | WO/2010/042856 | 4/2010 |
| WO | WO/2010/096458 | 8/2010 |
| WO | WO/2011/022369 | 2/2011 |
| WO | WO/2011/031299 | 3/2011 |
| WO | WO/2011/031827 | 3/2011 |
| WO | WO/2012/030996 | 3/2012 |
| WO | PCT/US2012/039441 | 5/2012 |
| WO | PCT/US2012/039450 | 5/2012 |
| WO | WO/2012/166538 | 12/2012 |
| WO | WO/2012/166539 | 12/2012 |
| WO | WO/2012/166549 | 12/2012 |
| WO | WO/2012/166554 | 12/2012 |

OTHER PUBLICATIONS

U.S. Appl. No. 61/490,693, filed May 27, 2011, Matheny.
U.S. Appl. No. 61/490,873, filed May 27, 2011, Matheny.
U.S. Appl. No. 13/480,347, filed May 24, 2012, Matheny.
International Search Report and Written Opinion mailed Sep. 14, 2012 for PCT/US2012/039450 (WO/2012/166554) filed May 24, 2012 (9 pages).
Abraham, G.A., et al. Evaluation of the porcine intestinal collagen layer as a biomaterial, J Biomed Mater Res, 51(3), 442-452 (2000).
Adam, O., et al. Role of RaC1 GTPase activation in atrial fibrillation, J Am Coll Cardiol 50, 359-367 (2007).
Akhyari, P., et al. Myocardial tissue engineering: the extracellular matrix, European Journal of Cardio-thoracic Surgery, 34, 229-241 (2008).
Aranki, S.F., et al. Predictors of atrial fibrillation after coronary artery surgery. Current trends and impact on hospital resources, Circulation 94, 390-397 (1996).
Badylak, S., et al. Extracellular matrix for myocardial repair, Heart Surg Forum 6(2): E20-26 (2003).
Badylak, S. The extracellular matrix as a scaffold for tissue reconstruction. Cell & Developmental Biology, 13, 377-383 (2002).
Badylak, S.F., et al. Extracellular matrix as a biological scaffold material: structure and function, Acta Biomaterialia, 5(1), 1-13 (2009).
Badylak, S.F. Xenogeneic extracellular matrix as a scaffold for tissue reconstruction, Transpl Immunol, 12(3-4), 367-377 (2004).
Beattie, A.J., et al. Chemoattraction of progenitor cells by remodeling extracellular matrix scaffolds, Tiss Eng 15, 1119-1125 (2009).
Berthonneche, C., et al. New insights into the pathological role of TNF-$\alpha$ in early cardiac dysfunction and subsequent heart failure after infarction in rats, Am J Physiol (Heart Circ Physiol) 287, H340-H350 (2004).
Bezwada, R.S., et al. Poly(p-Dioxanone) and its copolymers, in Handbook of Biodegradable Polymers, Domb, A.J., et al., editors, Harwood Academic Publishers, The Netherlands, 29-61 (1997).
Blanchard, L., et al. Non-antiarrhythmic agents for prevention of postoperative atrial fibrillation: role of statins. Current Opinion in Anaesthesiology 20, 53-56 (2007).
Boos, C.J., et al. Is atrial fibrillation an inflammatory disorder? Eur Heart J 27, 136-149 (2006).
Chan, P.S., et al. Patient health status and costs in heart failure: insights from the eplerenone post-acute myocardial infarction heart failure efficacy and survival study (EPHESUS), Circulation 119, 398-407 (2009).
Chen, Q.-Z., et al. Biomaterials in cardiac tissue engineering: ten years of research survey, Materials Science and Engineering, R59 1-37 (2008).
Chien, K.R. Lost and found: cardiac stem cell therapy revisited, J Clin Invest 116, 1838-1840 (2006).
Christman, K.L., et al. Fibrin glue alone and skeletal myoblasts in a fibrin scaffold preserve cardiac function after myocardial infarction, Tissue Eng 10, 403-409 (2004).
Cimini, M., et al. Dermal fibroblasts cultured on small intestinal submucosa: conditions for the formation of a neotissue, Journal of Biomedical Materials Research Part A, 75A(4), 895-906 (2005).
Collard, C.D., et al. Preoperative statin therapy is associated with reduced cardiac mortality after coronary artery bypass graft surgery, J Thorac Cardiovasc Surg 132, 392-400 (2006).
Cox, J.L., et al. Tubular heart valves: A new tissue prosthesis design—Preclinical evaluation of the 3F aortic bioprosthesis, Journal of Thoracic and Cardiovascular Surgery, 130(2), 520-527 (2005).
Creswell, L.L., et al. Hazards of postoperative atrial arrhythmias, Ann Thorac Surg 56, 539-549 (1993).
Dai, W., et al. Thickening of the infarcted wall by collagen injection improves left ventricular function in rats: a novel approach to preserve cardiac function after myocardial infarction, J Am Coll Cardiol 46, 714-719 (2005).
Dargie, H. Heart failure post-myocardial infarction: a review of the issues, Heart 91, (Suppl II):ii3-ii6 (2005).
Davis, M.E., et al. Injectable self-assembling peptide nanofibers create intramyocardial microenvironments for endothelial cells, Circulation 111, 442-450 (2005).
Davis, N.F., et al. Xenogenic extracellular matrices as potential biomaterials for interposition grafting in urological surgery, Journal of Urology, 184(6), 2246-2253 (2010).
Dumont, C.-E., et al. Effects of glutaraldehyde on experimental arterial iso- and allografts in rats, J Surg Res, 54(1), 61-69 (1993).
Echahidi, N., et al. Mechanisms, prevention, and treatment of atrial fibrillation after cardiac surgery, J Am Coll Cardiol 51, 793-801 (2008).

(56) References Cited

OTHER PUBLICATIONS

El-Chami, M.F., et al. New-onset atrial fibrillation predicts long-term mortality after coronary artery bypass graft, J Am Coll Cardiol 55, 1370-1376 (2010).

Elahi, M., et al. Tracing the origins of postoperative atrial fibrillation: the concept of oxidative stress-mediated myocardial injury phenomenon. European J. of Cardiovascular Prevention and Rehabilitation 15, 735-741 (2008).

Gerdisch, M.W., et al. Extracellular matrix for in vivo tissue engineered valve repair and reconstruction, Poster presented at: Fifth Biennial Meeting of the Society for Heart Valve Disease, Berlin, Germany (Jun. 27-30, 2009).

Gibbons Kroeker, C.A., et al. Pericardium modulates left and right ventricular stroke volumes to compensate for sudden changes in atrial volume, Am J Physiol Heart Circ Physiol 284, H2247-2254 (2003).

Gilbert, C.L., et al. Novel Use of Extracellular Matrix Graft for Creation of Pulmonary Valved Conduit. World J. for Pediatric and Congenital Heart Surgery, 2(3) 495-501 (2011).

Gilbert, C.L. YouTube 656918 sts video. http://www.youtube.com/watch?v=tqgj6A6WTIc (2010).

Grimes, M., et al. The effect of choice of sterilisation method on the biocompatibility and biodegradability of SIS (small intestine submucosa), Biomed Mater Eng, 15(1-2), 65-71 (2005).

Hamilton, D.R., et al. Right atrial and right ventricular transmural pressures in dogs and humans. Effects of the pericardium, Circulation 90, 2492-2500 (1994).

Hao, X., et al. Angiogenic effects of sequential release of VEGF-A165 and PDGF-BB with alginate hydrogels after myocardial infarction, Cardiovasc Res 75, 178-185 (2007).

Hodde, J., et al. Virus safety of a porcine-derived medical device: evaluation of a viral inactivation method. Biotech & Bioeng., 79(2), pp. 211-216 (2002).

Huang, N.F., et al. Injectable biopolymers enhance angiogenesis after myocardial infarction, Tissue Eng 11, 1860-1866 (2005).

Hunt, S.A., et al. ACC/AHA 2005 guideline update for the diagnosis and management of chronic heart failure in the adult, Circulation 112, e154-e235 (2005).

Ishii, Y., et al. Inflammation of atrium after cardiac surgery is associated with inhomogeneity of atrial conduction and atrial fibrillation. Circulation 111, 2881-2888 (2005).

Ji, Q., et al. Effect of preoperative atorvastatin therapy on atrial fibrillation following off-pump coronary artery bypass grafting, Circ J 73, 2244-2249 (2009).

Kocher, A.A., et al. Myocardial homing and neovascularization by human bone marrow angioblasts is regulated by IL-8/Gro CXC chemokines, J Mol Cell Cardiol 40, 455-464 (2006).

Koniari, I., et al. Pharmacologic prophylaxis for atrial fibrillation following cardiac surgery: a systematic review, J Cardiothorac Surg 5, 121-130 (2010).

Krum, H., et al. Heart failure, Lancet 373, 941-955 (2009).

Landa, N., et al. Effect of injectable alginate implant on cardiac remodeling and function after recent and old infarcts in rat, Circulation 117, 1338-1396 (2008).

Levy, D., et al. Long-term trends in the incidence of and survival with heart failure, N Eng J Med 347, 1397-1402 (2002).

Liakopoulos, O.J., et al. Impact of preoperative statin therapy on adverse postoperative outcomes in patients undergoing cardiac surgery: a meta-analysis of over 30,000 patients, Eur Heart J 29, 1548-1559 (2008).

Lindberg, K. Porcine small intestinal submucosa (SIS): a bioscaffold supporting in vitro primary human epidermal cell differentiation and synthesis of basement membrane proteins, 27(3), 254-266 (2001).

Lindsey, M.L., et al. Extracellular matrix remodeling following myocardial injury, Ann Med 35, 316-326 (2003).

Lloyd-Jones, D., et al. Heart disease and stroke statistics—2010 update: A report from the American Heart Association, Circulation 121, e46-e215 (2010).

Matheny, R.G., et al. Porcine small intestine submucosa as a pulmonary valve leaflet substitute, J Heart Valve Dis 9, 769-775 (2000).

Mathew, J.P., et al. A multicenter risk index for atrial fibrillation after cardiac surgery, JAMA 291, 1720-1729 (2004).

Matsumoto, T., et al. The fate of the inverted segment of small bowel used for the replacement of major veins, Surgery 60(3), 739-743 (1966).

McDowell, K.S., et al. Susceptibility to arrhythmia in the infarcted heart depends on myofibroblast density. Biophysical Journal 101, 1307-1315 (2011).

Mitchell, A.J., et al. Comparison of initial cell retention and clearance kinetics after subendocardial or subepicardial injections of endothelial progenitor cells in a canine myocardial infarction model, J Nucl Med 51, 413-417 (2010).

Miyahara, Y., et al. Monolayered mesenchymal stem cells repair scarred myocardium after myocardial infarction, Nat Med 12, 459-465 (2006).

Naji, F., et al. Comparison of atorvastatin and simvastatin in prevention of atrial fibrillation after successful cardioversion, Int Heart J 50, 153-160 (2009).

Ninio, D.M., et al. Passive pericardial constraint protects against stretch-induced vulnerability to atrial fibrillation in rabbits, Am J Physiol Heart Circ Physiol 291, H2547-H2549 (2006).

Orlic, D., et al. Bone marrow cells regenerate infarcted myocardium, Nature 410, 701-705 (2001).

Ott, H.C., et al. Perfusion-decellularized matrix: using nature's platform to engineer a bioartificial heart, Nat Med 14, 213-221 (2008).

Palmer, E.M., et al. Human helper T cell activation and differentiation is suppressed by porcine small intestinal submucosa, Tissue Eng 8, 893-900 (2002).

Patti, G., et al. Randomized trial of atorvastatin for reduction of postoperative atrial fibrillation in patients undergoing cardiac surgery: Results of the ARMYDA-3 (Atorvastatin for Reduction of MYocardial Dysrhythmia After cardiac surgery) study, Circulation 114, 1455-1461 (2006).

Pendyala, L., et al. Cellular cardiomyoplasty and cardiac regeneration, Curr Cardiol Rev 4, 72-80 (2008).

Reffelmann, T., et al. Cellular cardiomyoplasty—cardiomyocytes, skeletal myoblasts, or stem cells for regenerating myocardium and treatment of heart failure? Cardiovasc Res 58, 358-368 (2003).

Reil, J.C., et al. Cardiac RaC1 overexpression in mice creates a substrate for atrial arrhythmias characterized by structural remodelling, Cardiovasc Res 87, 485-493 (2010).

Reing, J.E., et al. Degradation products of extracellular matrix affect cell migration and proliferation, Tiss Eng 15, 605-614 (2009).

Robinson, K.A., et al. Extracellular matrix scaffold for cardiac repair, Circulation, 112[suppl I], pp. I-135-I-143 (2005).

Robotin-Johnson, M.C., et al. An experimental model of small intestinal submucosa as a growing vascular graft, J Thorac Cardiovasc Surg, 116(5), 805-811 (1998).

Rosso, F., et al. From cell-ECM interactions to tissue engineering, J Cell Physiol. 199, 174-180 (2004).

Schächinger, V., et al. Intracoronary bone marrow-derived progenitor cells in acute myocardial infarction, N Engl J Med 355, 1210-1221 (2006).

Schnabel, R.B., et al. Relation of multiple inflammatory biomarkers to incident atrial fibrillation, Am J Cardiol 104(1), 92-96 (2009).

Sundaresan, M., et al. Regulation of reactive-oxygen-species generation in fibroblasts by Rac1, Biochem J 318, 379-382 (1996).

Taylor, P.M., et al. Extracellular matrix scaffolds for tissue engineering heart valves, Progress in Pediatric Cardiology, 21(2), 219-225 (2006).

Thielmann, M., et al. Lipid-lowering effect of preoperative statin therapy on postoperative major adverse cardiac events after coronary artery bypass surgery, J Thorac Cardiovasc Surg 134, 1143-1149 (2007).

Tsang, K.Y., et al. The developmental roles of the extracellular matrix: beyond structure to regulation, Cell Tissue Res, 339, 93-110 (2010).

Voytik-Harbin, S.L., et al. Identification of extractable growth factors from small intestinal submucosa. J. Cell. Biochem., 67, 478-491 (1997).

Wang, C.-Y., et al. Pleiotropic effects of statin therapy: molecular mechanisms and clinical results, Trends Mol Med 14, 37-44 (2008).

(56) References Cited

OTHER PUBLICATIONS

Wassmann, S., et al. Inhibition of geranylgeranylation reduces angiotensin II—mediated free radical production in vascular smooth muscle cells: involvement of angiotensin AT1 receptor expression and Rac1 GTPase, Mol Pharmacol 59, 646-654 (2001).

White, J.K., et al. A stentless trileaflet valve from a sheet of decellularized porcine small intestinal submucosa, Ann Thorac Surg, 80(2), 704-707 (2005).

Wöhrle, J., et al. Results of intracoronary stem cell therapy after acute myocardial infarction, Am J Cardiol 105, 804-812 (2010).

Wu, K., et al. Application of stem cells for cardiovascular grafts tissue engineering, Transplant Immunology, 16(1), 1-7 (2006).

Xie, Y., et al. Effects of fibroblast-myocyte coupling on cardiac conduction and vulnerability to reentry: a computational study, Heart Rhythm 6(11), 1641-1649 (2009).

Yoo, D., et al. Adhesive epicardial corticosteroids prevent postoperative atrial fibrillation, Circ Arrhythm Electrophysiol 3, 505-510 (2010).

Zhao, Z.-Q., et al. Improvement in cardiac function with small intestine extracellular matrix is associated with recruitment of C-Kit cells, myofibroblasts, and macrophages after myocardial infarction, J Am Coll Cardiol, 55, 1250-1261 (2010).

Zimmermann, W.-H., et al. Heart muscle engineering: an update on cardiac muscle replacement therapy, Cardiovascular Research, 71, 419-429 (2006).

* cited by examiner

EXTRACELLULAR MATRIX MATERIAL VALVE CONDUIT AND METHODS OF MAKING THEREOF

CROSS-REFERENCE TO RELATED APPLICATIONS

This application claims the benefit of the filing dates of U.S. Provisional Patent Application No. 61/490,693, filed on May 27, 2011, U.S. Provisional Patent Application No. 61/490,873, filed on May 27, 2011, U.S. Provisional Patent Application No. 61/491,723, filed on May 31, 2011, and U.S. Provisional Patent Application No. 61/650,911, filed on May 23, 2012, each of which is hereby incorporated by reference herein in its entirety.

FIELD

The invention generally relates to extracellular matrix material valve conduits and methods of making such valve conduits. More particularly, the invention relates to methods of forming valve conduits from sheets or conduits of extracellular matrix materials, as well as the extracellular matrix material valve conduits resulting from such methods.

BACKGROUND

Cardiac surgeons currently employ a variety of techniques to accomplish valvular reconstruction within the hearts of patients. For example, cryo-preserved allografts, bovine jugular vein grafts, porcine valves, and autologous pericardium have all been used in such valvular reconstruction procedures. However, these known techniques all suffer from several major limitations. More specifically, cryo-preserved allografts are prone to calcification and failure over time, and the high costs and low availability of allografts limit the utility of allografts in developing countries. These grafts also increase the likelihood that the anti-human antibodies of a patient will react with, and ultimately reject, a future heart transplant due to prior antigen exposure. Jugular vein grafts, although widely available, can only be provided in a narrow range of sizes, and the jugular vein grafts are prone to undesired calcification and aneurysmal dilatation. Similarly, porcine valves calcify over time, leading to a significant decrease in the integrity of the valves, particularly in children. Autologous pericardium has been used with short-term success; however, the procedures employing autologous pericardium are typically complicated and time-consuming, and are, therefore, unsuited for use in most countries. Moreover, autologous pericardium calcifies over time, and a patient's own pericardium cannot be used as a replacement valve material when the patient has had previous heart surgeries.

Additionally, known valve conduits that are employed in valvular reconstruction procedures are typically formed from multiple pieces, such as, for example, a graft portion and a valve portion. Thus, before these valve conduits can be used, the valve portion must be properly secured within the graft portion. This limitation adds significant complexity and time to the overall procedure, and the two-part structure of the resulting valve conduits can contribute to failure of the device.

Furthermore, at a fundamental level, known valve conduits are used to replace a defective valve rather than to regenerate a native valve. Thus, following implantation, these valve conduits are incapable of achieving formation of a physiologically and anatomically correct replacement valve.

In developing countries, cost and supply constraints limit the widespread use of alternative conduits for valvular reconstruction operations. Thus, there is a need for a readily available, low-cost valve replacement material that can easily be used during surgical procedures in developing countries.

Accordingly, there is a need in the art for a heart valve conduit that, upon implantation within the heart of a subject, is configured to promote regeneration of a replacement heart valve, including leaflets and sinus portions that are identical or substantially identical to the leaflets and sinus portions of a native valve. There is a further need for a unitary, implantable heart valve conduit that distally integrates into a native artery such that, over time, the synthetic material of the heart valve conduit is undetectable. There is still a further need for a sterile, acellular, and low-cost heart valve conduit that can be quickly and efficiently constructed using readily available materials or that is pre-constructed for rapid implantation.

SUMMARY

Methods for regenerating semi-lunar valves to replace defective semi-lunar valves within the heart of a subject are disclosed. In one disclosed method, a defective semi-lunar valve is removed from the heart of the subject. A sheet of extracellular matrix (ECM) material is positioned in a folded position, in which a bottom edge of the sheet is folded toward a top edge of the sheet such that the bottom edge of the sheet is spaced a selected distance from the top edge of the sheet. The sheet of ECM material is secured in the folded position at a first attachment point and a second attachment point, thereby forming a folded ECM material construct. The folded ECM material construct is positioned in an aligned position, in which a first side edge of the folded ECM material construct is in substantial alignment with a second side edge of the folded ECM material construct. With the folded ECM material construct in the aligned position, the first side edge is secured to the second side edge, thereby forming an ECM material valve conduit.

The ECM material valve conduit has a lumen, an inlet portion defining an inlet and having an inner layer and an outer layer, and an outlet portion defining an outlet. The inner layer of the inlet portion is positioned within the lumen, while the outer layer of the inlet portion cooperates with the outlet portion to define an outer wall of the ECM material valve conduit. The ECM material valve conduit is attached to an annular region or outlet of the heart of the subject and to an artery of the subject such that the inlet portion of the ECM material valve conduit is positioned proximate the annular region. The inner layer of the ECM material valve conduit includes leaflet-promoting portions for regenerating leaflets, and the outer layer of the ECM material valve conduit includes sinus-promoting formations for regenerating sinus portions of the replacement semi-lunar valve. ECM material valve conduits that are formed and used according to the described methods are also disclosed.

BRIEF DESCRIPTION OF THE DRAWINGS

These and other features of the preferred embodiments of the invention will become more apparent in the detailed description in which reference is made to the appended drawings wherein:

FIG. 7 is an image of the right ventricular outflow tract of the regenerated pulmonary valve. FIG. 8 is an image of the leaflets of the regenerated pulmonary valve. FIG. 9 is an image of the regenerated pulmonary valve, as observed from the right ventricle of the heart of the sheep. FIG. 10 is an image depicting the progress of leaflet formation in the regenerated pulmonary valve. FIG. 11 is an image depicting the progress of sinus formation in the regenerated pulmonary valve.

FIGS. 12 and 13 are images of exemplary extracellular matrix valve conduits prior to hydration. FIG. 14 is an image of an exemplary extracellular matrix valve conduit following hydration.

FIGS. 15, 16, and 23 depict valve conduits that were implanted into the heart of a patient during the study, while FIGS. 17-22 are images of echocardiograms that were recorded during the study.

FIG. 25 depicts Doppler echocardiography images taken postoperatively for an exemplary extracellular matrix material valve conduit as described herein.

FIG. 26 includes images of a regenerated pulmonary valve at various time points following implantation of an exemplary extracellular matrix material valve conduit as described herein.

FIG. 27 shows the DNA content of each SIS composition following sterilization. FIG. 28 shows the percentage of DNA that was removed from each SIS composition following sterilization, as compared to raw, unprocessed SIS.

FIG. 29 shows the bFGF content of each SIS composition (normalized by dry weight of samples) following sterilization. FIG. 30 shows the active TGF-$\beta$ content of each SIS composition (normalized by dry weight of samples) following sterilization.

FIG. 31 shows the bFGF content for each SIS composition (normalized by dry weight of samples) following rapid depressurization.

FIG. 32 shows the tensile strength measured for each SIS composition following sterilization.

FIG. 33 shows the bFGF enzyme-linked immunosorbent assay (ELISA) results for each SIS composition (normalized by dry weight of samples) following sterilization and/or decellularization.

DETAILED DESCRIPTION

Figure 1:
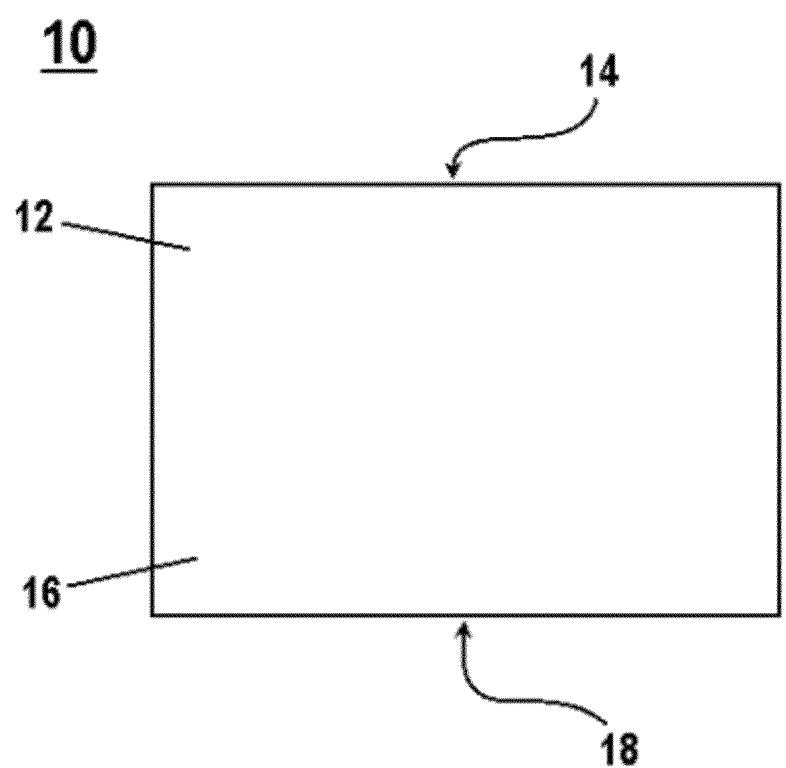
FIG. 1 depicts an exemplary sheet of extracellular matrix material, as described herein.

The present invention may be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to an "attachment point" can include two or more such attachment points unless the context indicates otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" and "optionally" mean that the subsequently described event or circumstance may or may not occur, and that the description includes instances where said event or circumstance occurs and instances where it does not.

The word "or" as used herein means any one member of a particular list and also includes any combination of members of that list.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Without the use of such exclusive terminology, the term "comprising" in the claims shall allow for the inclusion of any additional element—irrespective of whether a given number of elements is enumerated in the claim or the addition of a feature could be regarded as transforming the nature of an element set forth in the claims. Except as specifically defined herein, all technical and scientific terms used herein are to be given as broad a commonly understood meaning as possible while maintaining claim validity.

As used herein, a "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects. As used herein, the term "subject" can be used interchangeably with the term "patient."

As used herein, the term "circumference" refers to the perimeter of, or length of the boundary defined by, a closed planar figure. Optionally, as used herein, a "circumference" can correspond to the perimeter of a closed planar circle. However, it is contemplated that a "circumference" can correspond to the perimeter of any closed planar figure, such as, for example and without limitation, an oval, square, rectangular, trapezoidal, or nonsymmetrical closed planar figure. For example, as used herein, an outer "circumference" of a conduit corresponds to the perimeter of the closed planar figure defined by an outer surface of the conduit at a particular location along the longitudinal axis of the conduit.

As used herein, the term "acellular" is meant to describe extracellular matrix compositions that are at least 80% decellularized such that the extracellular matrix composition is at least 80% without cells and/or cellular remnants. In some exemplary aspects described herein, the term "acellular" can refer to extracellular matrix compositions that are at least 90% decellularized such that the extracellular matrix composition is at least 90% without cells and/or cellular remnants. In other exemplary aspects described herein, the term "acellular" can refer to extracellular matrix compositions that are at least 95% decellularized such that the extracellular matrix composition is at least 95% without cells and/or cellular remnants. In other exemplary aspects described herein, the term "acellular" can refer to extracellular matrix compositions that are at least 96% decellularized such that the extracellular matrix composition is at least 96% without cells and/or cellular remnants. In still other exemplary aspects described herein, the term "acellular" can refer to extracellular matrix compositions that are at least 97% decellularized such that the extracellular matrix composition is at least 97% without cells and/or cellular remnants. In further exemplary aspects described herein, the term "acellular" can refer to extracellular matrix compositions that are at least 98% decellularized such that the extracellular matrix composition is at least 98% without cells and/or cellular remnants. In still further exemplary aspects described herein, the term "acellular" can refer to extracellular matrix compositions that are at least 99% decellularized such that the extracellular matrix composition is at least 99% without cells and/or cellular remnants. Thus, as used herein, the term "acellular" can refer to extracellular matrix compositions that are decellularized at levels of 80%, 81%, 82%, 83%, 84%, 85%, 86%, 87%, 88%, 89%, 90%, 91%, 92%, 93%, 94%, 95%, 96%, 97%, 98%, 99%, 100%, and any percentages falling between these values.

As used herein, the term "additive" refers to materials that can be selectively incorporated into the disclosed ECM materials to impart predetermined properties to the sterilized, acellular ECM compositions disclosed herein. Such additives can include, for example and without limitation, growth factors, cytokines, proteoglycans, glycosaminoglycans (GAGs), proteins, peptides, nucleic acids, small molecules, cells and pharmaceutical agents, such as statin drugs, corticosteroids, anti-arrhythmic drugs, nonsteroidal anti-inflammatory drugs, other anti-inflammatory compounds, nanoparticles, and metallic compounds.

As used herein, the term "contemporaneously" refers to the simultaneous and/or overlapping occurrence of events, as well as the sequential occurrence of events within about thirty minutes before or after one another. Thus, if a first event occurs, then a second event can be said to have occurred contemporaneously with the first event if it occurred concurrently with the first event or within thirty minutes before or after the first event. For example, if a first method step is performed, then a second method step performed five minutes after the first method step can be said to be performed "contemporaneously" with the first method step. Similarly, if the second method step was performed ten minutes before performance of a third method step, then the second method step can be said to be performed "contemporaneously" with the third method step.

As used herein, the term "supercritical" refers to a fluid state of a material when it is held at or above its critical temperature and critical pressure. When a material is held at or above its critical temperature and critical pressure, then it typically adopts functional properties of both a gas and a liquid and is said to function as a supercritical fluid. Thus, for example, when carbon dioxide is held at or above its critical temperature (31.1° C.) and its critical pressure (1,071 psi), it behaves as a supercritical carbon dioxide fluid and can, for example, exhibit the expansion properties of a gas while having the density of a liquid.

Described herein are valve conduits made from extracellular matrix (ECM) material. In exemplary aspects, the ECM material valve conduits regenerate a semi-lunar (tri-leaflet) valve, such as a pulmonary valve or an aortic valve within a heart of a subject. In these aspects, the ECM material valve conduits can regenerate a semi-lunar valve to replace a defective semi-lunar valve within the heart of the subject. It is contemplated that such defective semi-lunar valves can be attached at an annular region between a ventricle of the heart of the subject and an artery of the subject. As used herein, the term "annular region" refers to the portion of the heart of a subject that is proximate to the native position of an annulus between a ventricle within the heart of the subject and an artery of the subject. When an annulus is positioned within the heart of the subject, the annular region includes the annulus as well as the heart muscle proximate the annulus. When the annulus has been removed from the heart of the subject, the annular region includes the heart muscle proximate the former position of the annulus within the heart of the subject.

In exemplary aspects, a disclosed ECM material valve conduit can comprise any known ECM component or material, including, for example and without limitation, mucosal layers and components, submucosal layers and components, muscularis layers and components, and/or basement membrane layers and components. It is contemplated that a disclosed ECM material valve conduit can comprise an ECM material obtained from any mammalian tissue source, including, for example and without limitation, stomach tissue (e.g., stomach submucosa (SS)), small intestinal tissue (e.g., small intestinal submucosa (SIS)), large intestinal tissue, bladder tissue (e.g., urinary bladder submucosa (UBS)), liver tissue (e.g., liver basement membrane (LBM)), heart tissue (e.g., pericardium), lung tissue, kidney tissue, pancreatic tissue, prostate tissue, mesothelial tissue, fetal tissue, a placenta, a ureter, veins, arteries, heart valves with or without their attached vessels, tissue surrounding the roots of developing teeth, and tissue surrounding growing bone. It is further contemplated that a disclosed ECM material valve conduit can comprise an ECM material obtained from ECM components or materials of one or more mammals including, for example and without limitation, humans, cows, pigs, dogs, sheep, cats, horses, rodents, and the like. Thus, it is contemplated that a disclosed ECM material valve conduit can comprise ECM components or materials from two or more of the same mammalian species, such as, for example and without limitation, two or more cows, two or more pigs, two or more dogs, or two or more sheep. It is further contemplated that a disclosed ECM material valve conduit can comprise ECM components or materials from two or more different mammalian species, such as, for example and without limitation, a pig and a cow, a pig and a dog, a pig and a sheep, or a cow and a sheep. It is still further contemplated that a disclosed ECM material valve conduit can comprise ECM components or materials obtained from a first tissue source, such as, for example and without limitation, SIS, from a first mammal, as well as ECM components or materials obtained from a second tissue source, such as, for example and without limitation, SS, from a second mammal.

In one aspect, and with reference to FIGS. 3A-4 and 6A-6B, a disclosed ECM material valve conduit 40, 140 can have a longitudinal axis 41, 141 and can comprise a lumen 42, 142, an inlet portion 44, 144, and an outlet portion 56, 156. In this aspect, it is contemplated that the lumen 42, 142 can have an inner diameter. Optionally, the inner diameter of the lumen 42, 142 can be substantially constant along the longitudinal axis 41, 141 of the ECM material valve conduit 40, 140. In exemplary aspects, it is contemplated that the inner diameter of the lumen 42, 142 can range from about 15 mm to about 30 mm. In a further aspect, it is contemplated that the ECM material valve conduit 40, 140 can have a longitudinal length (along longitudinal axis 41, 141) ranging from about 20 mm to about 40 mm, and more preferably, from about 22 mm to about 34 mm.

In another aspect, the outlet portion 56, 156 can define an outlet 58, 158 in communication with the lumen 42, 142 of a disclosed ECM material valve conduit 40, 140. In an additional aspect, the inlet portion 44, 144 can define an inlet 46, 146 in communication with the lumen 42, 142 of a disclosed ECM material valve conduit 40, 140 and comprise an outer layer and an inner layer 48, 148 positioned within the lumen of the ECM material valve conduit. In this aspect, it is contemplated that the inner layer 48, 148 and the outer layer of the inlet portion 44, 144 can be of unitary, continuous construction, with the inner layer being inwardly reflected within the lumen 42, 142 of the ECM material valve conduit 40, 140. Thus, it is contemplated that, due to the unitary and continuous construction of the inner layer 48, 148 and the outer layer, the inner layer and the outer layer do not have to be secured to one another proximate the inlet 46, 146 of the ECM material valve conduit 40, 140.

In a further aspect, the inner layer 48, 148 of the inlet portion 44, 144 of a disclosed ECM material conduit 40, 140 can be attached to the outer layer of the inlet portion 44, 144 of the ECM material conduit at a plurality of attachment points 34, 134, such as, for example, two or three attachment points. In this aspect, it is contemplated that the plurality of attachment points 34, 134 can be substantially equally spaced along an outer circumference of the ECM material valve conduit 40, 140. It is further contemplated that the plurality of attachment points 34, 134 can be positioned substantially within a common plane that is substantially perpendicular to the longitudinal axis 41, 141 of the ECM material valve conduit 40, 140. In another aspect, the inner layer 48, 148 of the outlet portion 56, 156 can be attached to the outer layer at the plurality of attachment points 34, 134 using any conventional surgical attachment means, including, for example and without limitation, non-absorbable sutures, absorbable sutures, surgical pastes, surgical glues, staples, and the like. In this aspect, it is contemplated that, when non-absorbable sutures are used to secure the inner layer 48, 148 to the outer layer, the knots of each suture can be positioned in contact with the outer wall such that the outer wall is positioned between the inner layer and the knots, thereby ensuring that the knots will not extend into the lumen 42, 142 following implantation of the ECM material valve conduit 40, 140. In exemplary aspects, the inner layer and outer layers 48, 148 can be secured to one another using a cruciate suture pattern. In still a further aspect, the outer layer of the inlet portion of a disclosed ECM material valve conduit 40, 140 can cooperate with the outlet portion of the ECM material valve conduit to define an outer wall 52, 152 of the ECM material valve conduit.

Figure 3A:
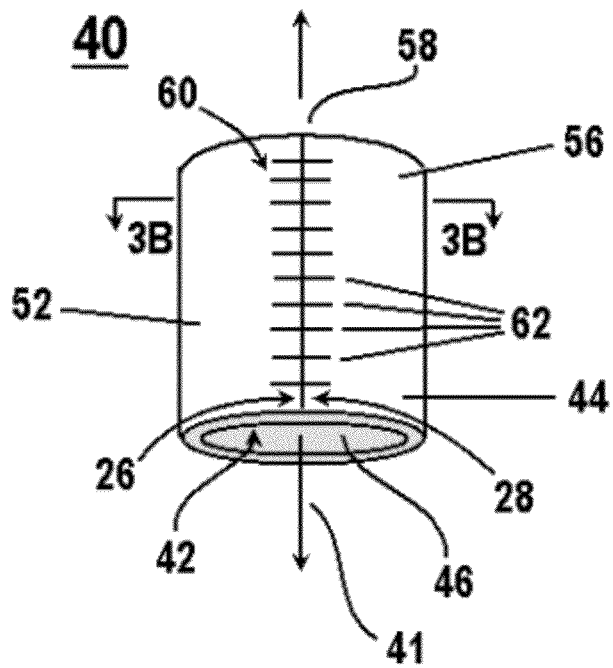
FIG. 3A is a side perspective view of an extracellular matrix material valve conduit formed from the sheet of FIGS. 1-2B, as described herein.
Figure 3B:
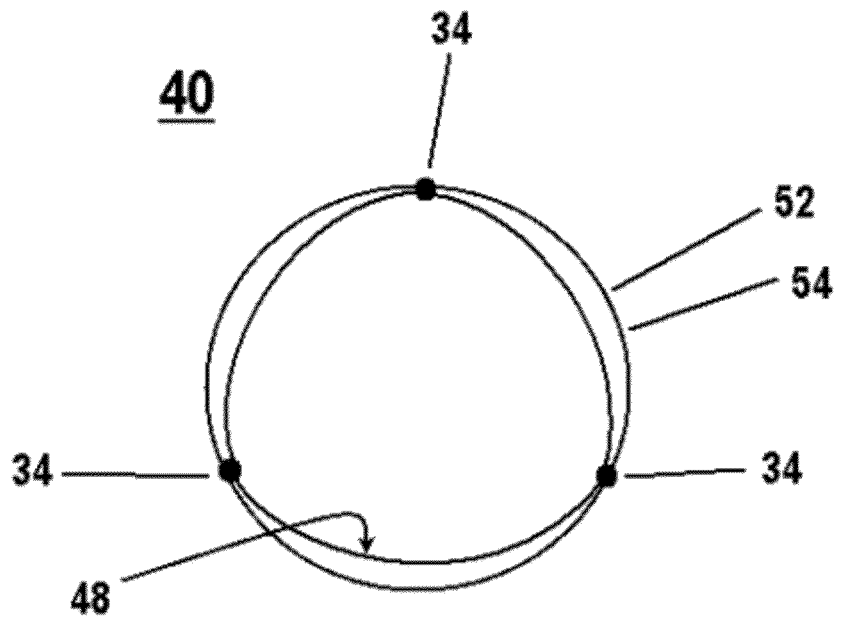
FIG. 3B is a top view of the extracellular matrix material valve conduit.
Figure 4:
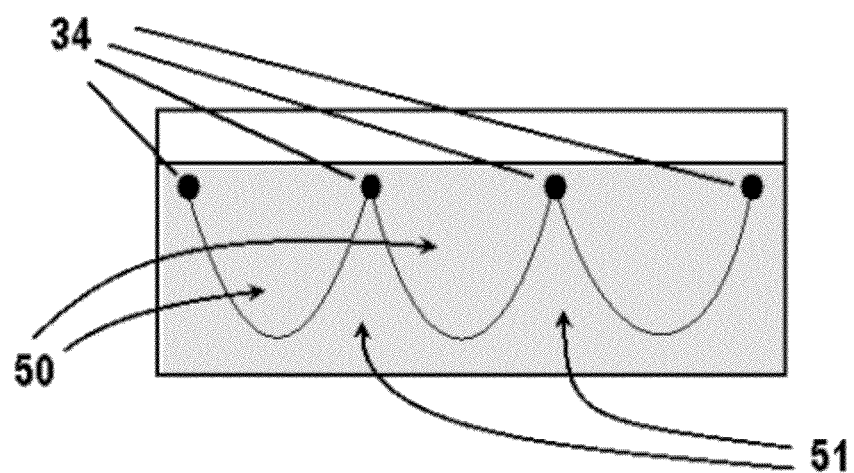
FIG. 4 is a schematic depiction of the leaflet-promoting portions and sinus-promoting portions of the inner layer of the extracellular matrix material valve conduit depicted in FIGS. 3A and 3B.

In an additional aspect, and with reference to FIGS. 3B and 4, the inner layer 48, 148 of the inlet portion 44, 144 of a disclosed ECM material valve conduit 40, 140 can comprise leaflet-promoting portions 50, 150. In this aspect, it is contemplated that, following attachment of the ECM material valve conduit 40, 140 to an annular region of the heart of the subject and an artery of the subject such that the inlet portion 44, 144 of the ECM material valve conduit is positioned proximate the annular region, the leaflet-promoting portions 50, 150 of the inner layer 48, 148 can be configured to regenerate three leaflets of a replacement semi-lunar valve. In exemplary aspects, each leaflet-promoting portion 50, 150 of the inner layer 48, 148 can have a longitudinal length. In these aspects, it is contemplated that the longitudinal length of the leaflet-promoting portions 50, 150 can optionally be greater than or equal to the length of the regenerated leaflets of the replacement semi-lunar valve, as measured by the elongate length of the regenerated leaflets extending from the valve conduit wall. For example, it is contemplated that the ratio between the longitudinal length of the leaflet-promoting portions 50, 150 and the length of the regenerated leaflets can be 1.0:1, 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, 3.9:1, 4.0:1, and any ratios falling between these values. In other optional aspects, it is contemplated that the longitudinal length of the leaflet-promoting portions 50, 150 can be less than the length of the regenerated leaflets of the replacement semi-lunar valve.

In another aspect, and with reference to FIG. 3B, it is contemplated that at least a portion of the outer wall 52, 152 (i.e., the outer layer of the inlet portion 44, 144) of a disclosed ECM material valve conduit 40, 140 can comprise sinus-promoting portions 54, 154. In this aspect, it is contemplated that, following attachment of the ECM material valve conduit 40, 140 to the annular region and the artery, the sinus-promoting portions 54, 154 of the outer wall 52, 152 of the ECM material valve conduit can be configured to fuse with the inner layer 48, 148 of the ECM material valve conduit to regenerate sinus portions of the replacement semi-lunar valve.

In a further aspect, and with reference to FIGS. 3B and 4, it is contemplated that the inner layer 48, 148 of the inlet portion 44, 144 of a disclosed ECM material valve conduit 40, 140 can further comprise commissure-promoting portions 51, 151. In this aspect, it is contemplated that, following attachment of the ECM material valve conduit 40, 140 to the annular region and the artery, the commissure-promoting portions 51, 151 can be configured to fuse with at least a portion of the outer wall 52, 152 (e.g., the outer layer of the inlet portion 44, 144). Thus, it is contemplated that the continuity of the inner layer 48, 148 and the outer wall 52, 152 can permit the inner layer and the outer wall to cooperate in promoting the regeneration of the replacement semi-lunar valve.

Optionally, the ECM material valve conduit 40, 140 can have a multi-laminate structure. In exemplary aspects, the ECM material valve conduit 40, 140 can comprise between 2 and 10 layers laminated together. In an exemplary aspect, the ECM material valve conduit can be a four-ply (four layer) multi-laminate structure. It is contemplated that such a multi-laminate structure can increase the structural integrity of the ECM material valve conduit.

Methods of Forming the ECM Material Valve Conduits from a Sheet of ECM Material

In exemplary aspects, a disclosed ECM material valve conduit can be formed from a sheet of ECM material. In these aspects, the sheet of ECM material can comprise any known ECM component or material, including, for example and without limitation, mucosal layers and components, submucosal layers and components, muscularis layers and components, and/or basement membrane layers and components. Optionally, the sheet of ECM material can have a multi-laminate structure that is produced by conventional methods. It is contemplated that a disclosed ECM material valve conduit can comprise an ECM material obtained from any mammalian tissue source, including, for example and without limitation, stomach tissue (e.g., stomach submucosa (SS)), small intestinal tissue (e.g., small intestinal submucosa (SIS)), large intestinal tissue, bladder tissue (e.g., urinary bladder submucosa (UBS)), liver tissue (e.g., liver basement membrane (LBM)), heart tissue (e.g., pericardium), lung tissue, kidney tissue, pancreatic tissue, prostate tissue, mesothelial tissue, fetal tissue, a placenta, a ureter, veins, arteries, heart valves with or without their attached vessels, tissue surrounding the roots of developing teeth, and tissue surrounding growing bone. In one aspect, the sheet of ECM material can have a width ranging from about 20 mm to about 150 mm. In an additional aspect, the sheet of ECM material can have a thickness ranging from about 0.02 mm to about 3 mm. It is contemplated that the sheet of ECM material can have any length that is appropriate for desired folding of the sheet and for desired attachment of a disclosed ECM material valve conduit within the heart of a subject.

In one aspect, and with reference to FIGS. 1-4, a method of forming a disclosed ECM material valve conduit 40 from a sheet 10 of ECM material can comprise positioning the sheet of ECM material in a folded position. In this aspect, it is contemplated that the sheet of ECM material 10 can have a top portion 12 comprising a top edge 14 of the sheet and a bottom portion 16 comprising a bottom edge 18 of the sheet. It is further contemplated that, in the folded position, the bottom edge 18 of the sheet 10 of ECM material can be spaced a selected distance 20 from the top edge 14 of the sheet, thereby forming a sewing cuff. In one aspect, in the folded position, the selected distance 20 by which the bottom edge 18 is spaced from the top edge 14 can range from about 0 mm to about 150 mm. In this aspect, it is contemplated that the selected distance 20 can be any distance that permits desired attachment of the ECM material valve conduit 40 to an artery of a subject. In exemplary aspects, the selected distance 20 can be about 10 mm.

Figure 2A:
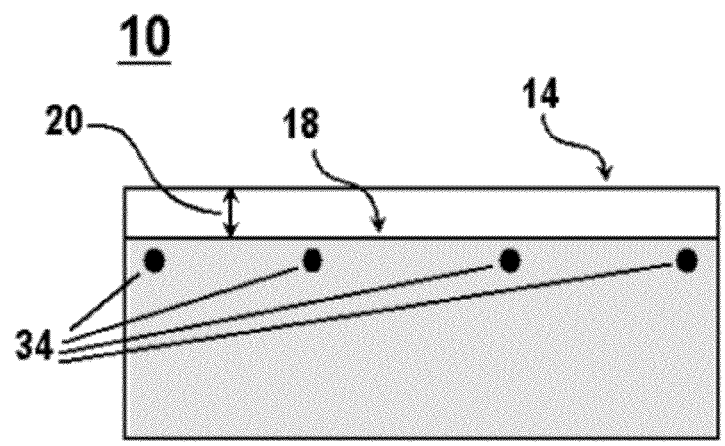
FIG. 2A is a top view of the sheet of FIG. 1 in a folded position, as described herein.
Figure 2B:
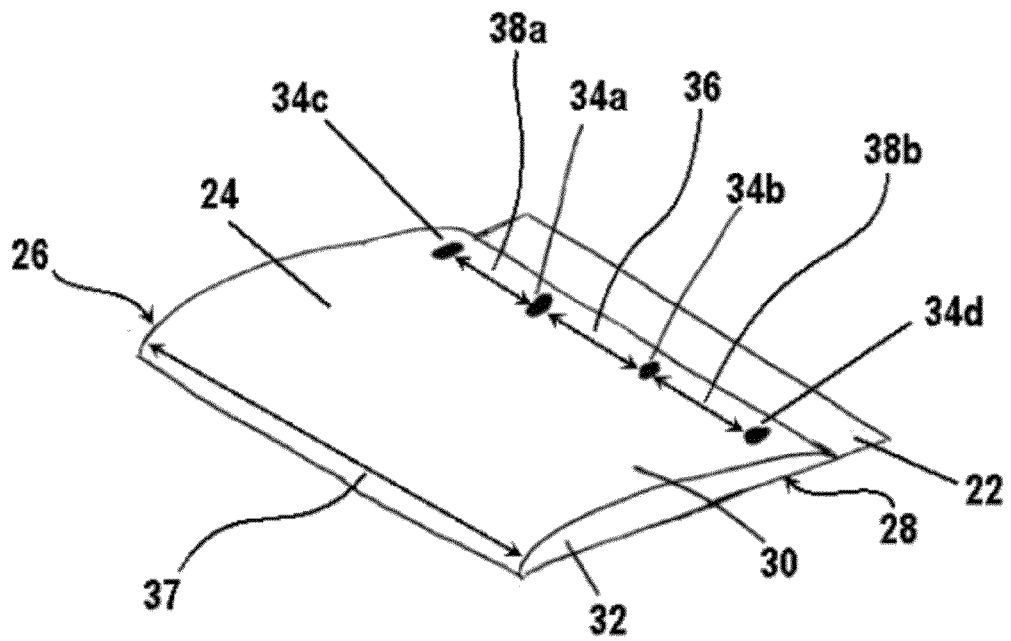
FIG. 2B is a side perspective view of the sheet in the folded position.

In another aspect, as shown in FIGS. 2A and 2B, the method of forming a disclosed ECM material valve conduit can comprise securing the sheet 10 of ECM material in the folded position, thereby forming a folded ECM material construct. In this aspect, the folded ECM material construct can have an upper portion 22, a lower portion 24, a first side edge 26, and a second side edge 28. In one aspect, the lower portion 24 of the folded ECM material construct can comprise a first layer 30 and a second layer 32. In this aspect, the first layer 30 of the lower portion 24 can correspond to the folded bottom portion 16 of the sheet 10 of ECM material. In an additional aspect, as depicted in FIGS. 2A and 2B, the first layer 30 of the lower portion 24 of the folded ECM material construct can be attached to the second layer 32 of the lower portion 24 of the folded ECM material construct at a first attachment point 34a and a second attachment point 34b. In this aspect, it is contemplated that the first attachment point 34a can be spaced from the second attachment point 34b by a selected distance 36. It is contemplated that the selected distance 36 by which the first attachment point 34a is spaced from the second attachment point 34b can range from about ¼ to about ½ the width 37 of the sheet 10 of ECM material. Thus, it is contemplated that the selected distance 36 by which the first attachment point 34a is spaced from the second attachment point 34b can range from about 5 mm to about 75 mm. In exemplary aspects, the selected distance 36 by which the first attachment point 34a is spaced from the second attachment point 34b can be about ⅓ the width 37 of the sheet 10 of ECM material. In a further aspect, it is contemplated that the first layer 30 of the lower portion 24 of the folded ECM material construct can be attached to the second layer 32 of the lower portion using any conventional surgical attachment means, including, for example and without limitation, non-absorbable sutures, absorbable sutures, surgical pastes, surgical glues, staples, and the like. In this aspect, it is contemplated that, when non-absorbable sutures are used to secure the first layer 30 to the second layer 32, the knots of each suture can be positioned in contact with the second layer such that the second layer is positioned between the first layer and the knots. In exemplary aspects, the first and second layers 30, 32 can be secured to one another using a cruciate suture pattern.

In another aspect, the first layer 30 of the lower portion 24 of the folded ECM material construct can optionally be further attached to the second layer 32 of the lower portion of the folded ECM material construct at a third attachment point 34c intermediate the first side edge 26 of the folded ECM material construct and the first attachment point 34a. In this aspect, it is contemplated that the distance 38a by which the third attachment point 34c is spaced from the first attachment point 34a can be substantially equal to the selected distance 36 by which the first attachment point is spaced from the second attachment point 34b. It is further contemplated that the third attachment point 34c can be spaced from the first side edge 26 of the folded ECM material construct by a selected distance ranging from about 1 mm to about 2 mm and, more preferably, being about 1.5 mm.

In still another aspect, the first layer 30 of the lower portion 24 of the folded ECM material construct can optionally be further attached to the second layer 32 of the lower portion of the folded ECM material construct at a fourth attachment point 34d intermediate the second side edge 28 of the folded ECM material construct and the second attachment point 34b. In this aspect, it is contemplated that the distance 38b by which the fourth attachment point 34d is spaced from the second attachment point 34b can be substantially equal to the selected distance 36 by which the first attachment point 34a is spaced from the second attachment point. It is further contemplated that the fourth attachment point 34d can be spaced from the second side edge 28 of the folded ECM material construct by a selected distance ranging from about 1 mm to about 2 mm and, more preferably, being about 1.5 mm.

In a further aspect, and with reference to FIG. 3A, the method of forming a disclosed ECM material valve conduit can comprise positioning the folded ECM material construct in an aligned position. In this aspect, it is contemplated that, in the aligned position, the first side edge 26 of the folded ECM material construct can be in substantial alignment with the second side edge 28 of the folded ECM material construct. In exemplary aspects, it is contemplated that the aligned position can correspond to a position in which the first side edge 26 and the second side edge 28 are rolled or otherwise advanced toward one another until the first and second side edges are substantially adjacent to one another. In these aspects, the first side edge 26 and the second side edge 28 can be advanced toward one another such that the second layer 32 of the lower portion 24 and the upper portion 22 of the folded ECM material construct cooperate to define a substantially cylindrical ECM material construct, with the first layer of the lower portion of the folded ECM material construct being positioned within and extending from a periphery of the substantially cylindrical ECM material construct. Optionally, it is contemplated that the aligned position can correspond to a position in which the first and second side edges 26, 28 are in an overlapping configuration. It is further contemplated that the aligned position can correspond to a position in which the first and second side edges are everted relative to the lumen 42 of the ECM material valve conduit.

In an additional aspect, and with reference to FIGS. 3A and 3B, with the folded ECM material construct in the aligned position, the first side edge 26 of the folded ECM material construct can be secured to the second side edge 28 of the folded ECM material construct, thereby forming an ECM material valve conduit 40 comprising a lumen 42 and having a longitudinal axis 41. In this aspect, it is contemplated that the first side edge 26 and the second side edge 28 of the folded ECM material construct can be secured such that the first side edge 26 and the second side edge 28 are everted relative to the lumen 42 of the resulting ECM material valve conduit 40. In exemplary aspects, the first and second attachment points 34a, 34b can be positioned substantially within a common plane that is substantially perpendicular to the longitudinal axis 41 of the ECM material valve conduit 40. In these aspects, it is further contemplated that the third attachment point 34c and/or fourth attachment point 34d, when present, can also be positioned within the common plane. In a further aspect, it is contemplated that the first side edge 26 can be secured to the second side edge 28 using any conventional surgical attachment means, including, for example and without limitation, non-absorbable sutures, absorbable sutures, surgical pastes, surgical glues, staples, and the like. In an exemplary aspect, it is contemplated that the attachment means used to secure the first side edge to the second side edge can form a seam 60 along the longitudinal length of the ECM material valve conduit. In this aspect, when two attachment points 34 have been used to attach the first layer 30 of the folded ECM material construct to the second layer 32 of the folded ECM material construct, it is contemplated that the seam 60 can function as a third attachment point that, in exemplary configurations, can be substantially equally radially spaced from the first and second attachment points. Alternatively, when three or four attachment points 34 have been used to attach the first layer 30 of the folded ECM material construct to the second layer 32 of the folded ECM material construct, it is contemplated that the third and/or fourth attachment points 34c, 34d can be positioned proximate the first and/or second side edges 26, 28 such that, after the first side edge is secured to the second side edge as described herein, the seam 60 can be positioned proximate the third and/or fourth attachment point(s). In exemplary aspects, as shown in FIG. 3A, the seam 60 can be formed from a plurality of sutures 62 spaced along the longitudinal axis 41 of the ECM material valve conduit 40. In other exemplary aspects, the seam 60 can comprise a continuous suture, such as, for example and without limitation, a continuous 6-0 polypropylene suture.

In one aspect, the lower portion 24 of the folded ECM material construct can correspond to an inlet portion 44 of the ECM material valve conduit 40. In this aspect, the inlet portion 44 of the ECM material valve conduit 40 can define an inlet 46 in fluid communication with the lumen 42 of the ECM material valve conduit. In another aspect, the first layer 30 of the lower portion 24 of the folded ECM material construct can correspond to an inner layer 48 positioned within the lumen 42 of the ECM material valve conduit 40. In still another aspect, the second layer 32 of the lower portion 24 of the folded ECM material construct can cooperate with the upper portion 22 of the folded ECM material construct to define an outer wall 52 of the ECM material valve conduit 40. In yet another aspect, the upper portion 22 of the folded ECM material construct can correspond to an outlet portion 56 of the ECM material valve conduit 40. In this aspect, the outlet portion 56 of the ECM material valve conduit 40 can define an outlet 58 in fluid communication with the lumen 42 of the ECM material valve conduit.

Methods of Forming the ECM Material Valve Conduits from an ECM Material Conduit

Figure 5:
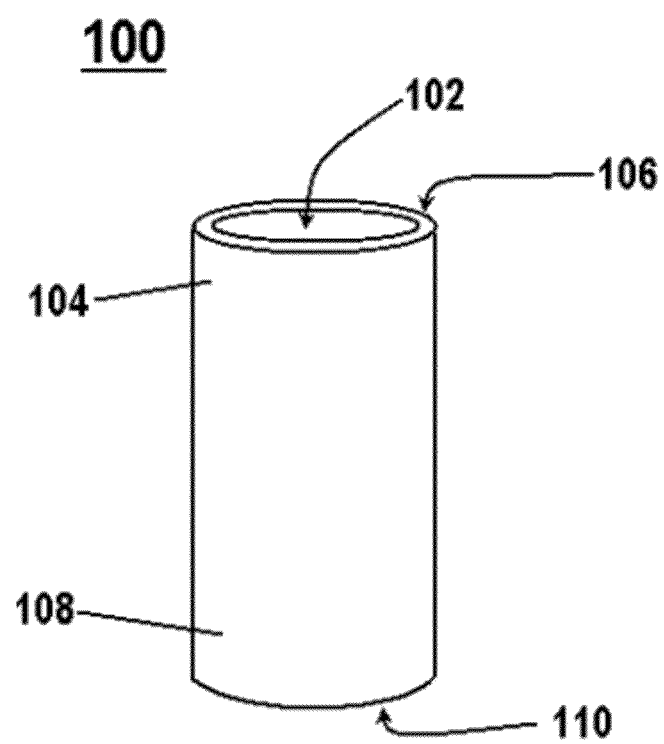
FIG. 5 is a perspective view of an extracellular matrix material conduit, as described herein.
Figure 6A:
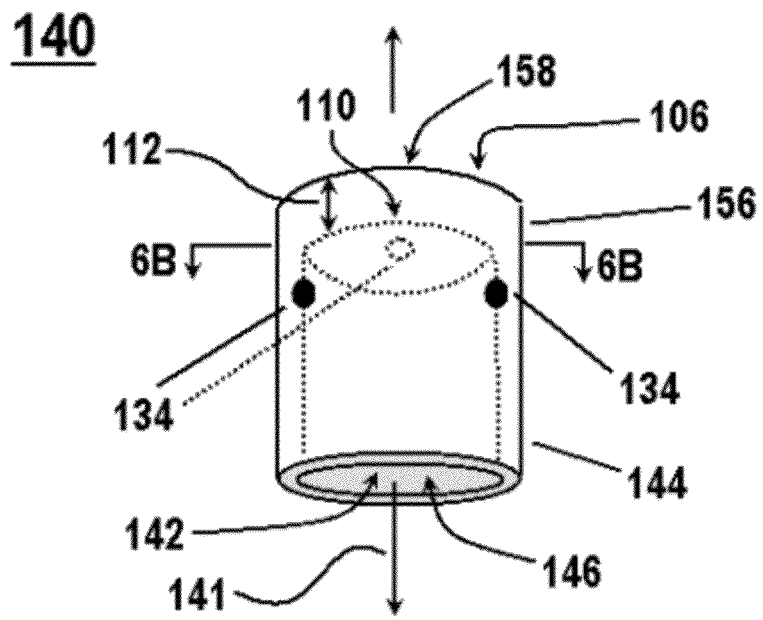
FIG. 6A is a side perspective view of the extracellular matrix conduit of FIG. 5 in a reflected position, thereby forming an extracellular matrix material valve conduit.
Figure 6B:
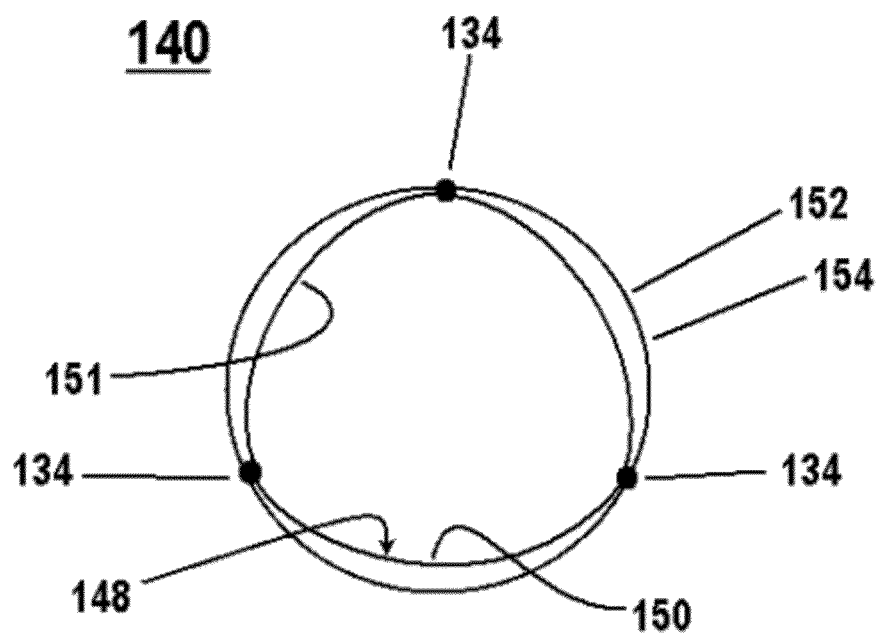
FIG. 6B is a top view of the extracellular matrix valve conduit.

In exemplary aspects, and with reference to FIGS. 5-6B, a disclosed ECM material valve conduit 140 can be formed from an ECM material conduit 100. In these aspects, the ECM material conduit 100 can comprise any known ECM component or material, including, for example and without limitation, mucosal layers and components, submucosal layers and components, muscularis layers and components, and/or basement membrane layers and components. Optionally, the ECM material conduit 100 can have a multi-laminate structure that is produced by conventional methods. It is contemplated that a disclosed ECM material valve conduit 140 can comprise an ECM material obtained from any mammalian tissue source, including, for example and without limitation, stomach tissue (e.g., stomach submucosa (SS)), small intestinal tissue (e.g., small intestinal submucosa (SIS)), large intestinal tissue, bladder tissue (e.g., urinary bladder submucosa (UBS)), liver tissue (e.g., liver basement membrane (LBM)), heart tissue (e.g., pericardium), lung tissue, kidney tissue, pancreatic tissue, prostate tissue, mesothelial tissue, fetal tissue, a placenta, a ureter, veins, arteries, heart valves with or without their attached vessels, tissue surrounding the roots of developing teeth, and tissue surrounding growing bone. In one aspect, the ECM material conduit 100 that is used to form the ECM material valve conduit 140 can be obtained by resecting an intact, lumenal portion of a mammalian tissue source, such as, for example and without limitation, an intact, lumenal portion of the small intestine of a mammal. In this aspect, it is contemplated that selected layers of the intact portion of the mammalian tissue source can be removed following resection.

In an additional aspect, it is contemplated that a disclosed ECM material valve conduit 140 can be formed from ECM that is produced using known in vitro methods. For example, a disclosed ECM material conduit 100 can be formed by growing cells on an outer surface of a cylindrical mandrel using known in vitro methods. It is contemplated that the growth of cells on the outer surface of the mandrel can lead to production of one or more ECM materials.

In one aspect, and with reference to FIGS. 5-6B, a method of forming a disclosed ECM material valve conduit 140 from an ECM material conduit 100 can comprise positioning the ECM material conduit in a reflected position. In this aspect, it is contemplated that the ECM material conduit 100 can define a lumen 102 and have a top portion 104 and a bottom portion 108. It is further contemplated that the top portion 104 of the ECM material conduit 100 can comprise a top end 106 of the ECM material conduit, while the bottom portion 108 of the ECM material conduit can comprise a bottom end 110 of the ECM material conduit. In an additional aspect, it is contemplated that the step of positioning the ECM material conduit 100 in the reflected position can comprise inwardly reflecting the bottom end 110 of the ECM material conduit within the lumen 102 of the ECM material conduit toward the top end 106 of the ECM material conduit. It is further contemplated that, in the reflected position, the bottom end 110 of the ECM material conduit 100 can be spaced a selected distance 112 from the top end 106 of the ECM material conduit. In one aspect, in the folded position, the selected distance 112 by which the bottom end 110 is spaced from the top end 106 can range from about 0 mm to about 150 mm. In this aspect, it is contemplated that the selected distance 112 can be any distance that permits desired attachment of the ECM material valve conduit 140 to an artery of a subject.

In another aspect, the method of forming a disclosed ECM material valve conduit can comprise securing the ECM material conduit 100 in the reflected position, thereby forming an ECM material valve conduit 140. In this aspect, the ECM material valve conduit 140 comprises a lumen 142, an inlet portion 144, and an outlet portion 156 and can have a longitudinal axis 141 and an outer circumference. In one aspect, the outlet portion 156 can define an outlet 158 in communication with the lumen 142 of a disclosed ECM material valve conduit 140. In an additional aspect, the inlet portion 144 can define an inlet 146 in communication with the lumen 142 of a disclosed ECM material valve conduit 140 and can comprise an outer layer and an inner layer 148 positioned within the lumen of the ECM material valve conduit. In this aspect, it is contemplated that the inner layer 148 of the inlet portion 144 of the ECM material valve conduit 140 can correspond to the reflected bottom end 110 of the ECM material conduit 100. In a further aspect, the inner layer 148 can be attached to the outer layer at three attachment points 134. In this aspect, it is contemplated that the three attachment points 134 can be substantially equally spaced along the outer circumference of the ECM material valve conduit 140. For example, it is contemplated that the three attachment points 134 can be spaced from adjacent attachment points by a distance ranging from about 5 mm to about 75 mm along the outer circumference of the ECM material valve conduit 140. It is further contemplated that the three attachment points 134 can be positioned substantially within a common plane that is substantially perpendicular to the longitudinal axis 141 of the ECM material valve conduit 140. In still another aspect, the outer layer of the inlet portion 144 of the ECM material valve conduit 100 can cooperate with the outlet portion 156 of the ECM material valve conduit to define an outer wall 152 of the ECM material valve conduit.

In an additional aspect, the method of forming a disclosed ECM material valve conduit can comprise lyophilizing the ECM material valve conduit using known methods. In a further aspect, when a disclosed ECM material valve conduit has been lyophilized, the method of forming the ECM material valve conduit can further comprise hydrating the ECM material valve conduit using known methods. In this aspect, it is contemplated that the lyophilized ECM material valve conduit can be hydrated in sterile water, saline solution, or a balanced salt solution for a period ranging from about 5 minutes to about 30 minutes.

In exemplary aspects, it is contemplated that the ECM material valve conduits 40, 140 described herein can be sterilized and/or decellularized using known methods or as disclosed herein. In these aspects, such sterilization and/or decellularization steps can be performed at any stage in the construction of the ECM material valve conduit prior to implantation of the ECM material valve conduit within a subject. In one aspect, it is contemplated that the ECM material valve conduits 40, 140 described herein can be sterilized using ethylene oxide gas.

In one aspect, a disclosed ECM material valve conduit can comprise a sterile, acellular ECM composition. In exemplary aspects, such a sterile, acellular ECM composition can be formed by contemporaneously sterilizing and decellularizing an isolated ECM material. More particularly, as disclosed in the following methods, desired sterilization and decellularization of the isolated ECM material can occur contemporaneously such that the native properties of the tissue composition are maintained and the ECM material is rendered sterile and acellular.

Sterilization/Decellularization of ECM Compositions for Use in ECM Valve Conduits As described herein, the disclosed methods make use of rapid depressurization of an isolated ECM material to render the ECM material acellular. This rapid depressurization of the ECM material occurs at depressurization rates that are significantly higher than the depressurization rates applied in previously known methods. In addition to rendering acellular the ECM material as described herein, the rapid depressurization of the ECM material also can be used to enhance the incorporation of desired sterilants and additives into the ECM material. Further, it is contemplated that the rapid depressurization of the ECM material can render the ECM material acellular while also improving retention of native growth factors, as compared to previously known decellularization methods. Still further, it is contemplated that the rapid depressurization of the ECM material can be used to improve retention of the tensile strength of the ECM material, as compared to previously known decellularization methods.

The disclosed methods not only do not significantly weaken the mechanical strength and bioptric properties of the ECM compositions, but also the methods are more effective in decellularizing the ECM compositions and in enhancing the incorporation of various additives into the ECM compositions. Thus, the disclosed sterilization and decellularization methods provide ECM compositions that are more decellularized and have a greater capacity to incorporate and then deliver more additives than ECM compositions known in the art. Moreover, the disclosed sterilization and decellularization methods provide ECM compositions that have greater amounts and/or concentrations of retained native growth factors and that have greater tensile strength than sterilized and decellularized ECM compositions known in the art.

Optionally, it is contemplated that the ECM material of a disclosed ECM material valve conduit can be sterilized using a known sterilization system, such as, for example and without limitation, the system described in U.S. Pat. No. 7,108,832, assigned to NovaSterilis, Inc., which patent is expressly incorporated herein by reference in its entirety. Thus, in some aspects, the system used to perform the disclosed methods can comprise a standard compressed storage cylinder and a standard air compressor used in operative association with a booster (e.g., a Haskel Booster AGT 7/30). In other aspects, the air compressor and booster can be replaced with a single compressor. In exemplary aspects, the compressed storage cylinder can be configured to receive carbon dioxide, and the booster can be a carbon dioxide booster.

The system can further comprise an inlet port, which allows one or more additives contained in a reservoir to be added to a reactor vessel through a valve and an additive line. As used herein, the term "reactor vessel" refers to any container having an interior space that is configured to receive an ECM material and permit exposure of the ECM material to one or more sterilants and additives, as disclosed herein. In exemplary aspects, the reactor vessel can be, without limitation, a basket, a bucket, a barrel, a box, a pouch, and other known containers. In one aspect, it is contemplated that the reactor vessel can be a syringe that is filled with an ECM material.

It is contemplated that a selected primary sterilant, such as, for example and without limitation, carbon dioxide, can be introduced to the reactor vessel from a header line via a valve and a supply line. It is further contemplated that a filter, such as, for example and without limitation, a 0.5 μm filter, can be provided in the supply line to prevent escape of material from the vessel. In exemplary aspects, a pressure gauge can be provided downstream of a shut-off valve in the header line to allow the pressure to be visually monitored. A check valve can be provided in the header line upstream of the valve to prevent reverse fluid flow into the booster. In order to prevent an overpressure condition existing in the header line, a pressure relief valve can optionally be provided.

In one aspect, depressurization of the reactor vessel can be accomplished using an outlet line and a valve in communication with the reactor vessel. In this aspect, it is contemplated that the depressurized fluid can exit the vessel via the supply line, be filtered by a filter unit, and then be directed to a separator, where filtered fluid, such as carbon dioxide, can be exhausted via an exhaust line. It is further contemplated that valves can be incorporated into the various lines of the apparatus to permit fluid isolation of upstream components.

In one exemplary aspect, the reactor vessel can comprise stainless steel, such as, for example and without limitation, 316 gauge stainless steel. In another exemplary aspect, the reactor vessel can have a total internal volume sufficient to accommodate the materials being sterilized, either on a laboratory or commercial scale. For example, it is contemplated that the reactor vessel can have a length of about 8 inches, an inner diameter of about 2.5 inches, and an internal volume of about 600 mL. In additional aspects, the reactor vessel can comprise a vibrator, a temperature control unit, and a mechanical stirring system comprising an impeller and a magnetic driver. In one optional aspect, it is contemplated that the reactor vessel can contain a basket comprising 316 gauge stainless steel. In this aspect, it is contemplated that the basket can be configured to hold materials to be sterilized while also protecting the impeller and directing the primary sterilant in a predetermined manner.

It is contemplated that the reactor vessel can be operated at a constant pressure or under continual pressurization and depressurization (pressure cycling) conditions without material losses due to splashing or turbulence, and without contamination of pressure lines via back-diffusion. It is further contemplated that the valves within the system can permit easy isolation and removal of the reactor vessel from the other components of the system. In one aspect, the top of the reactor vessel can be removed when depressurized to allow access to the interior space of the reactor vessel.

Optionally, the system can comprise a temperature control unit that permits a user to adjustably control the temperature within the reactor vessel.

In use, the disclosed apparatus can be employed in a method of producing a sterilized, acellular ECM composition, such as disclosed herein. However, it is understood that the disclosed apparatus is merely exemplary, and that any apparatus capable of performing the disclosed method steps can be employed to produce the sterilized, acellular ECM composition. Thus, the claimed method is in no way limited to a particular apparatus.

It is contemplated that significant reductions in colony-forming units (CFUs) can be achieved in accordance with the disclosed methods by subjecting an isolated ECM material to sterilization temperature and pressure conditions using a primary sterilant. Optionally, it is contemplated that the primary sterilant can be combined with one or more secondary sterilants to achieve desired sterilization. Optionally, it is further contemplated that selected additives can be incorporated into an ECM material to impart desired characteristics to the resulting ECM composition. It is still further contemplated that the disclosed methods can be employed to produce sterilized, acellular ECM compositions for implantation within the body of a subject.

As described herein, the disclosed methods make use of rapid depressurization of an isolated ECM material to render the ECM material acellular. This rapid depressurization of the ECM material occurs at depressurization rates that are significantly higher than the depressurization rates applied in previously known methods. In addition to rendering acellular the ECM material as described herein, the rapid depressurization of the ECM material also can be used to enhance the incorporation of desired sterilants and additives into the ECM material. Further, it is contemplated that the rapid depressurization of the ECM material can render the ECM material acellular while also improving retention of native growth factors, as compared to previously known decellularization methods. Still further, it is contemplated that the rapid depressurization of the ECM material can be used to improve retention of the tensile strength of the ECM material, as compared to previously known decellularization methods.

The disclosed methods not only do not significantly weaken the mechanical strength and bioptric properties of the ECM compositions, but also the methods are more effective in decellularizing the ECM compositions and in enhancing the incorporation of various additives into the ECM compositions. Thus, the disclosed sterilization and decellularization methods provide ECM compositions that are more decellularized and have a greater capacity to incorporate and then deliver more additives than ECM compositions known in the art. Moreover, the disclosed sterilization and decellularization methods provide ECM compositions that have greater amounts and/or concentrations of retained native growth factors and that have greater tensile strength than sterilized and decellularized ECM compositions known in the art.

In exemplary aspects, the primary sterilant can be carbon dioxide at or near its supercritical pressure and temperature conditions. However, it is contemplated that any conventional sterilant, including, for example, gas, liquid, or powder sterilants that will not interfere with the native properties of the ECM material can be used as the primary sterilant.

In one exemplary aspect, the disclosed sterilization process can be practiced using carbon dioxide as a primary sterilant at pressures ranging from about 1,000 to about 3,500 psi and at temperatures ranging from about 25° C. to about 60° C. More preferably, when supercritical carbon dioxide is used, it is contemplated that the sterilization process can use carbon dioxide as a primary sterilant at pressures at or above 1,071 psi and at temperatures at or above 31.1° C. In this aspect, the ECM material to be sterilized can be subjected to carbon dioxide at or near such pressure and temperature conditions for times ranging from about 10 minutes to about 24 hours, more preferably from about 15 minutes to about 18 hours, and most preferably, from about 20 minutes to about 12 hours. Preferably, the carbon dioxide employed in the disclosed systems and methods can be pure or, alternatively, contain only trace amounts of other gases that do not impair the sterilization properties of the carbon dioxide. For ease of further discussion below, the term "supercritical carbon dioxide" will be used, but it will be understood that such a term is non-limiting in that carbon dioxide within the pressure and temperature ranges as noted above can be employed satisfactorily in the practice of the disclosed methods. Within the disclosed pressure and temperature ranges, it is contemplated that the carbon dioxide can be presented to the ECM material in a gas, liquid, fluid or plasma form.

The secondary sterilants employed in the disclosed methods can, in some aspects, include chemical sterilants, such as, for example and without limitation, peroxides and/or carboxylic acids. Preferred carboxylic acids include alkanecarboxylic acids and/or alkanepercarboxylic acids, each of which can optionally be substituted at the alpha carbon with one or more electron-withdrawing substituents, such as halogen, oxygen and nitrogen groups. Exemplary species of chemical sterilants employed in the practice of the disclosed methods include, for example and without limitation, hydrogen peroxide ($H_2O_2$), acetic acid (AcA), peracetic acid (PAA), trifluoroacetic acid (TFA), and mixtures thereof. In one exemplary aspect, the chemical sterilants can include Sporeclenz® sterilant, which is a mixture comprising acetic acid, hydrogen peroxide, and peracetic acid.

It is contemplated that the secondary sterilants can be employed in a sterilization-enhancing effective amount of at least about 0.001 vol. % and greater, based on the total volume of the primary sterilant. It is further contemplated that the amount of secondary sterilant can be dependent upon the particular secondary sterilant that is employed. Thus, for example, it is contemplated that peracetic acid can be present in relatively small amounts of about 0.005 vol. % and greater, while acetic acid can be employed in amounts of about 1.0 vol. % and greater. Thus, it is contemplated that the concentration of the secondary sterilants can range from about 0.001 vol. % to about 2.0 vol. % and can typically be used as disclosed herein to achieve a sterilization-enhancing effect in combination with the disclosed primary sterilants, such as, for example and without limitation, supercritical carbon dioxide.

In one aspect, the method of producing a sterilized, acellular ECM composition can comprise harvesting a selected tissue from a mammal and rinsing the selected tissue in sterile saline or other biocompatible liquid known to a person of skill in the art, such as, for example and without limitation, Ringer's solution and a balanced biological salt solution. In this aspect, the selected tissue can be, for example and without limitation, stomach tissue (e.g., stomach submucosa (SS)), small intestinal tissue (e.g., small intestinal submucosa (SIS)), large intestinal tissue, bladder tissue (e.g., urinary bladder submucosa (UBS)), liver tissue (e.g., liver basement membrane (LBM)), heart tissue (e.g., pericardium, epicardium, endocardium, myocardium), lung tissue, kidney tissue, pancreatic tissue, prostate tissue, mesothelial tissue, fetal tissue, a placenta, a ureter, veins, arteries, heart valves with or without their attached vessels, tissue surrounding the roots of developing teeth, and tissue surrounding growing bone. In another aspect, the method can comprise freezing the selected tissue for a period ranging from about 12 to about 36 hours, more preferably, from about 18 to about 30 hours, and most preferably, from about 22 to about 26 hours. For example, it is contemplated that the period during which the selected tissue is frozen can be 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, and any other period of time falling between the preceding values. In an additional aspect, the method can comprise thawing the selected tissue in cold hypotonic tris buffer. Optionally, in this aspect, the method can comprise thawing the selected tissue in cold hypotonic tris buffer on ice with 5 mM ethylenediaminetetraacetic acid (EDTA). In exemplary aspects, it is contemplated that the steps of freezing and thawing the selected tissue can be cyclically repeated up to six times.

In another aspect, the method can comprise isolating an ECM material from the selected tissue. In this aspect, the ECM material can be any material comprising known extracellular matrix components, including, for example and without limitation, stomach tissue (e.g., stomach submucosa (SS)), small intestinal tissue (e.g., small intestinal submucosa (SIS)), large intestinal tissue, bladder tissue (e.g., urinary bladder submucosa (UBS)), liver tissue (e.g., liver basement membrane (LBM)), heart tissue (e.g., pericardium, epicardium, endocardium, myocardium), lung tissue, kidney tissue, pancreatic tissue, prostate tissue, mesothelial tissue, fetal tissue, a placenta, a ureter, veins, arteries, heart valves with or without their attached vessels, tissue surrounding the roots of developing teeth, and tissue surrounding growing bone. In one exemplary, non-limiting aspect, the step of isolating an ECM material can comprise isolating SIS from a mammalian tissue source. In this aspect, the method can comprise: incising a wall of a small intestine along a path that is substantially parallel to the longitudinal axis of the small intestine; opening the small intestine along the path of the incision such that the small intestine lies flat on a surface; rinsing the small intestine with sterile saline or other biocompatible fluid; mechanically stripping the SIS of the small intestine from the surrounding smooth muscle and serosal layers and from the tunica mucosa, leaving essentially the submucosal and basement membrane layers. However, it is contemplated that the ECM material can be isolated using any conventional technique, including those described in: U.S. Pat. No. 4,902,508; U.S. Pat. No. 5,275,826; U.S. Pat. No. 5,281,422; U.S. Pat. No. 5,554,389; U.S. Pat. No. 6,579,538; U.S. Pat. No. 6,933,326; U.S. Pat. No. 7,033,611; Voytik-Harbin et al., "Identification of Extractable Growth Factors from Small Intestinal Submucosa," *J. Cell. Biochem.*, Vol. 67, pp. 478-491 (1997); Hodde et al., "Virus Safety of a Porcine-Derived Medical Device: Evaluation of a Viral Inactivation Method," *Biotech. & Bioeng.*, Vol. 79, No. 2, pp. 211-216 (2001); Badylak et al., "The Extracellular Matrix as a Scaffold for Tissue Reconstruction," *Cell & Developmental Biology*, Vol. 13, pp. 377-383 (2002); Robinson et al., "Extracelular Matrix Scaffold for Cardiac Repair," *Circulation*, Vol. 112, pp. I-135-I-143 (2005); Hodde et al., "Effects of Sterilization on an Extracellular Matrix Scaffold: Part I. Composition and Matrix Architecture," *J. Mater. Sci.: Mater. Med.*, Vol. 18, pp. 537-543 (2007); and Hodde et al., "Effects of Sterilization on an Extracellular Matrix Scaffold: Part II. Bioactivity and Matrix Interaction," *J. Mater. Sci.: Mater. Med.*, Vol. 18, pp. 545-550 (2007), each of which is expressly incorporated herein by reference in its entirety.

In an additional aspect, the method can comprise incubating the isolated ECM material for 24 to 48 hours in 0.5-1% Triton X-100/0.5-1% Deoxycholic acid with 5 mM EDTA in Dulbecco's Phosphate Buffered Saline (DPBS) (Lonza Walkersville, Inc.). In this aspect, it is contemplated that flat or sheet-like ECM materials, such as stomach submucosa (SS), small intestinal submucosa (SIS), and bladder submucosa (UBS), can be incubated in a stretched configuration. It is further contemplated that ECM material conduits or other lumenal ECM materials, such as intact ureters, arteries, veins, and small intestines or formed ECM conduits, can be perfused with the various disclosed solutions through soaking and by use of a peristaltic pump.

In a further aspect, after incubation, the method can comprise rinsing the ECM material with DPBS. In this aspect, it is contemplated that the step of rinsing the ECM material can comprise rinsing the ECM material up to six times, including one, two, three, four, five, or six times, with each rinse lasting for about thirty minutes. In an exemplary aspect, it is contemplated that the step of rinsing the ECM material can comprise rinsing the ECM material three times, with each rinse lasting for about thirty minutes.

Optionally, in exemplary aspects, the method can further comprise a second incubation procedure. In these aspects, the second incubation procedure can comprise incubating the ECM material in isotonic tris buffer containing 10-50 µg/mL of RNAase/0.2-0.5 µg/mL DNAase with 5 mM EDTA. It is contemplated that the step of incubating the ECM material in isotonic tris buffer can be performed at a temperature of about 37° C., substantially corresponding to the temperature of a human body. It is further contemplated that the step of incubating the ECM material in isotonic tris buffer can be performed for a period ranging from about 30 minutes to about 24 hours, more preferably, from about 1 hour to about 18 hours, and most preferably, from about 2 hours to about 12 hours. In an additional aspect, the second incubation procedure can further comprise rinsing the ECM material with DPBS. In this aspect, it is contemplated that the step of rinsing the ECM material can comprise rinsing the ECM material three times, with each rinse lasting for about thirty minutes.

In yet another aspect, whether or not the second incubation procedure is performed, the method can comprise storing the ECM material at a temperature ranging from about 1° C. to about 10° C., more preferably, from about 2° C. to about 6° C., and, most preferably, from about 3° C. to about 5° C. In an exemplary aspect, the ECM material can be stored at 4° C.

In an additional aspect, the method can comprise introducing the ECM material into the interior space of the reactor vessel. Optionally, in this aspect, one or more secondary sterilants from the reservoir can be added into the interior space of the reactor vessel along with the ECM material. In these aspects, it is contemplated that the one or more secondary sterilants from the reservoir can be added into the interior space of the reactor vessel before, after, or contemporaneously with the ECM material. It is further contemplated that the temperature control unit can be selectively adjusted to produce a desired temperature within the interior space of the reactor vessel. In a further aspect, the method can comprise equilibrating the pressure within the reactor vessel and the pressure within the storage cylinder. For example, in this aspect, it is contemplated that the pressure within the reactor vessel and the pressure within the storage cylinder can be substantially equal to atmospheric pressure. In yet another aspect, after equilibration of the pressures within the apparatus, the method can comprise operating the magnetic driver to activate the impeller of the reactor vessel. In still a further aspect, the method can comprise selectively introducing the primary sterilant from the storage cylinder into the reactor vessel until a desired pressure within the reactor vessel is achieved. In this aspect, it is contemplated that the step of selectively introducing the primary sterilant into the reactor vessel can comprise selectively activating the air compressor and the booster to increase flow of the primary sterilant into the reactor vessel. In exemplary aspects, the air compressor and booster can be activated to subject the ECM material to supercritical pressures and temperatures, such as, for example and without limitation, the pressures and temperatures necessary to produce supercritical carbon dioxide, for a time period ranging from about 20 minutes to about 60 minutes.

In a further aspect, the method can comprise rapidly depressurizing the reactor vessel. In this aspect, a predetermined amount of primary sterilant, such as, for example and without limitation, supercritical carbon dioxide, can be released from the reactor vessel through the depressurization line. It is contemplated that the primary sterilant can be released from the reactor vessel through opening of the valve coupled to the reactor vessel to thereby reduce the pressure within the reactor vessel. As used herein, the term "rapid depressurization" refers to depressurization of the reactor vessel at a rate greater than or equal to 400 psi/min. For example, it is contemplated that the reactor vessel can be rapidly depressurized at a depressurization rate ranging from about 2.9 MPa/min to about 18.0 MPa/min (about 400 psi/min to about 2,600 psi/min), more preferably, from about 5.0 MPa/min to about 10.0 MPa/min (700 psi/min to about 1,500 psi/min.), and, most preferably, from about 7.0 MPa/min to about 8.0 MPa/min (about 1,000 psi/min to about 1,200 psi/min.). Thus, these rapid depressurizations are significantly greater than the 300 psi/min depressurization rate disclosed in U.S. Pat. No. 7,108,832. Without being bound by any particular theory, it is believed that the disclosed rapid depressurization rates increase the level of decellularization achieved in the ECM material. For example, it is contemplated that the rapid depressurization of a disclosed ECM material can lead to levels of decellularization in the ECM material of greater than about 96%, including 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9%, and 100%.

In exemplary aspects, the method can further comprise the step of incorporating one or more additives into the ECM material. In these aspects, it is contemplated that the one or more additives can be provided in either a powder or a liquid form. In one optional aspect, the step of incorporating the one or more additives can comprise introducing the one or more additives into the reactor vessel during the step of rapidly depressurizing the reactor vessel. In this aspect, it is contemplated that the introduction of the one or more additives can be characterized as a conventional foaming process. In another optional aspect, the step of incorporating the one or more additives can comprise introducing the one or more additives into the reactor vessel after the step of rapidly depressurizing the reactor vessel. In this aspect, it is contemplated that the one or more additives can be added to the ECM material after the rapid depressurization of the reactor vessel has caused the ECM material to swell and/or expand, thereby permitting improved penetration of the additives into the ECM material. It is further contemplated that, in an exemplary aspect, the one or more additives can be added to the ECM material within about thirty minutes after the rapid depressurization of the reactor vessel. In a further optional aspect, the step of incorporating the one or more additives can comprise introducing the one or more additives into the reactor vessel both during and after the step of rapidly depressurizing the reactor vessel. In this aspect, it is contemplated that the one or more additives can be released into the reactor vessel in both a quick manner and a slow, extended manner. In still a further optional aspect, the step of incorporating the one or more additives can comprise introducing the one or more additives into the reactor vessel before the step of rapidly depressurizing the reactor vessel.

The disclosed additives can be incorporated into the ECM material to impart selected properties to the resulting sterilized, acellular ECM composition. Thus, it is contemplated that the one or more additives can be selected to replace or supplement components of the ECM material that are lost during processing of the ECM material as described herein. For example, and as described below, the one or more additives can comprise growth factors, cytokines, proteoglycans, glycosaminoglycans (GAGs), proteins, peptides, nucleic acids, small molecules, drugs, or cells. It is further contemplated that the one or more additives can be selected to incorporate non-native components into the ECM material. For example, the one or more additives can comprise, for example and without limitation, growth factors for recruiting stem cells, angiogenic cytokines, and anti-inflammatory cytokines. It is still further contemplated that the one or more additives can be pharmaceutical agents, such as statins, corticosteroids, non-steroidal anti-inflammatory drugs, anti-inflammatory compounds, anti-arrhythmic agents, and the like. It is still further contemplated that the one or more additives can be nanoparticles, such as, for example and without limitation, silver nanoparticles, gold nanoparticles, platinum nanoparticles, iridium nanoparticles, rhodium nanoparticles, palladium nanoparticles, copper nanoparticles, zinc nanoparticles, and other metallic nanoparticles. It is still further contemplated that the one or more additives can be metallic compounds. In one exemplary aspect, the one or more additives can be selected to pharmaceutically suppress the immune response of a subject following implantation of the resulting ECM composition into the body of a subject.

In one aspect, the one or more additives can comprise one or more growth factors, including, for example and without limitation, transforming growth factor-$\beta$ 1, 2, or 3 (TGF-$\beta$ 1, 2, or 3), fibroblast growth factor-2 (FGF-2), also known as basic fibroblast growth factor (bFGF), vascular endothelial growth factor (VEGF), placental growth factor (PGF), connective tissue growth factor (CTGF), hepatocyte growth factor (HGF), Insulin-like growth factor (IGF), macrophage colony stimulating factor (M-CSF), platelet derived growth factor (PDGF), epidermal growth factor (EGF), and transforming growth factor-$\alpha$ (TGF-$\alpha$).

In another aspect, the one or more additives can comprise one or more cytokines, including, for example and without limitation, stem cell factor, stromal cell-derived factor-1 (SDF-1), granulocyte macrophage colony-stimulating factor (GM-CSF), interferon gamma (IFN-gamma), Interleukin-3, Interleukin-4, Interleukin-10, Interleukin-13, Leukemia inhibitory factor (LIF), amphiregulin, thrombospondin 1, thrombospondin 2, thrombospondin 3, thrombospondin 4, thrombospondin 5, and angiotensin converting enzyme (ACE).

In an additional aspect, the one or more additives can comprise one or more proteoglycans, including, for example and without limitation, heparan sulfate proteoglycans, betaglycan, syndecan, decorin, aggrecan, biglycan, fibromodulin, keratocan, lumican, epiphycan, perlecan, agrin, testican, syndecan, glypican, serglycin, selectin, lectican, versican, neurocan, and brevican.

In a further aspect, the one or more additives can comprise one or more glycosaminoglycans, including, for example and without limitation, heparan sulfate, hyaluronic acid, heparin, chondroitin sulfate B (dermatan sulfate), and chondroitin sulfate A.

In still a further aspect, the one or more additives can comprise one or more proteins, peptides, or nucleic acids, including, for example and without limitation, collagens, elastin, vitronectin, versican, laminin, fibronectin, fibrillin-1, fibrillin-2, plasminogen, small leucine-rich proteins, cell-surface associated protein, cell adhesion molecules (CAMs), a matrikine, a matrix metalloproteinase (MMP), a cadherin, an immunoglobin, a multiplexin, cytoplasmic domain-44 (CD- 44), amyloid precursor protein, tenascin, nidogen/entactin, fibulin I, fibulin II, integrins, transmembrane molecules, and osteopontin.

In yet another aspect, the one or more additives can comprise one or more pharmaceutical agents, including, for example and without limitation, statin drugs, for example, cerevastatin, atorvastatin, fluvastatin, lovastatin, mevastatin, pitavastatin, pravastatin, rosuvastatin, and simvastatin, corticosteroids, non-steroidal anti-inflammatory drugs, anti-inflammatory compounds, anti-arrhythmic agents, antimicrobials, antibiotics, and the like.

In exemplary aspects, the steps of introducing the one or more additives into the reactor vessel can comprise opening the valve to allow the one or more additives to flow from the reservoir into the inlet port. Prior to pressurization, it is contemplated that the one or more additives can be introduced directly into the reactor vessel prior to sealing and/or via the inlet port.

It is contemplated that the disclosed rapid depressurization and repressurization of the reactor vessel, with or without the addition of the one or more additives, can be repeated for any desired number of cycles. It is further contemplated that the cycles of rapid depressurization and repressurization, as well as the introduction of the primary sterilants and/or secondary sterilants and/or additives, can be automatically controlled via a controller that is configured to selectively open and/or close the various valves of the system to achieve desired pressure conditions and cycles.

In some aspects, the disclosed methods can further comprise the step of agitating the contents of the reactor vessel. In these aspects, it is contemplated that the step of agitating the contents of the reactor vessel can comprise periodically agitating the contents of the reactor vessel using a vibrator. It is further contemplated that the agitation of the reactor vessel can be intermittent, continual, or continuous. In exemplary aspects, the step of agitating the contents of the reactor vessel can occur during the step of introducing the primary sterilant into the reactor vessel. It is contemplated that the agitation of the contents of the reactor vessel can enhance the mass transfer of the sterilants and/or additives by eliminating voids in the fluids within the reactor vessel to provide for more complete contact between the ECM material and the sterilants and/or additives. It is further contemplated that the step of agitating the contents of the reactor vessel can comprise selectively adjusting the intensity and duration of agitation so as to optimize sterilization times, temperatures, and pressurization/depressurization cycles.

In a further aspect, after the sterilization and decellularization of the ECM material is complete, the method can further comprise depressurizing the reactor vessel and deactivating the magnetic drive so as to cease movement of the stirring impeller. Finally, the method can comprise the step of removing the resulting sterilized, acellular ECM composition through the top of the reactor vessel.

Methods of Regenerating Heart Valves Using the ECM Material Valve Conduits

Also disclosed herein are methods of regenerating heart valves. In an exemplary aspect, a method of regenerating a semi-lunar valve to replace a defective semi-lunar valve within a heart of a subject is disclosed. In this aspect, and with reference to FIG. 24, it is contemplated that the defective semi-lunar valve is attached at an annulus of an annular region therebetween a ventricle of the heart of the subject and an artery of the subject. As used herein, the term "semi-lunar valve" can refer to either a pulmonary valve or an aortic valve within the heart of the subject. It is contemplated that, if the defective semi-lunar valve is a pulmonary valve, then the defective semi-lunar valve is attached at an annulus of an annular region between the right ventricle of the heart of the subject and the pulmonary artery of the subject. It is further contemplated that, if the defective semi-lunar valve is an aortic valve, then the defective semi-lunar valve is attached at an annulus of an annular region between the left ventricle of the heart of the subject and the aorta of the subject.

In one aspect, a disclosed method of regenerating a semi-lunar valve can comprise removing the defective semi-lunar valve from the heart of the subject, thereby exposing the annular region. In this aspect, it is contemplated that the step of removing the defective semi-lunar valve can optionally comprise removing a portion of an artery that was coupled to the defective semi-lunar valve, such as an aorta or a pulmonary artery. It is further contemplated that the step of removing the defective semi-lunar valve can optionally comprise removing the annulus of the annular region.

It is contemplated that the step of removing the defective semi-lunar valve can further comprise placing the subject on cardiopulmonary bypass. It is further contemplated that the step of removing the defective semi-lunar valve can further comprise arresting and/or fibrillating the heart of the subject and exposing the defective valve through an incision in the heart of the subject. Alternatively, the defective valve can be accessed percutaneously using known methods.

In an additional aspect, a disclosed method of regenerating a semi-lunar valve can further comprise implanting an ECM material valve conduit, such as those disclosed herein. In this aspect, and as further disclosed herein, the ECM material valve conduit can define a lumen and have an inlet portion and an outlet portion. In a further aspect, the step of implanting an ECM material valve conduit can comprise securing the inlet portion of the ECM material valve conduit to the annular region and securing the outlet portion of the ECM material valve conduit to the artery of the subject such that the inlet portion is positioned proximate the annular region. In this aspect, it is contemplated that the ECM material valve conduit can be secured to the annular region and/or the artery using any conventional surgical attachment means, including, for example and without limitation, non-absorbable sutures, absorbable sutures, surgical pastes, surgical glues, staples, and the like. Optionally, in one aspect, the ECM material valve conduit can be secured to the annular region before it is secured to the artery. In this aspect, it is contemplated that, after the ECM material valve conduit has been properly secured to the annulus, the length of the ECM material valve conduit can be trimmed as necessary to eliminate any excess length while retaining adequate tissue for proper attachment of the ECM material valve conduit to the artery. Alternatively, in another aspect, the ECM material valve conduit can be secured to the artery before it is secured to the annular region. In this aspect, it is contemplated that, after the ECM material valve conduit has been properly secured to the artery, the length of the ECM material valve conduit can be trimmed as necessary to eliminate any excess length while retaining adequate tissue for proper attachment of the ECM material valve conduit to the annular region.

In exemplary aspects, it is contemplated that one or more pledgets can be added to the outer wall of the ECM material valve conduit at locations proximate the attachment of the ECM material valve conduit to the annular region and/or the artery. In these aspects, it is contemplated that the pledgets can be configured to shield the ECM material valve conduit from direct contact with the sutures between the ECM material valve conduit and the annular region and/or artery, thereby minimizing the risk of the suture cutting through the ECM material valve conduit and providing additional structural integrity to the ECM material valve conduit. It is contemplated that any conventional pledget, such as, for example and without limitation, Teflon® pledgets, can be employed for these purposes. In an exemplary aspect, it is contemplated that the one or more pledgets can comprise at least one ECM material. It is contempletried that the one or more pledgets can have any suitable shape and dimensions. However, in exemplary aspects, it is contemplated that the pledget can comprise a substantially rectangular sheet having a length ranging from about 2 mm to about 4 mm and a width ranging from about 2 mm to about 4 mm.

After the ECM material valve conduit is properly secured to the annular region and to the artery, and after any necessary trimming or sculpting of the ECM material valve conduit has been completed, the heart of the subject can be closed as necessary and the heart of the subject can be restarted.

It is further contemplated that anti-coagulant and/or anti-thrombotic agents and/or therapies can be delivered to the subject before, during, and/or after the ECM material valve conduit is properly secured to the annular region and to the artery. It is contemplated that these agents and/or therapies can prevent thrombus formation on the leaflets of the regenerated valve in the subject.

In additional aspects, and as shown in FIG. 4, the inner layer of a disclosed ECM material valve conduit can comprise leaflet-promoting portions and commissure-promoting portions, and the outer layer of the disclosed ECM material valve conduit can comprise sinus-promoting portions. In these aspects, it is contemplated that the leaflet-promoting portions can regenerate a plurality of leaflets (i.e., three leaflets) of a replacement semi-lunar valve proximate the annulus. It is further contemplated that the sinus-promoting portions of the outer layer of the ECM material valve conduit can fuse with the inner layer of the ECM material valve conduit to regenerate sinus portions of the replacement semi-lunar valve. It is still further contemplated that the commissure-promoting portions of the ECM material valve conduit can fuse with the outer layer of the ECM material valve conduit to regenerate commissures of the replacement semi-lunar valve. FIGS. 7-11 display regeneration of a pulmonary valve following implantation of an exemplary ECM material valve conduit according to the methods described herein.

It is contemplated that, following implantation of the ECM material valve conduit as disclosed herein, the implanted ECM material valve conduit can attract stem cells of the subject that will remodel the ECM material to form the replacement semi-lunar valve. The stem cells can remodel the inner layer of the ECM material valve conduit and the supporting arterial wall into leaflets and commissures of the replacement semi-lunar valve and can remodel the outer layer of the ECM material valve conduit into sinus portions of the replacement semi-lunar valve. During this remodeling process, it is contemplated that the implanted ECM material valve conduit can provide normal valvular function. It is further contemplated that the implanted ECM material valve conduit can be gradually degraded and replaced with host tissue that is indistinguishable (i.e., identical or substantially identical) to normal, native tissue.

EXPERIMENTAL EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example One

An ECM material valve conduit was constructed as disclosed herein. A sheep was anesthetized. The left chest of the sheep was opened, and then the heart of the sheep was exposed. The sheep was placed on cardiopulmonary bypass to support the sheep while the pulmonary valve and portions of the pulmonary artery were excised. During the excision, the pulmonary valve (including leaflets) and the annulus at which the pulmonary valve was secured were removed. Additionally, several centimeters of the pulmonary artery distal to the pulmonary valve complex were removed. The ECM material valve conduit was then sutured into place, with the inlet portion sutured to the heart and the outlet portion sutured to the remaining pulmonary artery.

Figure 7:
FIGS. 7-11 are images of a regenerated pulmonary valve taken at three months following implantation of an extracellular matrix material valve conduit for purposes of regenerating the pulmonary valve in the heart of the sheep.
Figure 8:
Figure 9:
Figure 10:
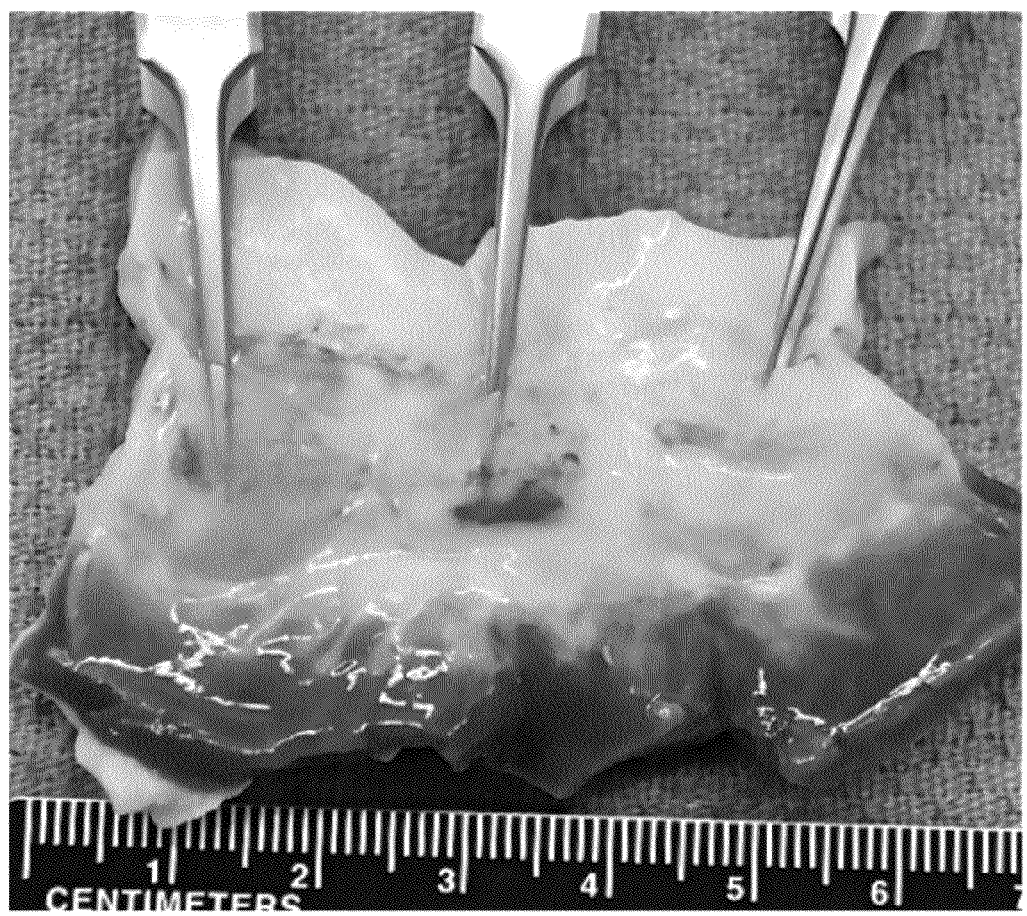
Figure 11:

FIGS. 7-14 depict findings at harvest after the conduit had been in the animal for three months of remodeling. FIG. 7 demonstrates how the ECM material valve conduit has taken on the appearance of a normal pulmonary artery. FIG. 8 shows the remodeled leaflets from the perspective of the distal, pulmonary artery. FIG. 9 shows the inlet portion of the ECM material valve conduit from the perspective of the heart and the ventricular side of the leaflets. FIG. 10 shows the three leaflets with the conduit opened longitudinally. FIG. 11 shows the three leaflets from the perspective of the pulmonary artery with the ECM material valve conduit opened.

Figure 12:
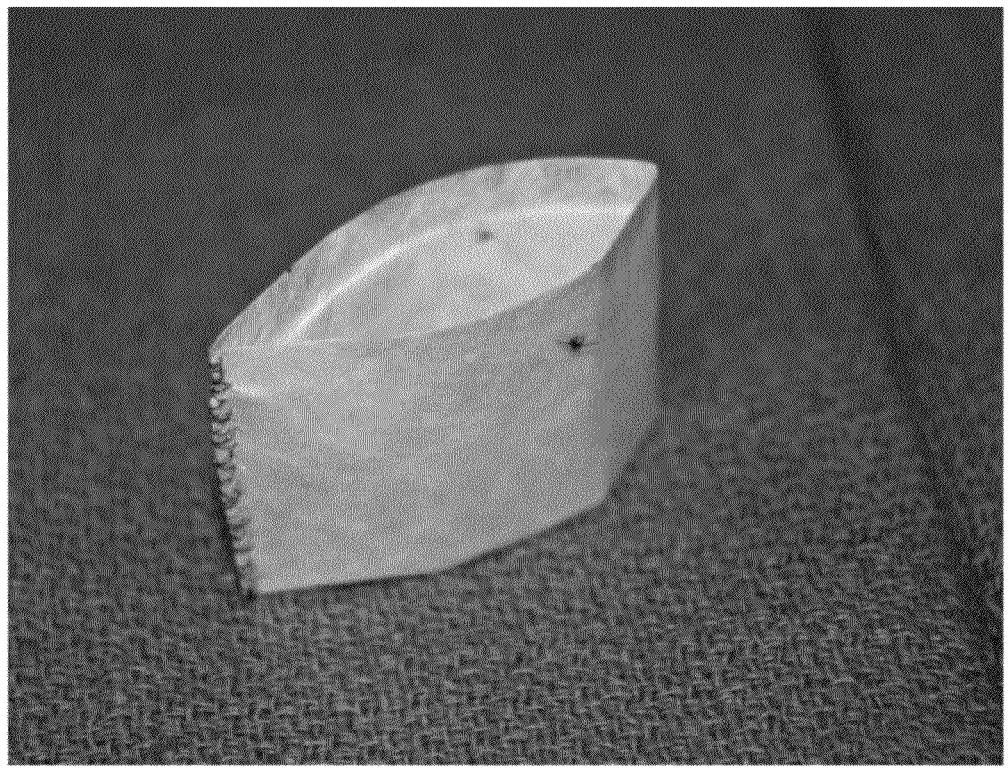
FIGS. 12-14 are images depicting exemplary extracellular matrix valve conduits, as described herein.
Figure 13:
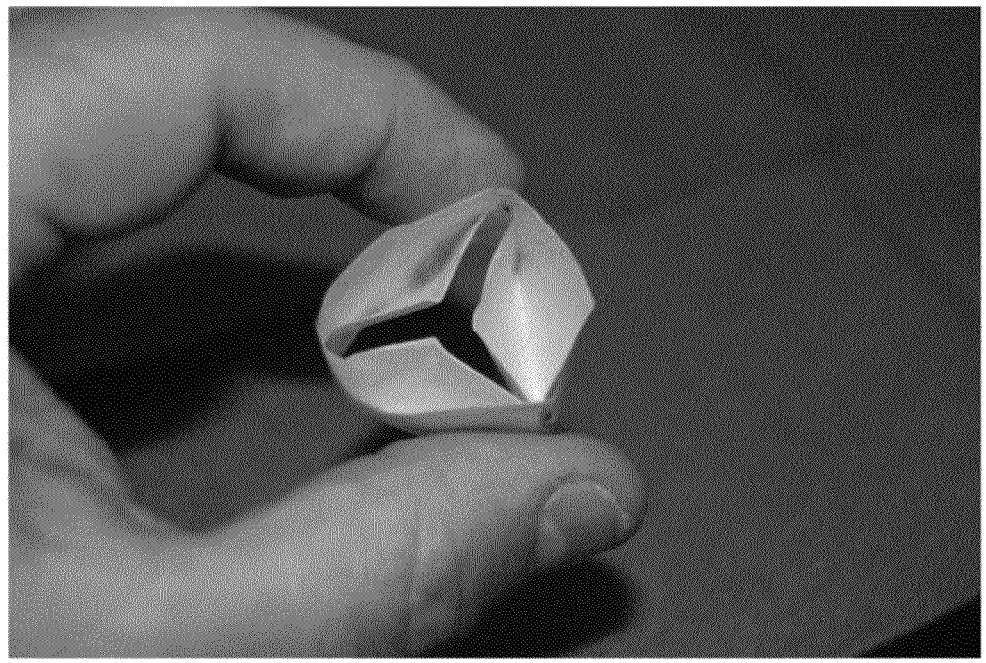
Figure 14:

FIGS. 12-14 show exemplary ECM material valve conduits prior to implantation. FIG. 12 shows a manufactured ECM material valve conduit in a closed position, while FIG. 13 shows the ECM material valve conduit in an open position. FIG. 14 shows an exemplary ECM material valve conduit that has been hydrated in sterile water prior to implantation.

Example Two

Figure 15:
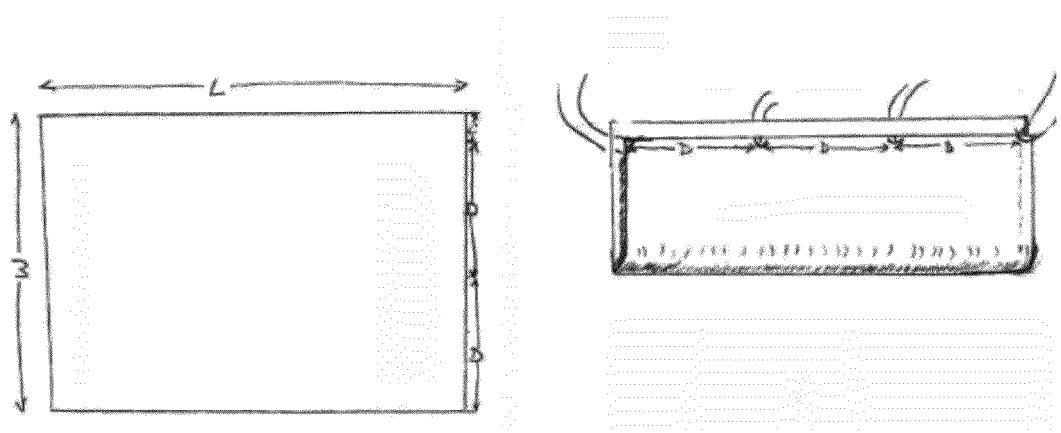
FIGS. 15-23 are sketches and images associated with a patient study that was performed using concepts as described herein.
Figure 16:
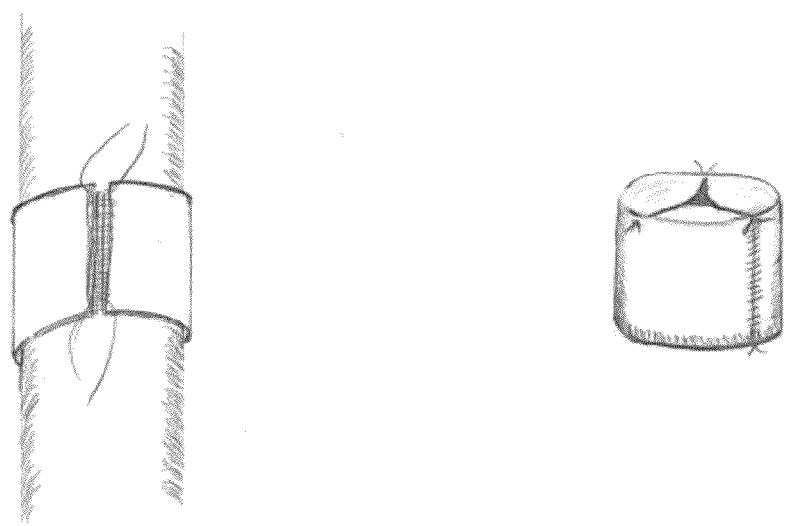
Figure 23:
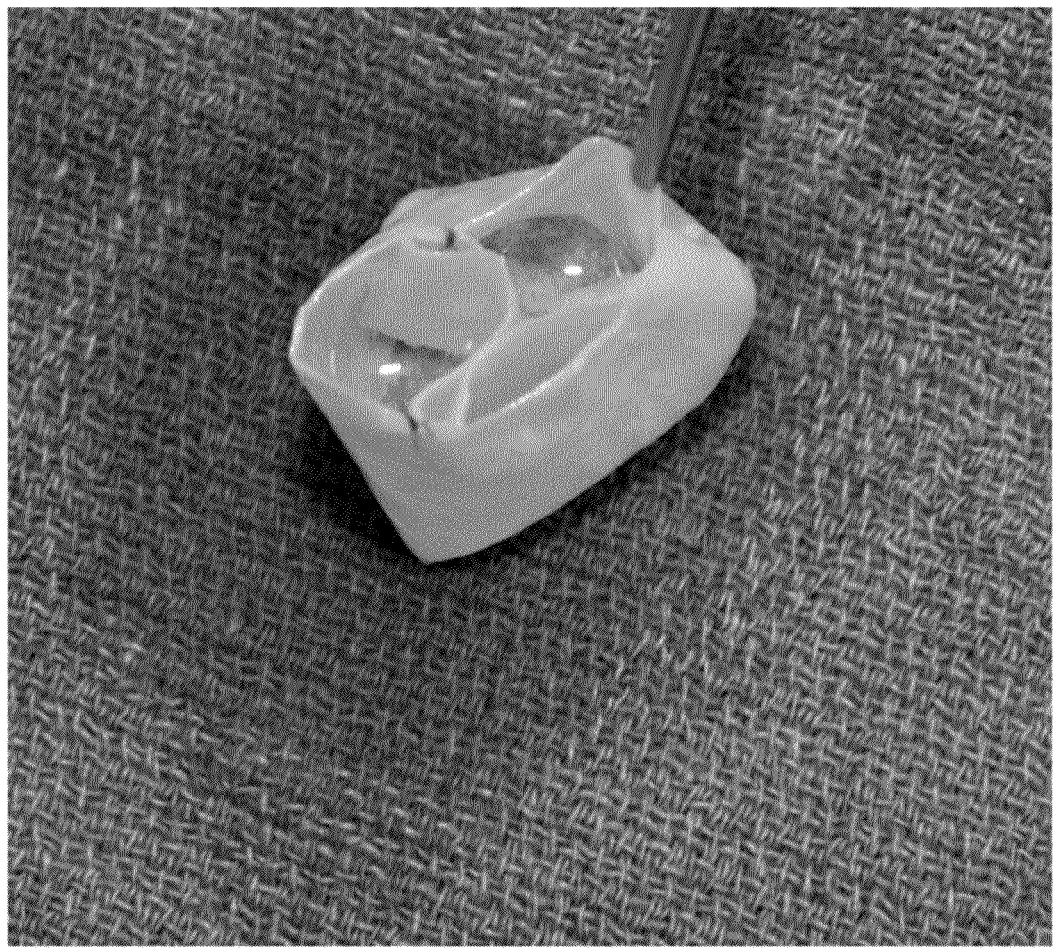

As depicted in FIGS. 15-16, a large rectangular patch of pericardium was used to construct a tri-leaflet conduit through a process of folding and suturing. The patch was rolled over an appropriately sized dilator. After the patch was rolled onto the dilator, lengthwise sutures were used to form an ECM conduit. This ECM conduit, which is shown in FIG. 23, was used to establish right ventricular to pulmonary continuity in a congenital reconstructive procedure performed on a patient.

The graft material came as a dried sheet in an easily stored packet. The sheet had the dimensions of 7 cm×10 cm. The sheet was prepared in saline solution for ten minutes.

The patient was a 12 year-old female with a bicuspid aortic valve causing severe aortic stenosis. Approximately 18 months earlier, a retrograde balloon valvuloplasty had been performed. Subsequently, the patient developed severe aortic regurgitation with progressive left ventricular dilatation. The left ventricular end diastolic dimension was 6.2 cm, and the patient was symptomatic with dyspnea on exertion.

With the patient anesthetized and draped for surgery, the ECM conduit was hydrated in normal saline solution for ten minutes and then trimmed to allow for a final conduit size of 20 mm. The size of the conduit was determined by preoperative echocardiographic measurements of the patient's pulmonary valve size and then up-sizing to create a valve Z score of 2. A 20 mm conduit was created by trimming the rectangular patch of pericardium to the dimensions of 65 mm×45 mm. With reference to FIG. 15, the length (L) and width (W) of the patch were determined by the formulas:

$$L = D^* \pi; \text{ and}$$

$$W = (2^*D) + C,$$

where D is the desired diameter of the conduit and C is the cuff length, which corresponds to the portion of the conduit that is to be attached to the pulmonary artery of the patient.

After preparation of the conduit, a Ross procedure, using a full root replacement technique with continuous monofilament suture for each anastomosis was performed. The procedure was performed at 32° C., using bi-caval cannulation and intermittent retrograde blood cardioplegia every 15 to 20 minutes. The conduit implantation was performed using a continuous monofilament suture after the proximal aortic root reconstruction and before the distal aortic suture line was completed. The distal conduit anastomosis was completed before the proximal conduit anastomosis. Both anastomoses were performed using continuous 5-0 prolene sutures before the aortic cross clamp was removed. The branch pulmonary arteries were mobilized extensively to allow for a tension-free proximal anastomosis and to avoid the use of additional patch material proximally. The conduit was created with a 5 mm distal cuff extension. After release of the cross clamp, the heart of the patient regained vigorous contractility with minimal inotropic support.

Figure 17:
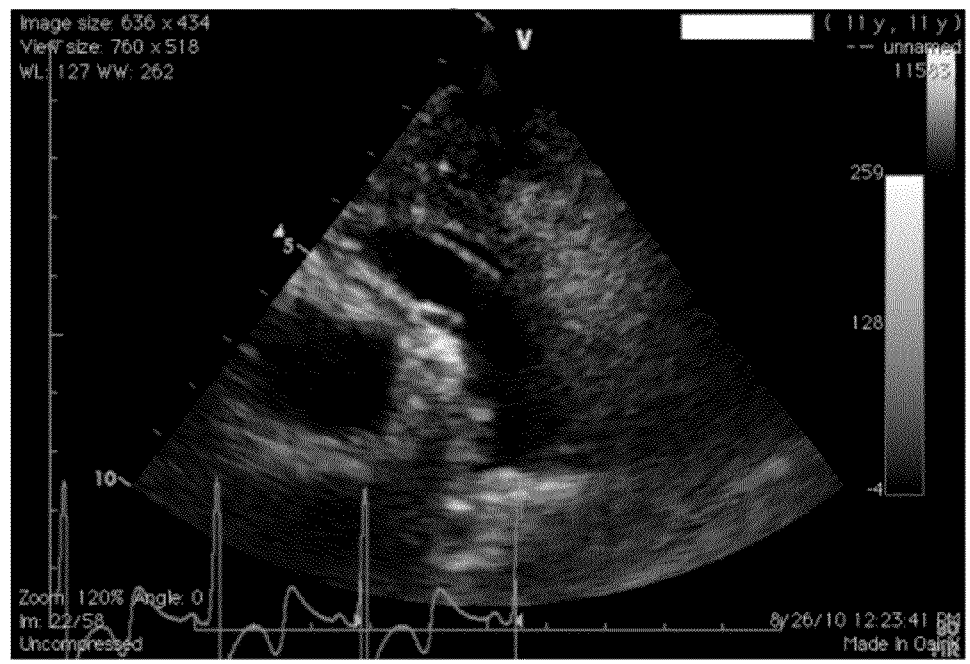
Figure 18:
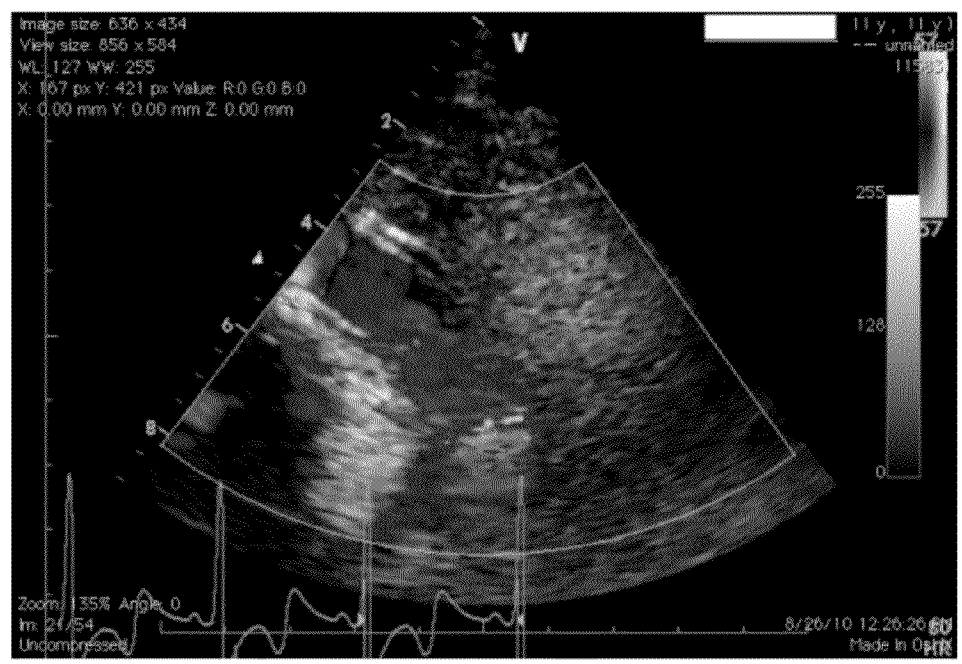
Figure 19:
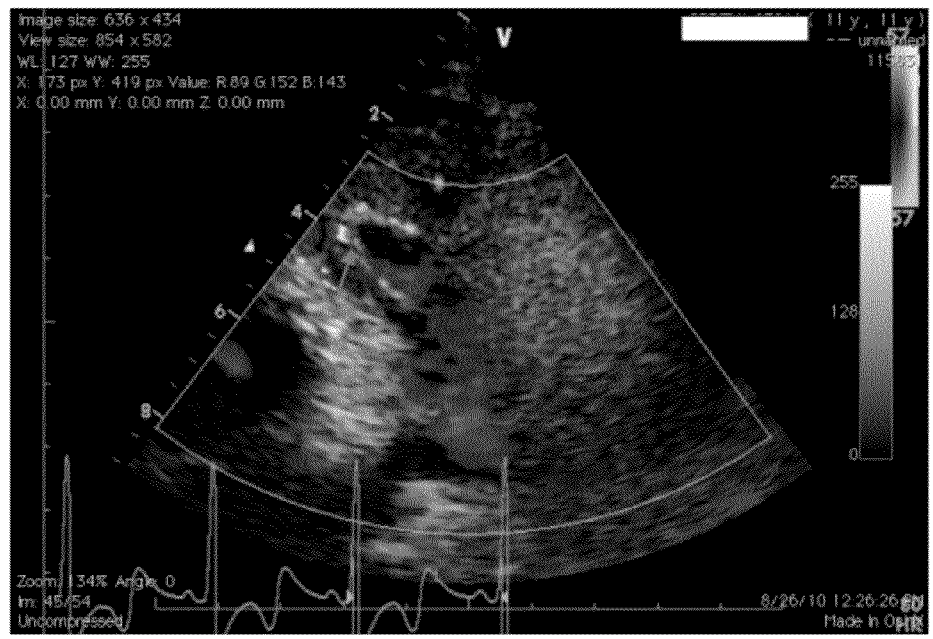

The procedure was completed and the patient was easily separated from bypass. The patient's cardiac performance and hemostasis were satisfactory. She was awakened and extubated in the operating room. Her recovery was uneventful and after one day in the intensive care unit was transferred to the ward. Five days after the operation, she underwent a complete echocardiogram prior to hospital discharge. The results of this are shown in FIGS. 17-19. Six days after the operation, she was discharged from the hospital in excellent condition.

Initial follow-up echocardiogram studies were obtained one month after hospital discharge. These echocardiogram studies showed no stenosis or insufficiency of the conduit and showed mild autograft insufficiency with well-preserved left ventricular function. The ventricular dimensions of the patient returned to normal. The patient did not show any symptoms and was taking aspirin and an ACE inhibitor. The echocardiograms indicated that the patient was in New York Heart Association (NYHA) heart failure classification 1.

Figure 20:
Figure 21:
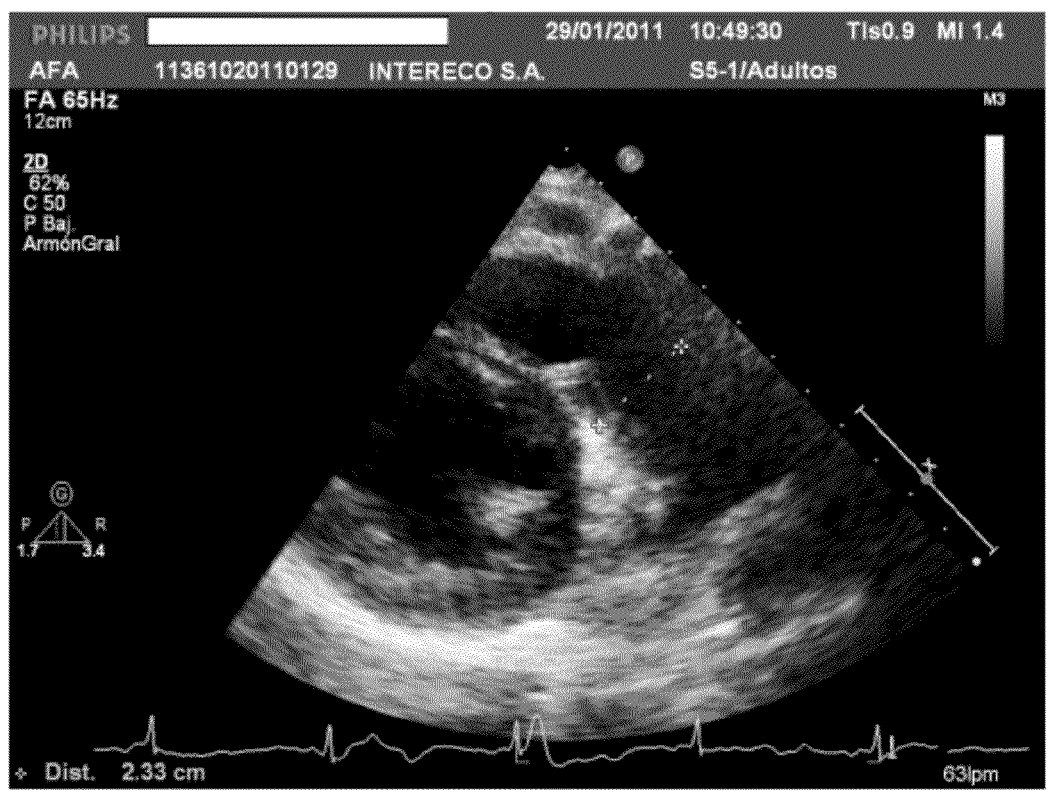
Figure 22:

Subsequent follow-up echocardiogram studies were obtained five months after hospital discharge. At the time of these follow-up echocardiogram studies, the patient had gained weight and had returned to full physical activity without limitations. Auscultation revealed no systolic or diastolic murmurs. The follow-up echocardiograms, which are shown in FIGS. 20-22, indicated that the patient remained in NYHA classification 1. The echocardiograms also demonstrated that the patient had completely normal right and left ventricular function as well as normal conduit function. Minor conduit insufficiency was observed, and leaflet mobility was unchanged from the echocardiograms recorded at five days after the operation. Peak echo velocity within the conduit was 2 meters/second and color flow did not exhibit any turbulence. The left ventricular end diastolic diameter was measured as 4.0 cm.

Example Three

Figure 24:
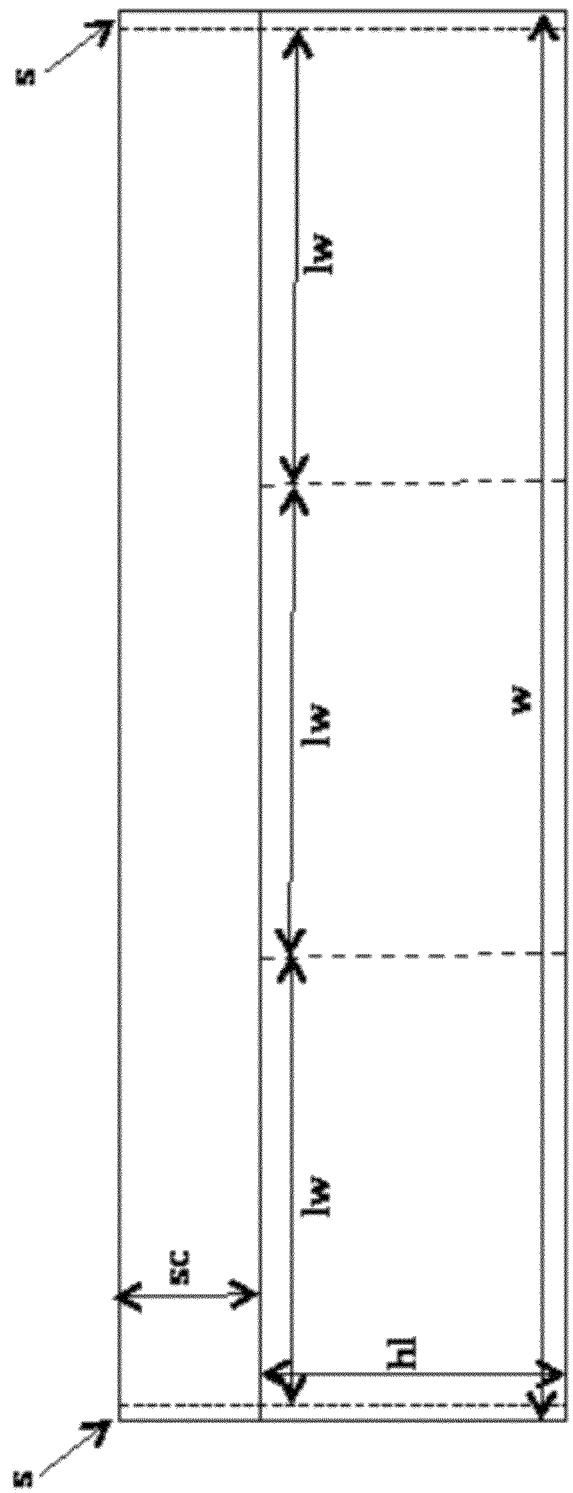
FIG. 24 is a diagram of an exemplary extracellular matrix valve conduit construction, which depicts a sewing seam allowance (s), a sewing cuff (sc), a leaflet height (h1), a leaflet width (1 w), and an ECM sheet width (w).

Various measurements of exemplary ECM material valve conduits, as depicted in FIG. 24, are provided in Table 1 below:

TABLE 1

| Annulus D, mm | Width (w), mm | height, mm | Sewing Cuff height (sc), mm | height leaflet (hl)s, mm | leaflet width (lw), mm | side sewing allowance (s), mm |
|---|---|---|---|---|---|---|
| 18 | 59.5 | 38.8 | 10.0 | 14.4 | 18.8 | 1.5 |
| 20 | 65.8 | 42.0 | 10.0 | 16.0 | 20.9 | 1.5 |
| 22 | 72.1 | 45.2 | 10.0 | 17.6 | 23.0 | 1.5 |
| 24 | 78.4 | 48.4 | 10.0 | 19.2 | 25.1 | 1.5 |
| 26 | 84.7 | 51.6 | 10.0 | 20.8 | 27.2 | 1.5 |
| 28 | 91.0 | 54.8 | 10.0 | 22.4 | 29.3 | 1.5 |
| 30 | 97.2 | 58.0 | 10.0 | 24.0 | 31.4 | 1.5 |

Example Four

In vitro mechanical evaluation was performed on the seam of exemplary ECM material valve conduits as described herein. The maximum tensile break force for the sewn seam was found to be 52.1±14.1 N (11.7±3.16 $lb_f$), with a minimum and maximum of 34.8 N (7.82 $lb_f$) and 72.3 N (16.25 $lb_f$), respectively. The tensile force, ball burst, and suture pull-out forces for exemplary 4-ply ECM material valve conduits as described herein was determined to be 19.35±5.51 N (4.35±1.24 $lb_f$), 126.6±30.2 N (6699±1598 mmHg), and 11.12±2.08 N (2.50±0.47 $lb_f$), respectively. These results indicate that the structural integrity of the ECM material valve conduits described herein are more than adequate to meet the force requirements of the pulmonary valve in the low-pressure environment of the right heart.

Example Five

Figures 25A, 25B, 25C:
FIG. 25(a) depicts the ECM material valve conduit during opening.
FIG. 25(b) depicts the ECM material valve conduit during closure.
FIG. 25(c) depicts the ECM material valve conduit radially at closure.
Figure 26A:
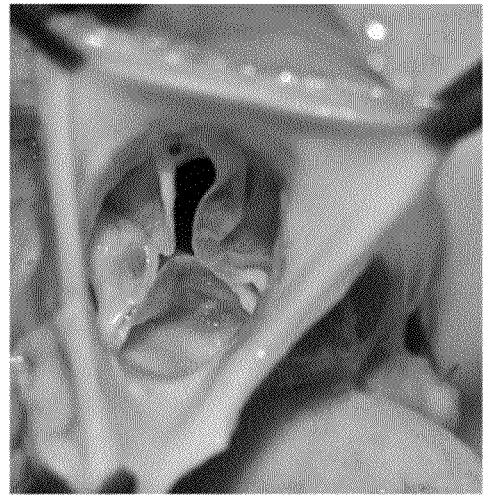
FIG. 26(a) shows regeneration at 3 months.
Figure 26B:
FIG. 26(b) shows regeneration at 5 months.
Figure 26C:
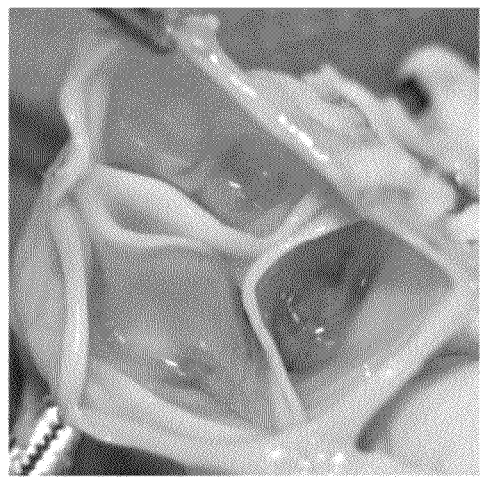
FIG. 26(c) shows regeneration at 6 months.
Figure 26D:
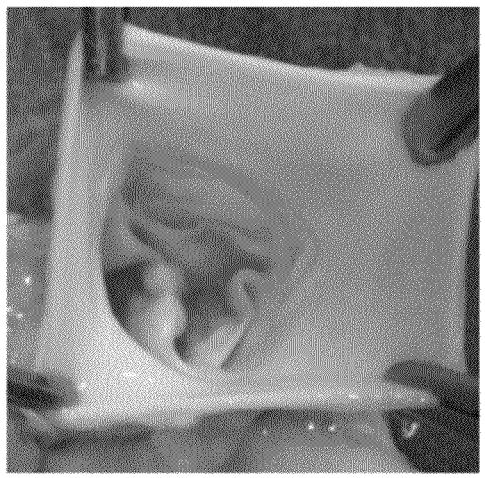
FIG. 26(d) shows regeneration at 12 months.

Exemplary ECM material valve conduits were evaluated in an animal study model. The ECM material valve conduits were implanted in a pulmonary valve position following removal of the native pulmonary valve. The results have shown physiologically normal hemodynamic results for the ECM material valve conduits in the immediate postoperative period prior to tissue remodeling and also out to twelve months. At 12 months, much of the ECM was remodeled into the animal's native tissue. Echocardiography has shown good hemodynamics for the regenerated valves out to 12 months with complete coaptation of the leaflets and no leaflet prolapse (FIG. 25).

Gross necropsy and histology results showed appropriate remodeling of the valve with increased replacement by host tissue at each subsequent time point. The replacement valves appeared grossly similar to the native valve that was replaced. FIG. 26 shows 3-, 5-, 6-, and 12-month explants from sheep implanted with the ECM material Pulmonary Valve Conduit as part of the non-GLP study. These images demonstrated the progressive remodeling that is occurring over time in the sheep. As shown, at the 3-month time point (FIG. 26(a)), remodeling has already occurred at the valve annulus and is extending to the leaflets to regenerate apparently normal valve tissue. At 12 months (FIG. 26(d)), the leaflets are remodeled and appear similar to native valve tissue.

H&E histology of the explanted ECM Pulmonary Valve Conduit after 3, 5, 6 and 12 months was analyzed. Cells were distributed throughout the valve and even into the tip of the leaflet by 3 months, and by 6 months the remodeled tissue has formed a three-layer structure similar to the native valve tissue with a ventricularis, spongiosa, and fibrosa.

Example Six

In exemplary applications of the disclosed sterilization and decellularization methods, selected tissues were harvested and rinsed in sterile saline. The selected tissues were then frozen for 24 hours. The frozen tissues were thawed in cold hypotonic tris buffer on ice with 5 mM ethylenediaminetetraacetic acid (EDTA). An extracellular matrix material was then isolated from each selected tissue, as described herein.

The isolated extracellular matrix materials were incubated for 24 to 48 hours in 0.5-1% Triton X-100/0.5-1% Deoxycholic acid with 5 mM EDTA in Dulbecco's Phosphate Buffered Saline (DPBS) (Lonza Walkersville, Inc.). Flat extracellular matrix materials, such as stomach submucosa (SS), small intestinal submucosa (SIS), and bladder submucosa (UBS), were incubated in a stretched configuration. Tubular extracellular matrix materials, such as ureters, arteries, veins, and tubular SIS, were perfused with the solutions through soaking and by use of a peristaltic pump.

After incubation, each extracellular matrix material was rinsed three times with DPBS. Each rinsing with DPBS lasted 30 minutes. Some extracellular matrix materials were then incubated for 2 to 12 hours at 37° C. in isotonic tris buffer containing 10-50 µg/mL of RNAase/0.2-0.5 µg/mL DNAase with 5 mM EDTA. Following this incubation step, the extracellular matrix materials were again rinsed three times with DPBS. Each rinsing with DPBS lasted 30 minutes. The extracellular matrix materials were stored at 4° C.

Within 48 hours of storage, the extracellular matrix materials were processed in supercritical carbon dioxide as disclosed herein for 20-60 minutes at temperatures at or greater than 31.1° C. and pressures at or greater than 1,071 psi. After this sterilization step, the extracellular matrix materials were rapidly depressurized at a rate of 2.7 MPa/10 sec. (391.6 psi/10 sec.) for a minute and 19 seconds. During this time, the pressure applied to the extracellular matrix materials rapidly decreased from 9.9 MPa to 0.69 MPa.

The extracellular matrix materials were then processed in supercritical carbon dioxide and peracetic acid (PAA) as disclosed herein for 30 minutes to 6 hours to achieve terminal sterilization. In this processing step, the pressure applied to the extracellular matrix materials was increased to 9.9 MPa. The resulting sterilized, acellular extracellular matrix materials were then packaged in Tyvek® (E.I. du Pont de Nemours & Company) pouches that were sealed within plastic pouches to prevent fluid leakage.

Table 2 summarizes the sterilization and decellularization of porcine ureter, bovine pericardium, and porcine mesothelium.

TABLE 2

| Material | Triton X-100 Conc. | Deoxycholic Acid Conc. | TX-100/ Deoxy bincuation | RNAse/ DNAse incubation | Supercritical $CO_2$/PAA time |
|---|---|---|---|---|---|
| Porcine ureters | 0.5% | 0.5% | 24 hours | 2 hours | 120 minutes |
| Bovine pericardium | 0.5% | 0.5% | 24 hours | 2 hours | 180 minutes |
| Porcine mesothelium | 0.5% | 0.5% | 24 hours | 2 hours | 120 minutes |

Example Seven

The DNA content of ECM material samples was measured as an indicator of decellularization of the respective ECM material samples using various sterilization and decellularization techniques. The measured DNA content was evaluated with a pico green assay in which DNA was labeled with a fluorescent label that was detected with a spectrophotometer. The measured DNA content was normalized by the dry weight of the samples. DNA content was measured and evaluated for the following treatment groups: (1) Lyophilized, non-sterile SIS; (2) Ethylene Oxide (EtO)-sterilized SIS; (3) Lyophilized, non-sterile SIS that was sterilized through a 60 minute treatment with PAA and supercritical $CO_2$, as disclosed herein; (4) Lyophilized, non-sterile SIS that was sterilized through a 20 minute treatment with PAA and supercritical $CO_2$, as disclosed herein; and (5) Raw, unprocessed SIS.

Figure 27:
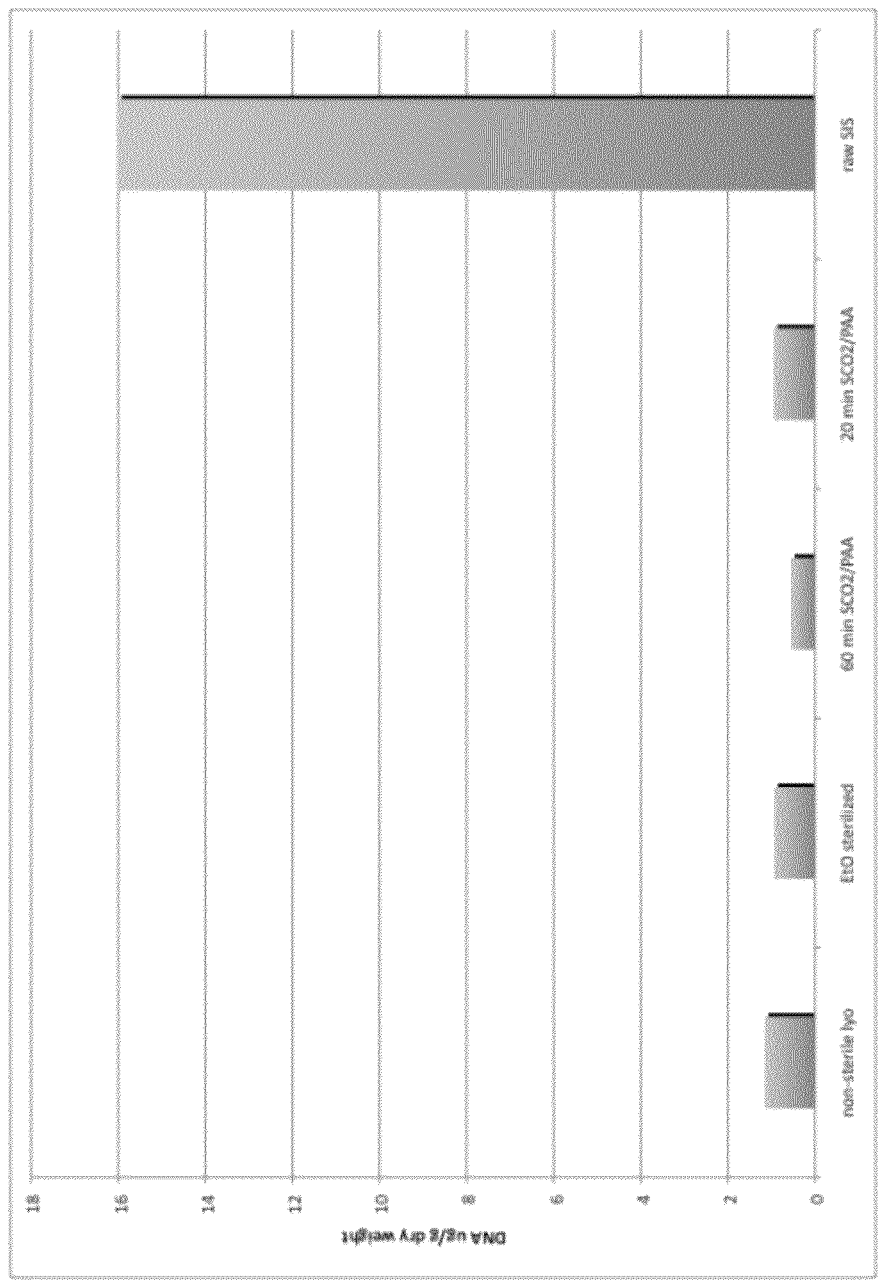
FIGS. 27-28 depict the results of an experiment in which DNA content was measured for small intestinal submucosa (SIS) compositions following various sterilization methods, including the sterilization methods described herein.
Figure 28:
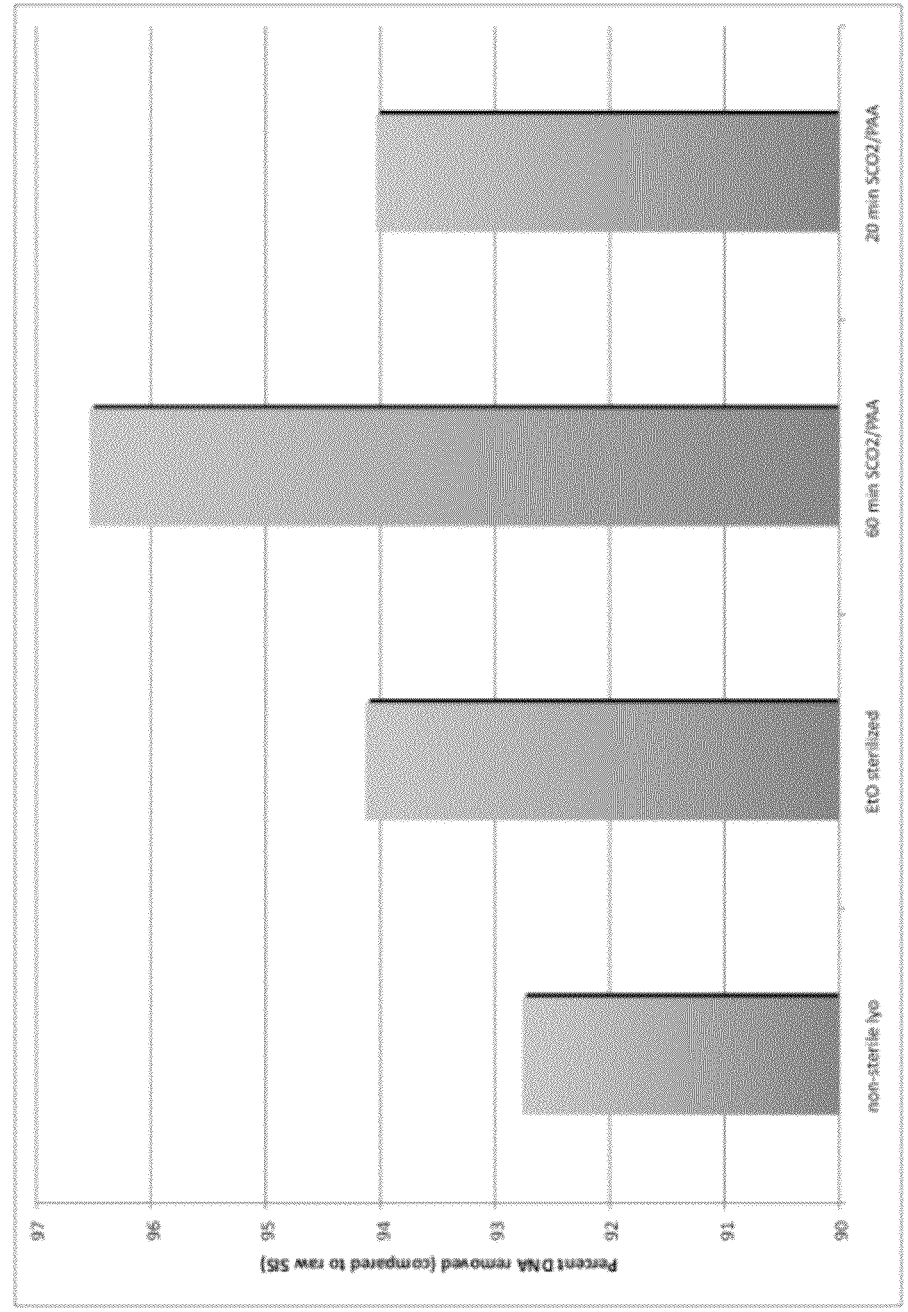

FIG. 27 shows the total DNA content for the respective samples, as normalized by dry weight. FIG. 28 shows the percent of DNA that was removed from each respective sample, as compared to raw, unprocessed SIS. These results indicated that by sterilizing the non-sterile SIS using a 60 minute treatment with PAA and supercritical $CO_2$, as disclosed herein, over 96% of the DNA found in raw SIS was removed, as compared to only 94% when the SIS was sterilized by EtO and only 93% when the SIS was not sterilized by any method.

Example Eight

Ureters were processed with a gentle detergent (0.5% Triton X-100/0.5% Sodium Deoxycholate in 5 mM EDTA in DPBS) for 24 hours and then rinsed three times in DPBS as disclosed herein. After this pretreatment, the ureters were decellularized and sterilized using rapid depressurization and treatment with PAA and supercritical $CO_2$, as disclosed herein. Hematoxylin and Eosin (H&E) Stains were prepared for one sample ureter at the following stages of treatment: (A) native ureter; (B) pretreated ureter; and (C) pretreated ureter with rapid depressurization and treatment with PAA and supercritical $CO_2$, as disclosed herein. These stains indicated that DNA content was significantly reduced with rapid depressurization.

Example Nine

Figure 29:
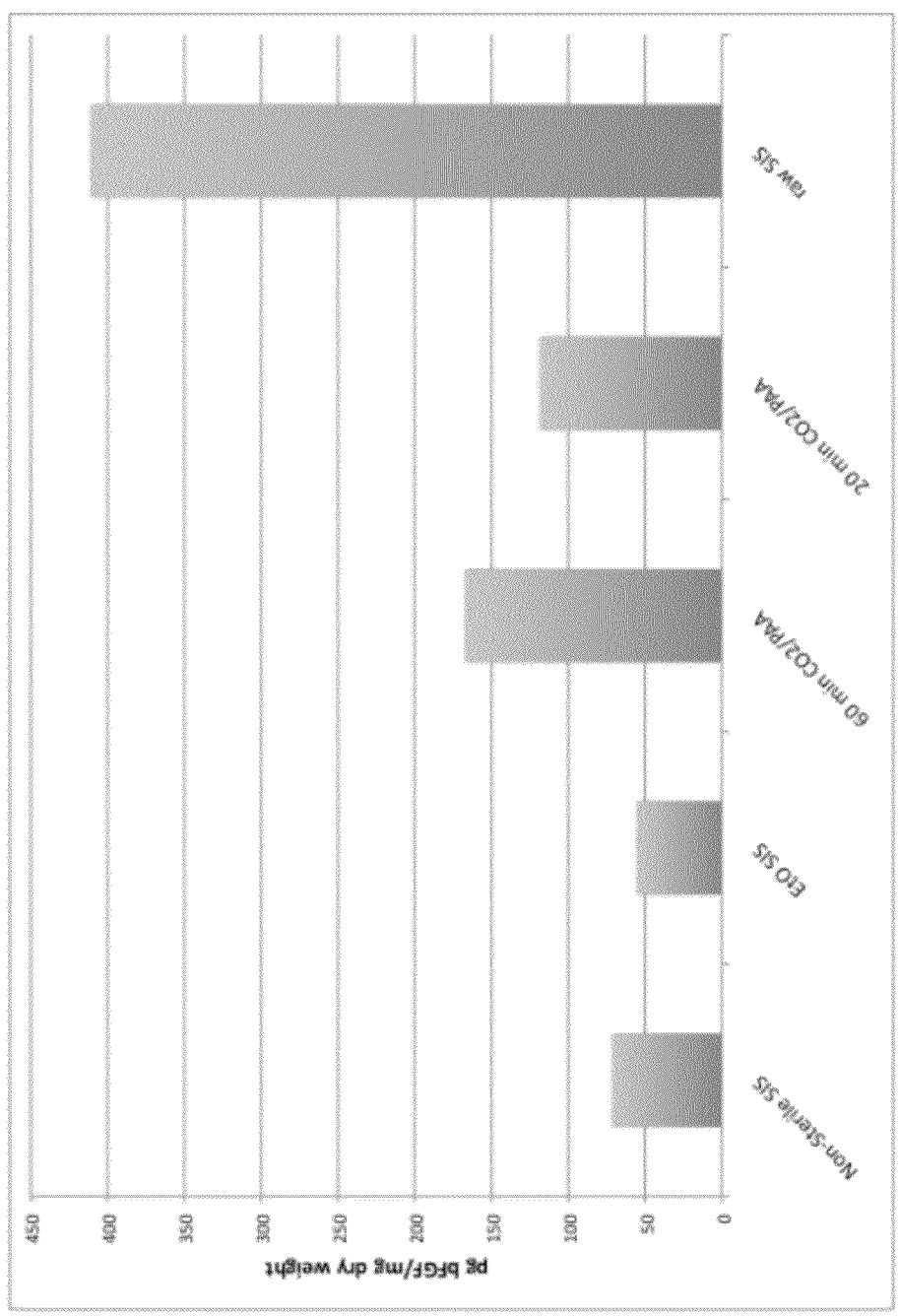
FIGS. 29-30 depict the results of an experiment in which native growth factor content was measured for SIS compositions following various sterilization methods, including the sterilization methods described herein.
Figure 30:
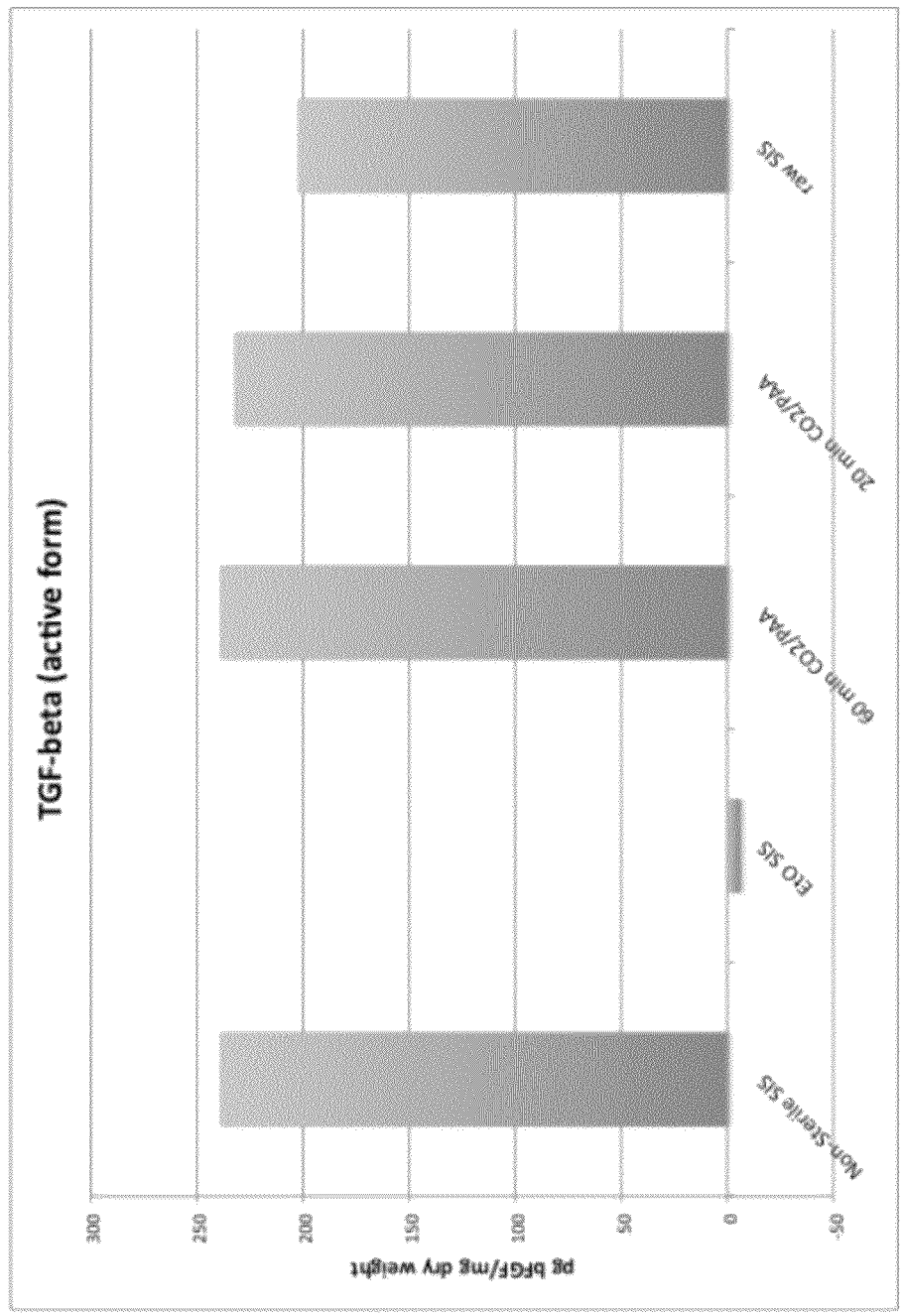

The growth factor content of ECM material samples was measured. Enzyme-linked immunosorbent (ELISA) assays were performed on the ECM material samples to quantify the content of bFGF and the active form of TGF-β in each respective sample. The following treatment groups were evaluated: (1) Lyophilized, non-sterile SIS; (2) Ethylene Oxide (EtO)-sterilized SIS; (3) Lyophilized, non-sterile SIS that was sterilized through a 60 minute treatment with PAA and supercritical $CO_2$, as disclosed herein; (4) Lyophilized, non-sterile SIS that was sterilized through a 20 minute treatment with PAA and supercritical $CO_2$, as disclosed herein; and (5) Raw, unprocessed SIS. The bFGF content and TGF-β content measurements were normalized by dry weight of each respective sample. These results are shown in FIGS. 29 and 30. These results indicated that the concentration of both growth factors was reduced by exposure to EtO. However, the concentration of the growth factors was not affected by sterilization with PAA and supercritical $CO_2$.

Example Ten

Figure 31:
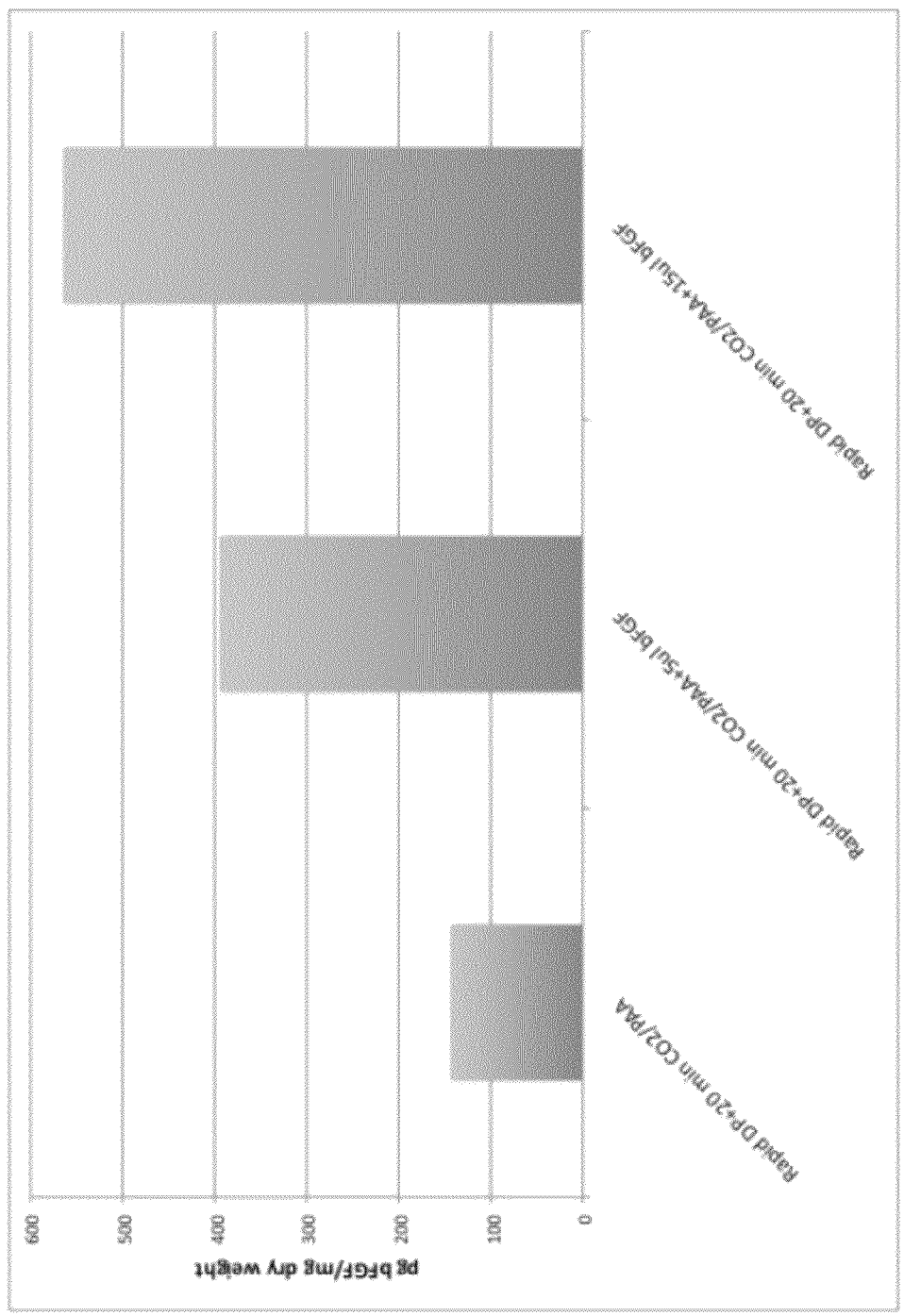
FIG. 31 depicts the results of an experiment in which bFGF was incorporated into SIS compositions during rapid depressurization, as described herein.

Using the methods disclosed herein, supercritical $CO_2$ was used as a primary sterilant and as a carrier for adding bFGF into SIS sheets. First, the respective SIS sheets were placed into Tyvek® pouches along with varying amounts of bFGF. The pouches were exposed to supercritical $CO_2$ for 60 minutes at 9.6 MPa. The pouches were rapidly depressurized at a rate of 7.20 MPa/min. Samples were directly processed in 16 mL PAA in supercritical $CO_2$ for 20 minutes. The following treatment groups were evaluated: (1) No bFGF added; (2) 5 μL bFGF added; and (3) 15 μL bFGF added. Each μL of bFGF contained 0.1 μg of bFGF. Thus, since each SIS sheet weighed approximately 0.5 g, the maximum concentrations of bFGF for the 5 μL and 15 μL groups were about 4170 μg/mg dry weight and about 12,500 pg/mg dry weight, respectively. The bFGF content for these groups is shown in FIG. 31, as measured with respect to the dry weight of the respective samples. These results indicated that the measured concentrations of bFGF did not reach the maximum concentrations and that the sample to which 15 μL of bFGF was added did not have a measured concentration of bFGF that was three times greater than the measured concentration of bFGF in the sample to which 5 μL of bFGF was added.

Example Eleven

Figure 32:
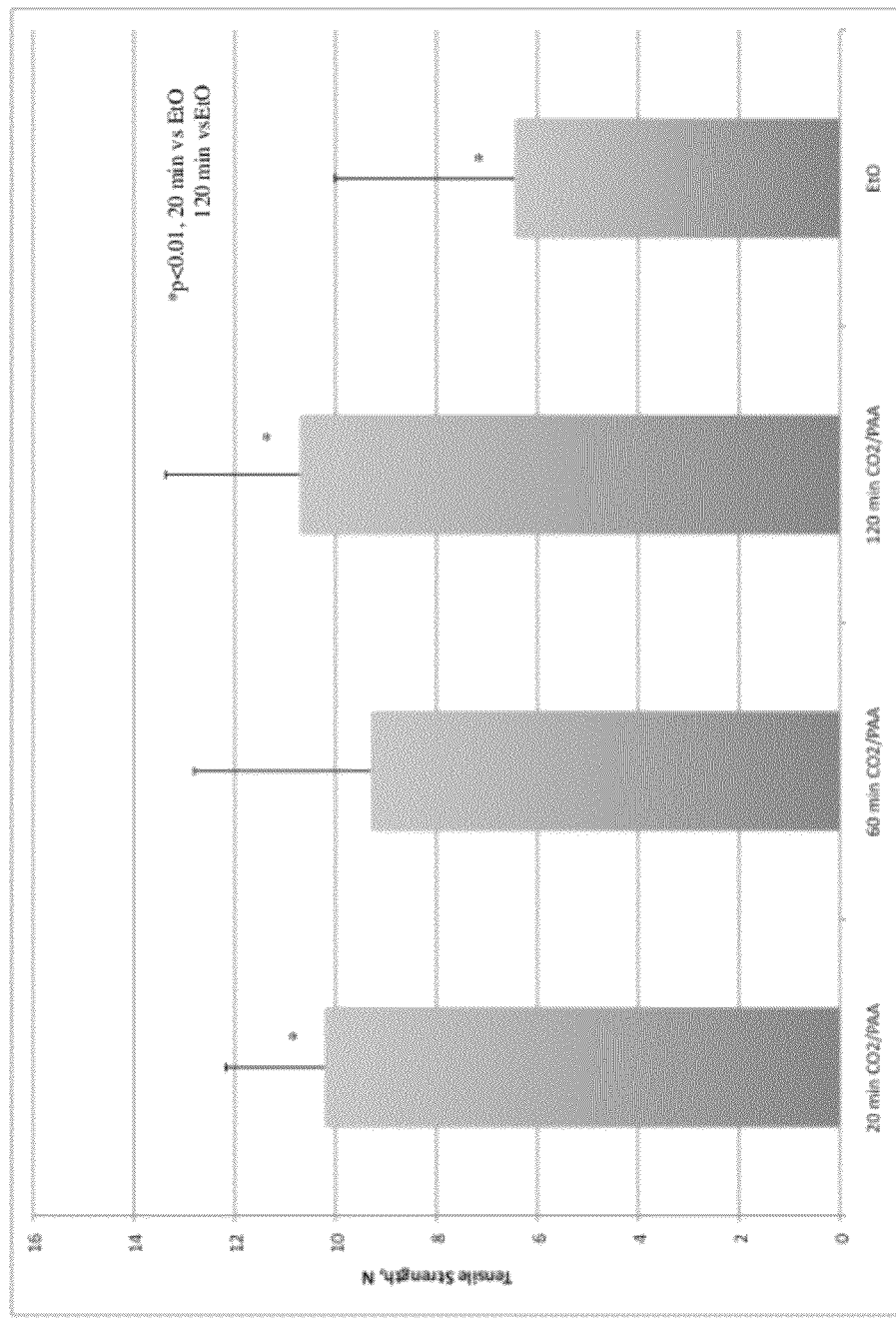
FIG. 32 depicts the results of an experiment in which the tensile strength of two-ply SIS compositions was measured following various sterilization methods, including the sterilization methods described herein.

The tensile strengths of two-ply SIS samples were measured. The following treatment groups were evaluated: (1) EtO Treatment; (2) PAA/supercritical $CO_2$ treatment for 20 minutes; (3) PAA/supercritical $CO_2$ treatment for 60 minutes; and (4) PAA/supercritical $CO_2$ treatment for 120 minutes. The tensile strength test results are shown in FIG. 32. These results indicated that the SIS samples that were processed with PAA/supercritical $CO_2$ for 20 or 120 minutes, as disclosed herein, were significantly stronger than the SIS samples that were processed with EtO.

Example Twelve

Rapid depressurization was used following gentle detergent soaks or perfusion of the ECM materials listed in Table 3 (below) at the noted concentrations and for the noted time periods. Tissues were harvested and rinsed in saline. The tissues were frozen for at least 24 hours. The tissues were thawed in cold hypotonic tris buffer on ice with 5 mM EDTA. The ECM of interest was isolated. For flat tissues (e.g., stomach submucosa, small intestine submucosa, and bladder submucosa), the tissue was stretched on a tissue stretching device and incubated in solutions in a stretched configuration. For tubular tissues (e.g., ureters, arteries, veins, and tubular SIS), the tissue was perfused with solutions using a peristaltic pump and were soaked during incubation. The tissues were incubated for 2 to 24 hours in 0.5% Triton X-100/0.5% Deoxycholic acid with 5 mM EDTA in DPBS. The tissues were rinsed 3 times for 15-30 minutes each time in DPBS. The tissues were stored at 4° C. Within 48 hours of tissue storage, the tissues were processed in supercritical $CO_2$ for 20-120 minutes followed by rapid depressurization (RDP) (decrease in pressure from 9.9 MPa to 0.69 MPa in 1 min 19 sec, corresponding to a depressurization of 2.7 MPa/10 sec).

TABLE 3

| Material | Triton X-100 Conc. | Deoxycholic Acid Conc. | TX-100/ Deoxy incubation | Supercritical $CO_2$ time |
|---|---|---|---|---|
| Porcine ureters | 0.5% | 0.5% | 24 hours | 60 minutes |
| Bovine pericardium | 0.5% | 0.5% | 24 hours | 60 minutes |
| Porcine mesothelium | 0.5% | 0.5% | 2 hours | 60 minutes |
| SIS | 0.5% | 0.5% | 2 hours | 60 minutes |

The results showed that supercritical $CO_2$ exposure followed by rapid depressurization ($SCCO_2$+RDP) did aid in the removal of cell remnants and DNA while preserving growth factors in the ECMs.

Example Thirteen

The growth factor content of various ECM compositions was analyzed using basic fibroblast growth factor (bFGF) as a representative growth factor. bFGF was selected because it is a prevalent growth factor in native ECM tissues. An enzyme-linked immunosorbent assay (ELISA, R&D Systems, Minneapolis, Minn.) was used to measure the bFGF content in the following samples: (1) Unprocessed (Raw) SIS; (2) SIS after detergent soak (TX-deoxy) only; (3) SIS after TX-deoxy and RDP (includes $SCCO_2$); (4) SIS after TX-deoxy, RDP, and PAA ($SCCO_2$ with PAA for sterilization); (5) SIS after TX-deoxy, and PAA; (6) SIS sterilized by EtO (supplied by Cook Biotech, Inc.); and (7) non-sterile SIS (supplied by Cook Biotech, Inc.).

Figure 33:
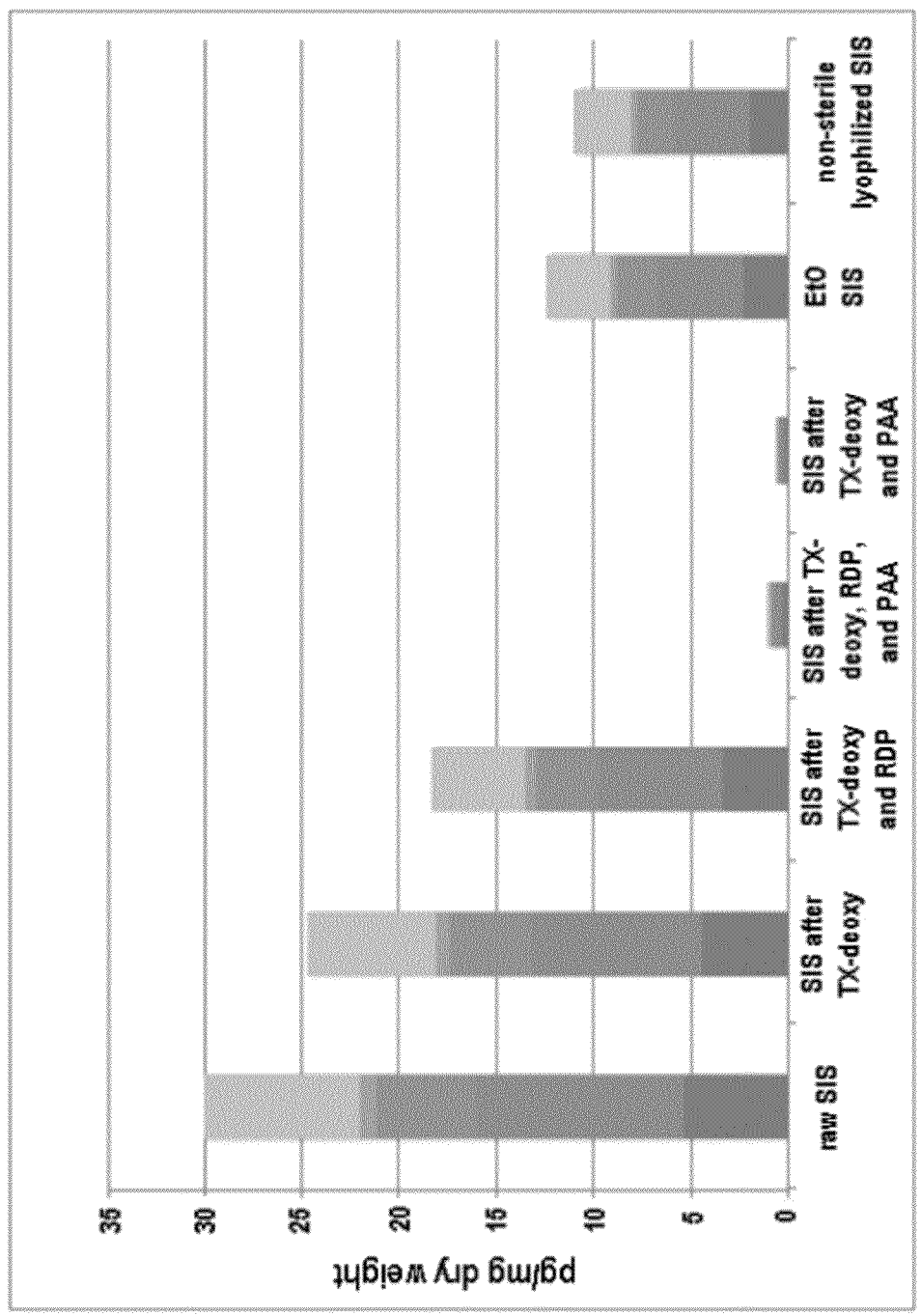
FIG. 33 depicts the results of an experiment in which native growth factor content was measured for SIS compositions following various sterilization and/or decellularization methods, including the sterilization and decellularization methods described herein.
Figure 34:
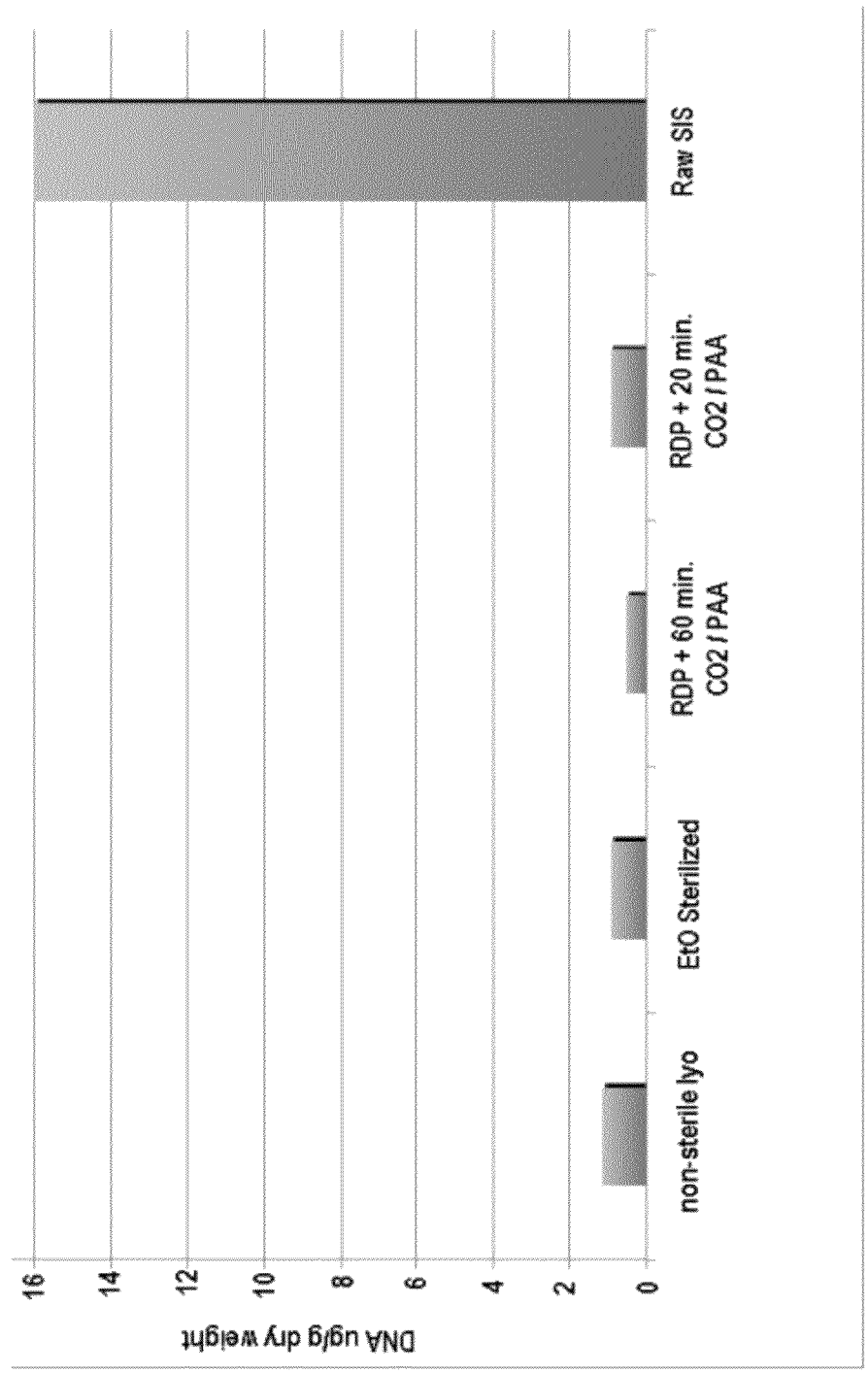
FIG. 34 shows the DNA content in SIS after it is processed in various ways. The baseline measurement is raw. The tissue was then exposed to supercritical $CO_2$ followed by rapid depressurization (RDP) to facilitate enhanced removal of DNA and cellular debris. After the RDP, the tissue was placed in supercritical $CO_2$ with peracetic acid (PAA) for sterilization. The comparison is to processed SIS either unsterilized or sterilized with ethylene oxide (ETO).
Figure 35:
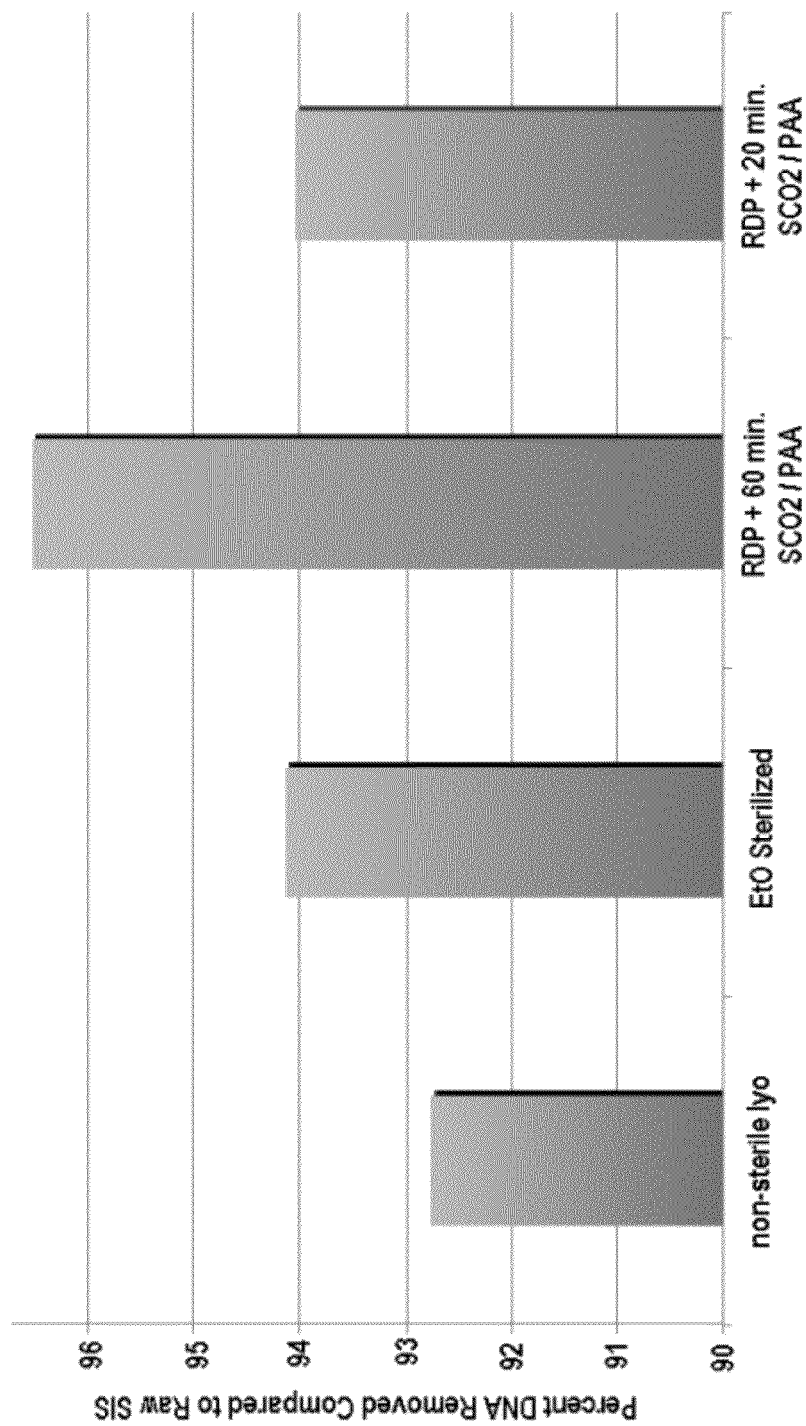
FIG. 35 shows the Percent removal of DNA from SIS after it is processed in various ways. The baseline measurement is raw. The tissue was then exposed to supercritical $CO_2$ followed by rapid depressurization (RDP) to facilitate enhanced removal of DNA and cellular debris. After the RDP, the tissue was placed in supercritical $CO_2$ with peracetic acid (PAA) for sterilization. The comparison is to processed SIS either unsterilized or sterilized with ethylene oxide (ETO).
Figure 36:
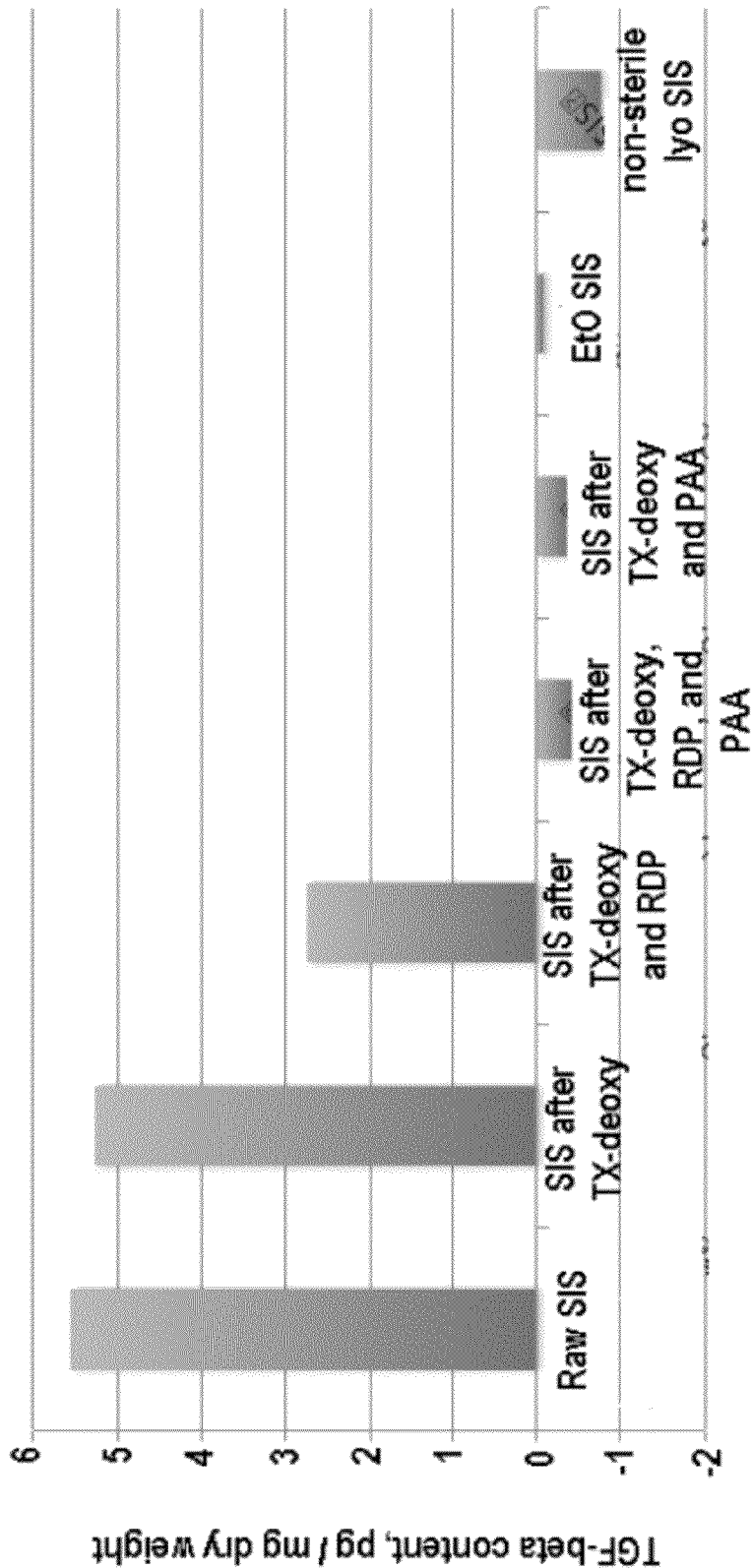
FIG. 36 shows the variable active Transforming Growth Factor (TGF-beta) content in SIS after it is processed in various ways. The baseline measurement is raw, or unprocessed SIS followed by processing with only Triton X-100 (TX-100) detergent. The tissue was then exposed to supercritical $CO_2$ followed by rapid depressurization (RDP) to facilitate enhanced removal of DNA and cellular debris. After the RDP, the tissue was placed in supercritical $CO_2$ with peracetic acid (PAA) for sterilization. The comparison is to processed SIS either unsterilized or sterilized with ethylene oxide (ETO).
Figure 37:
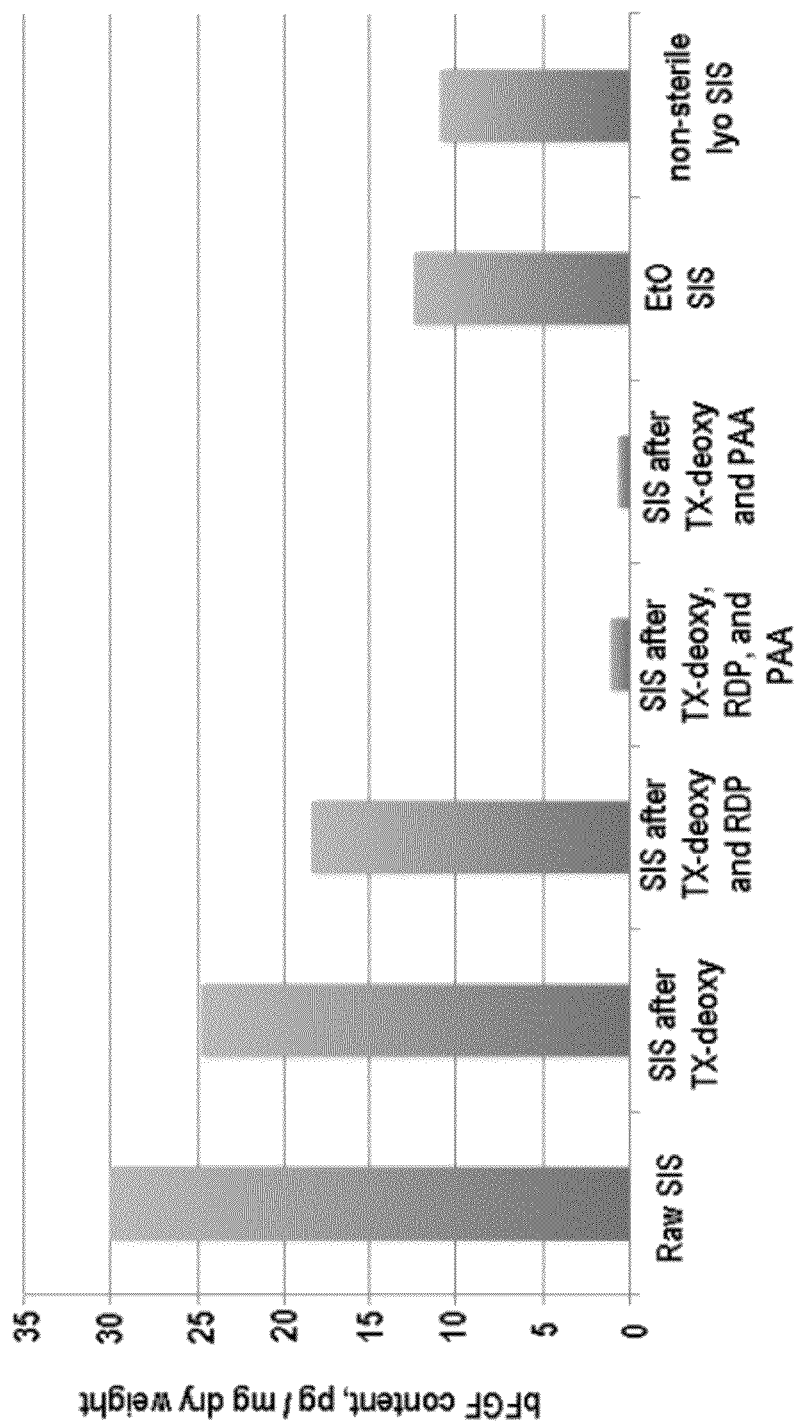
FIG. 37 shows the variable basic Fibroblast Growth Factor (bFGF) content in SIS after it is processed in various ways. The baseline measurement is raw, or unprocessed SIS followed by processing with only Triton X-100 (TX-100) detergent. The tissue was then exposed to supercritical $CO_2$ followed by rapid depressurization (RDP) to facilitate enhanced removal of DNA and cellular debris. After the RDP, the tissue was placed in supercritical $CO_2$ with peracetic acid (PAA) for sterilization. The comparison is to processed SIS either unsterilized or sterilized with ethylene oxide (ETO).
Figure 38:
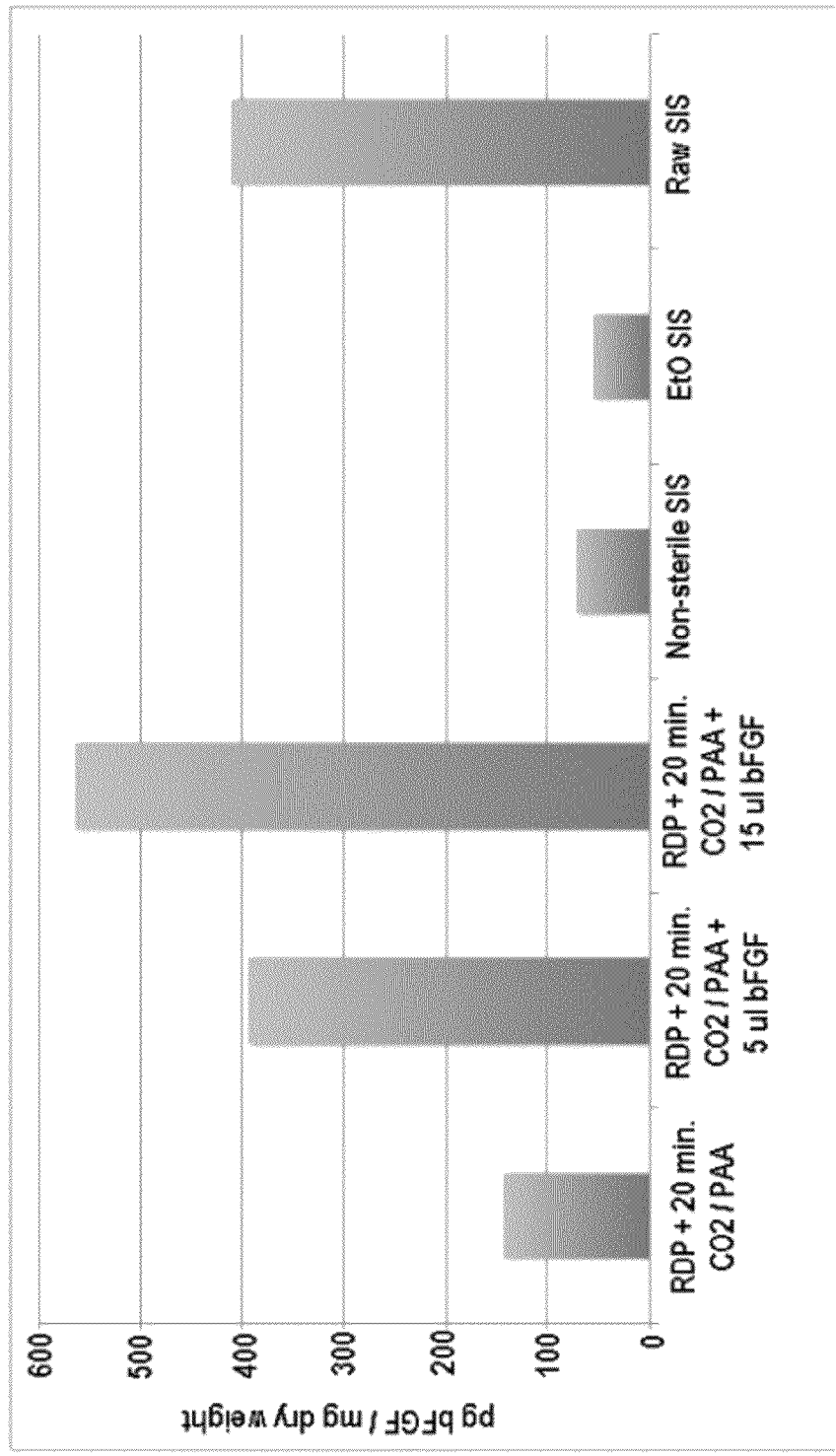
FIG. 38 shows the addition of basic Fibroblast Growth Factor (bFGF) content to SIS using rapid depressurization. The baseline measurement is raw, or unprocessed SIS. The comparison is to processed SIS either unsterilized or sterilized with ethylene oxide (ETO).
Figure 39:
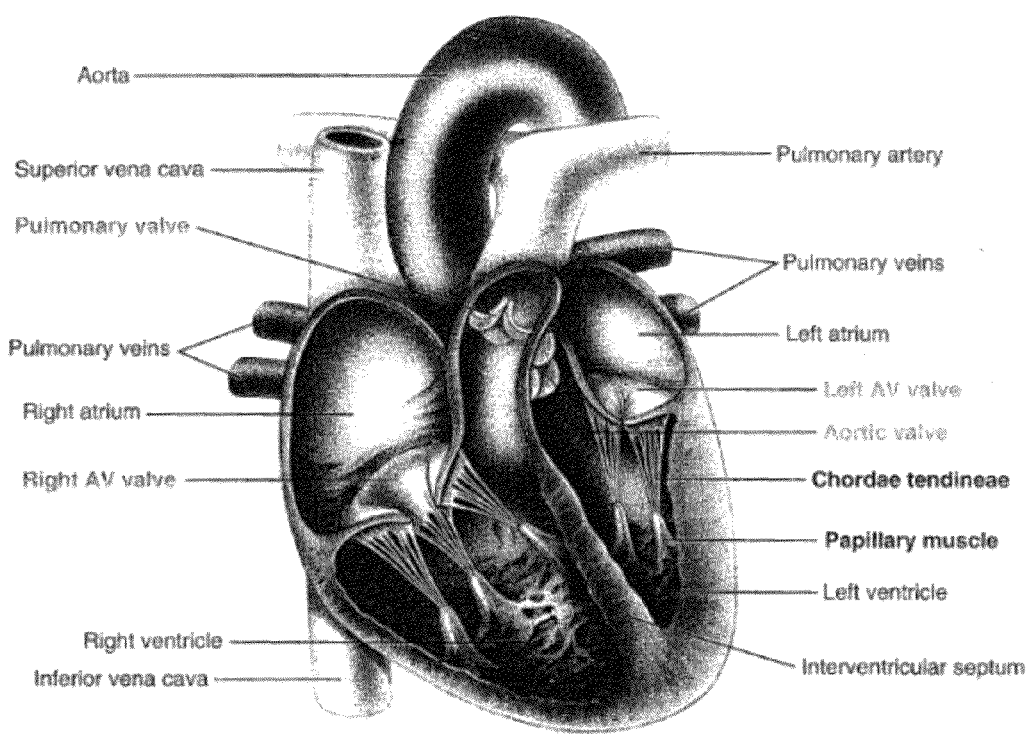
FIG. 39 is a cut-away view of the human heart.

In these studies, SIS was used to compare an ECM composition processed with and without RDP to SIS provided by Cook Biotech, Inc. Some of the processed SIS was also sterilized using the described $SCCO_2$+PAA method after decellularization. The measured growth factor content of the respective ECM compositions is shown in FIG. 33.

These results indicate that the rapid depressurization process was more effective than other decellularization processes at preserving the bFGF content and that the additional RDP processing to remove residual DNA and cell fragments results in only a small loss of bFGF. By comparison, the PAA sterilization process appeared to remove almost all of the remaining bFGF, even in the absence of RDP. Additionally, the rapid depressurization process preserved more of the bFGF content in the native SIS than the Cook decellularization methods. For purposes of these results, when the bFGF content was reduced, it is assumed that all other growth factor content was similarly reduced since the growth factors are all bound to the ECM compositions in a similar manner.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of regenerating a semi-lunar valve to replace a defective semi-lunar valve within a heart of a first subject, the defective semi-lunar valve being attached at an annular region between a ventricle of the heart of the first subject and an artery of the first subject, the method comprising:
   providing a sheet of acellular extracellular matrix (ECM) material;
   removing the defective semi-lunar valve from the heart of the first subject;
   positioning said sheet of ECM material in a folded position, said sheet having a top portion comprising a top edge of said sheet and a bottom portion comprising a bottom edge of said sheet; wherein, in said folded position, said bottom edge of said sheet is folded toward said top edge of said sheet such that said bottom edge of said sheet is spaced a first distance from said top edge of said sheet;

securing said sheet of ECM material in said folded position, thereby forming a folded ECM valve construct having an upper portion, a lower portion, a first side edge, and a second side edge, said lower portion comprising a first layer and a second layer, said first layer of said lower portion corresponding to said folded bottom portion of said sheet of said ECM material;

attaching said first layer to said second layer only at locations adjacent and along said bottom edge of said sheet, wherein said first and second layers are attached at first and second attachment points, said first attachment point being spaced from said second attachment point by a second distance, wherein a sinus-promoting portion is formed on said ECM valve construct upper portion and a commissure-promoting portion is formed on said ECM valve construct lower portion first layer;

positioning said ECM valve construct in an aligned position, in which said first side edge of said ECM valve construct is in alignment with said second side edge of said ECM valve construct;

with said ECM valve construct in said aligned position, securing said first side edge of said ECM valve construct to said second side edge of said ECM valve construct at a securement location, thereby forming an ECM valve conduit having a lumen and a longitudinal axis, wherein said lower portion of said ECM valve construct corresponds to an inlet portion of said ECM valve conduit, said inlet portion of said ECM valve conduit defining an inlet in fluid communication with said lumen of said ECM valve conduit, wherein said first layer of said lower portion of said ECM valve construct corresponds to an inner layer positioned within said lumen of said ECM valve conduit, wherein said upper portion of said ECM construct corresponds to an outlet portion of said ECM valve conduit, and wherein said second layer of said lower portion of said ECM valve construct cooperates with said upper portion of said ECM valve construct to define an outer wall of said ECM valve conduit, wherein said inner layer of said ECM valve conduit is continuous around its circumference except at said first and second attachment points and said securement location; and attaching said ECM valve conduit to the annular region of said heart of said first subject and said artery of said first subject, whereby said inlet portion of said ECM valve conduit is positioned proximate said annular region, wherein, following attachment of said ECM valve conduit to said annular region of said first subject's heart and said artery of said first subject, said commissure-promoting portion of said ECM valve conduit inner layer remodels and fuses with said upper portion of said ECM valve construct, wherein a regenerated valve leaflet of a replacement semi-lunar valve is formed in said ECM valve conduit lumen, and said sinus-promoting portion remodels and fuses with said ECM valve conduit inner layer of said ECM valve conduit, wherein a regenerated sinus portion of said replacement semi-lunar valve is formed, said regenerated valve leaflet and said regenerated sinus portion of said ECM valve conduit comprising remodeled cardiovascular tissue.

2. The method of claim 1, wherein said first attachment point and said second attachment point are positioned on a first common plane, said first common plane being perpendicular to said longitudinal axis of said ECM valve conduit.

3. The method of claim 2, wherein said first attachment point is spaced from said first side edge by a third distance, wherein said second attachment point is spaced from said second side edge by a fourth distance, and wherein said third distance and said fourth distance are equal to said second distance by which said first attachment point is spaced from said second attachment point.

4. The method of claim 1, wherein said first layer of said lower portion of said ECM valve construct is further attached to said second layer of said lower portion of said ECM valve construct at a third attachment point intermediate said first side edge and said first attachment point, wherein said first, second, and third attachment points are positioned on a second common plane, said second common plane being perpendicular to said longitudinal axis of said ECM valve conduit, and wherein an additional sinus-promoting portion is formed on said ECM valve construct upper portion and an additional commissure-promoting portion is formed on said lower portion first layer, and wherein, following attachment of said ECM valve conduit to said annular region of said first subject's heart and said first subject's artery, said additional sinus-promoting portion remodels and fuses with said inner layer of said ECM valve construct, wherein an additional regenerated sinus portion of said replacement semi-lunar valve is formed, and said additional commissure-promoting portion remodels and fuses with said upper portion of said ECM valve construct, wherein an additional regenerated valve leaflet is formed.

5. The method of claim 4, wherein said third attachment point is spaced from said first attachment point a fifth distance, and wherein said fifth distance equal to said second distance by which said first attachment point is spaced from said second attachment point.

6. The method of claim 4, wherein said first layer of said lower portion of said ECM valve construct is further attached to said second layer of said lower portion of said ECM valve construct at a fourth attachment point intermediate said second side edge and said second attachment point, wherein the first, second, third, and fourth attachment points are positioned on said second common plane.

7. The method of claim 6, wherein said fourth attachment point is spaced from said second attachment point a sixth distance, and wherein said sixth distance equal to said second distance by which said first attachment point is spaced from said second attachment point.

8. The method of claim 1, wherein said sheet of acellular ECM material is decellularized by introducing said ECM material into a reactor pressure vessel, introducing at least a first liquid sterilant into said reactor pressure vessel at a first controlled pressurization rate, pressurizing said reactor pressure vessel at a pressure in the range of 1000-3500 psi, maintaining said ECM material in contact with said first liquid sterilant for a first time period in the range of 10 min. to 24 hours, and depressurizing said reactor pressure vessel at a first depressurizing rate, said first depressurizing rate being greater than 400 psi/min.

9. The method of claim 8, wherein said first liquid sterilant comprises supercritical carbon dioxide.

10. The method of claim 8, wherein said reactor pressure vessel is maintained at a temperature of at least 31.1° C. during said pressurization of said reactor pressure vessel.

11. The method of claim 1, wherein said ECM material comprises extracellular matrix tissue from a mammalian tissue source, said mammalian tissue source being selected from the group consisting of stomach submucosa, small intestine submucosa, large intestine tissue, bladder tissue, liver tissue, heart tissue, lung tissue, kidney tissue, pancreatic tissue, prostate tissue, fetal tissue, a placenta, a ureter, vein, artery and tissue surrounding growing bone.

12. The method of claim 11, wherein said mammalian tissue source comprises mammalian tissue from a second subject.

13. The method of claim 11, wherein said ECM material includes an additional pharmacological agent.

14. The method of claim 13, wherein said pharmacological agent comprises an anti-inflammatory.

15. The method of claim 13, wherein said pharmacological agent comprises a statin.

16. The method of claim 15, wherein said statin is selected from the group consisting of atorvastatin, cerivastatin, fluvastatin, lovastatin, mevastatin, pitavastatin, pravastatin, rosuvastatin and simvastatin.

17. The method of claim 13, wherein said pharmacological agent comprises a growth factor.

18. The method of claim 17, wherein said growth factor is selected from the group consisting of a platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), platlet derived growth factor (PDGF), and placental growth factor (PLGF).

19. The method of claim 13, wherein said pharmacological agent comprises an anti-arrhythmic agent.

* * * * *

UNITED STATES PATENT AND TRADEMARK OFFICE
CERTIFICATE OF CORRECTION

Page 1 of 1

PATENT NO. : 8,696,744 B2
APPLICATION NO. : 13/480324
DATED : April 15, 2014
INVENTOR(S) : Robert G. Matheny, Christian L. Gilbert and William Novick It is certified that error appears in the above-identified patent and that said Letters Patent is hereby corrected as shown below:

Claims - Col. 35, ll. 21-29

Col. 35, ll. 21 Cancel text beginning with "18. The method" to and ending "placental growth factor (PGF)." in Col. 35, ll. 29, and insert the following claim:

--18. The method of claim 17, wherein said growth factor is selected from the group consisting of a platelet derived growth factor (PDGF), epidermal growth factor (EGF), transforming growth factor alpha (TGF-alpha), transforming growth factor beta (TGF-beta), basic fibroblast growth factor (bFGF), vascular epithelial growth factor (VEGF), hepatocyte growth factor (HGF), insulin-like growth factor (IGF), and placental growth factor (PGF).--

Signed and Sealed this
Sixth Day of October, 2015

Michelle K. Lee
*Director of the United States Patent and Trademark Office*